United States Patent
Burkart et al.

(10) Patent No.: US 9,604,973 B2
(45) Date of Patent: Mar. 28, 2017

(54) ANTI-CANCER POLYKETIDE COMPOUNDS

(71) Applicant: The Regents of the University of California, Oakland, CA (US)

(72) Inventors: Michael D. Burkart, San Diego, CA (US); James J. La Clair, San Diego, CA (US); Brian D. Jones, Jupiter, FL (US); Alexander Mandel, Mercer Island, WA (US); Reymundo Villa, San Diego, CA (US); Januario E. Castro, Carlsbad, CA (US); Manoj Kumar Kashyap, San Diego, CA (US); Deepak Kumar, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/498,934

(22) Filed: Sep. 26, 2014

(65) Prior Publication Data
US 2015/0133535 A1 May 14, 2015

Related U.S. Application Data

(63) Continuation of application No. PCT/US2013/032179, filed on Mar. 15, 2013.

(60) Provisional application No. 61/615,862, filed on Mar. 26, 2012.

(51) Int. Cl.
*C07D 313/00* (2006.01)
*C07D 407/06* (2006.01)

(52) U.S. Cl.
CPC ......... *C07D 407/06* (2013.01); *C07D 313/00* (2013.01)

(58) Field of Classification Search
CPC .............................. C07D 313/00; C07D 407/06
See application file for complete search history.

(56) References Cited

U.S. PATENT DOCUMENTS 7,667,052 B2    2/2010   Mizui et al.

FOREIGN PATENT DOCUMENTS

WO   WO-2013/148324 A1   10/2013

OTHER PUBLICATIONS

Mizogami et al., caplus an 1993:190110.*
Mizui et al., caplus an 2002:594837, 2002.*
Butler, M.S. (2008, e-published May 7, 2008). "Natural Products to Drugs: Natural Product-Derived Compounds in Clinical Trials," *Natural Product Reports* 25:475-516.
Butler, M.S. (Sep. 12, 2013, e-published Aug. 27, 2013). "Remediating Cancer Via Splicing Modulation," *J. Med. Chem.* 56(17):6573-6575.
Crimmins, M.T. et al. (1997). "Asymmetric Aldol Additions with Titanium Enolates of Acyloxazolidinethiones: Dependence of Selectivity on Amine base and Lewis Acid Stoichiometry," *J. Am. Chem. Soc.* 119(33):7883-7884.
Delaunay, D. et al. (1995). "Reactivity of β-Amino Alcohols with Carbon Disulfide. Study on the Synthesis of 2-Oxazolidinethiones and 2-Thiazolidinethiones," *J. Org. Chem.* 60(20):6604-6607.
Fan, L. et al. (Jun. 17, 2011, e-published Mar. 7, 2011). "Sudemycins, Novel Small Molecule Analogues of FR901464, Induce Alternative Gene Splicing," *ACS Chem. Biol.* 6(6):582-589.
Gundluru, M.K. et al. (2011, e-published Jul. 21, 2011). "Design, Synthesis and Initial Biological Evaluation of a Novel Pladienolide Analog Scaffold," *MedChemComm.* 2:904-908.
Hasegawa, M. et al. (Mar. 18, 2011, e-published Jan. 13, 2011). "Identification of SAP155 as the Target of GEX1A (Herboxidiene), an Antitumor Natural Product," *ACS Chem. Biol.* 6(3):229-233.
Kaida, D. et al. (Sep. 2007, e-published Jul. 22, 2007). "Spliceostatin a Targets SF3b and Inhibits Both Splicing and Nuclear Retention of Pre-mRNA," *Nat. Chem. Biol.* 3(9):576-583.
Kanada, R.M. et al. (2007). "Total Synthesis of the Potent Antitumor Macrolides Pladienolide B and D," *Angew. Chem. Int. Ed. Engl.* 46(23):4350-4355.
Katsuki, T. et al. (Aug. 1980). "The First Practical Method for Asymmetric Epoxidation," *J. Am. Chem. Soc.* 102(18):5974-5976.
Ko, K-S. et al. (Nov. 21, 2010, e-published Aug. 19, 2010). "Synthetic Studies on the Mycolactone Core," *Org. Biomol. Chem.* 8(22):5159-5165.
Kotake, Y. et al. (Sep. 2007, e-published Jul. 22, 2007). "Splicing Factor SF3b as a Target of the Antitumor Natural Product Pladienolide," *Nat. Chem. Biol.* 3(9):570-575.
Lagisetti, C. et al. (Oct. 9, 2008, e-published Sep. 13, 2008). "Antitumor Compounds Based on a Natural Product Consensus Pharmacophore," *J. Med. Chem.* 51(19):6220-6224.
Light, J. et al. (1990). "A Water Soluble Tin Hydride Reagent," *Tetrahedron Letters* 31(21):2957-2958.
Machida, K. et al. (Jun. 2009). "One-Pot Fermentation of Pladienolide D by Streptomyces Platensis Expressing a Heterologous Cytochrome P450 Gene," *J. Biosci. Bioeng.* 107(6):596-598.
Mandel, A.L. et al. (Sep. 15, 2007, e-published Jul. 7, 2007). "A Synthetic Entry to Pladienolide B and FD-895," *Bioorg. Med. Chem. Lett.* 17(18):5159-5164.
Mans, D.M. et al. (Sep. 17, 2004). "Novel Kumada Coupling Reaction to Access Cyclic (2-Azaallyl)Stannanes. Cycloadditions of Cyclic Nonstabilized 2-Azaallyllithium Species Derived from Cyclic (2-Azaallyl)Stannanes," *J. Org. Chem.* 69(19):6419-6426.
Marshall, J.A. et al. (Jul. 1, 1994). "Synthesis of Syn and Anti Homopropargylic and Allenic Alcohols through Diastereoselective SE2' Addition of a Common Chiral Allenylstannane Precursor to Aldehydes," *The Journal of Organic Chemistry* 59(13):3509-3511.
Marshall, J.A. (Oct. 26, 2007, e-published Jun. 27, 2007). "Chiral Allylic and Allenic Metal Reagents for Organic Synthesis," *J. Org. Chem.* 72(22):8153-8166.
More, J.D. et al. (Aug. 22, 2002)." a simple and advantageous protocol for the oxidation of alcohols with O-iodoxybenzoic acid (IBX)," *Org. Lett.* 4(17):3001-3003.
Muller, S. et al. (Aug. 5, 2011, e-published Jun. 27, 2011). "Synthesis of a Pladienolide B Analogue with the Fully Functionalized Core Structure," *Org. Lett* 13(15):3940-3943.

(Continued)

*Primary Examiner* — Sun Jae Yoo
(74) *Attorney, Agent, or Firm* — Mintz Levin Cohn Ferris Glovsky and Popeo, P.C.

(57) ABSTRACT

Provided herein, inter alia, are anticancer polyketides. The uses of the polyketides described herein include treatment of cancer, for example, through regulation of the spliceosome and detection of spliceosome inhibition.

14 Claims, 24 Drawing Sheets

(56) References Cited

OTHER PUBLICATIONS

Ramachandran, P.V. et al. (Oct. 2, 2003). "Synthesis of Homoallylic Chiral Tertiary Alcohols via Chelation-Controlled Diastereoselective Nucleophilic Addition on α-Alkoxyketones: Application for the Synthesis of the $C_1C_{11}$ Subunit of 8-epi-Fostriecin," *Org. Lett.* 5(20):3755-3757.

Skaanderup, P.R. et al. (Jul. 3, 2008, e-published May 30, 2008). "Synthesis of the Macrocyclic Core of (-)-Pladienolide B," *Org. Lett.* 10(13):2821-2824.

Stewart, I.C. et al. (Apr. 12, 2007, e-published Mar. 23, 2007). "Highly Efficient Ruthenium Catalysts for the Formation of Tetrasubstituted Olefins via Ring-Closing Metathesis," *Org. Lett.* 9(8):1589-1592.

Still, W.C. et al. (1980). "Chelation-Controlled Nucleophilic Additions. 1. A Highly Effective System for Asymmetric Induction in the Reaction of Organometallics with β-Alkoxyketones," 21(11):1031-1034.

Stille, J.K. et al. (1987). "Stereospecific Cross-Coupling of Vinyl Halides with Vinyl Tin Reagents Catalyzed by Palladium," *J. Am. Chem. Soc.* 109(3):813-817.

Villa, R. et al. (Nov. 2, 2012, e-published Oct. 16, 2012). "Structure of FD-895 Revealed Through Total Synthesis," *Org. Lett.* 14(21):5396-5399.

Villa, R. et al. (Sep. 12, 2013, e-published Aug. 21, 2013). "Stabilized Cyclopropane Analogs of the Splicing Inhibitor FD-895," *Journal of Medicinal Chemistry*, 56(17):6576-6582.

Wadsworth, W.S. et al. (Apr. 5, 1961). "The Utility of Phosphonate Carbanions in Olefin Synthesis," *J. Am. Chem. Soc.* 83:1733-1738.

Yokoi, A. et al. (Dec. 2011, e-published Oct. 31, 2011). "Biological Validation that SF3b is a Target of the Antitumor Macrolide Pladienolide," *Febs J.* 278(24):4870-4880.

Zhang, Y. et al. (Jan. 8, 2004). "Highly Selective Asymmetric Acetate Aldol Reactions of an N-Acetyl Thiazolidinethione Reagent," *Org. Lett.* 6(1):23-25.

U.S. Appl. No. 61/615,862, filed Mar. 26, 2012, by Burkart et al. (Copy not attached).

\* cited by examiner

*Figure 5*
HCT-116 Assay (nM)
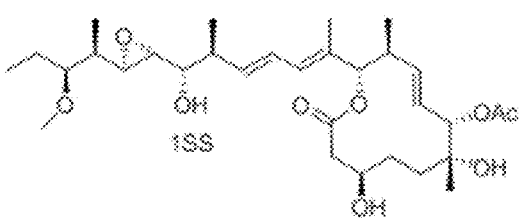
23.0 +/- 1.2
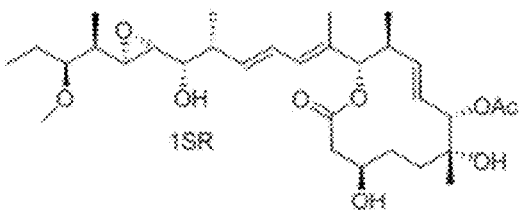
3.7 +/- 0.2
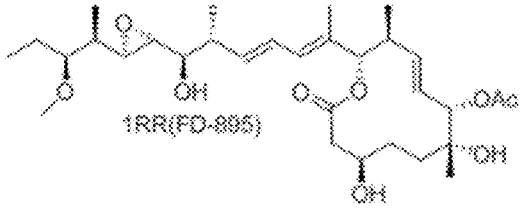
24.2 +/- 0.9
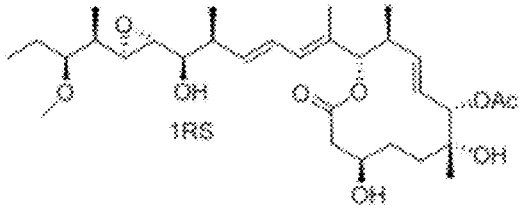
0.80 +/- 0.05
*Authentic FD-895 is 23.5 nM Scheme S1. Gram scale synthesis of component 8.

Scheme S2. Synthesis of core macrolide 21.

Scheme S3. Synthesis of isomers 1SS, 1SR, 1RS, and 1RR.

$^1$H-NMR (400 MHz) and $^{13}$C-NMR (100 MHz) spectra of alkyne 24a in CDCl$_3$ $^1$H-NMR (400 MHz) and $^{13}$C-NMR (100 MHz) spectra of alkyne 24b in CDCl$_3$ Figure 18
Figure 18A
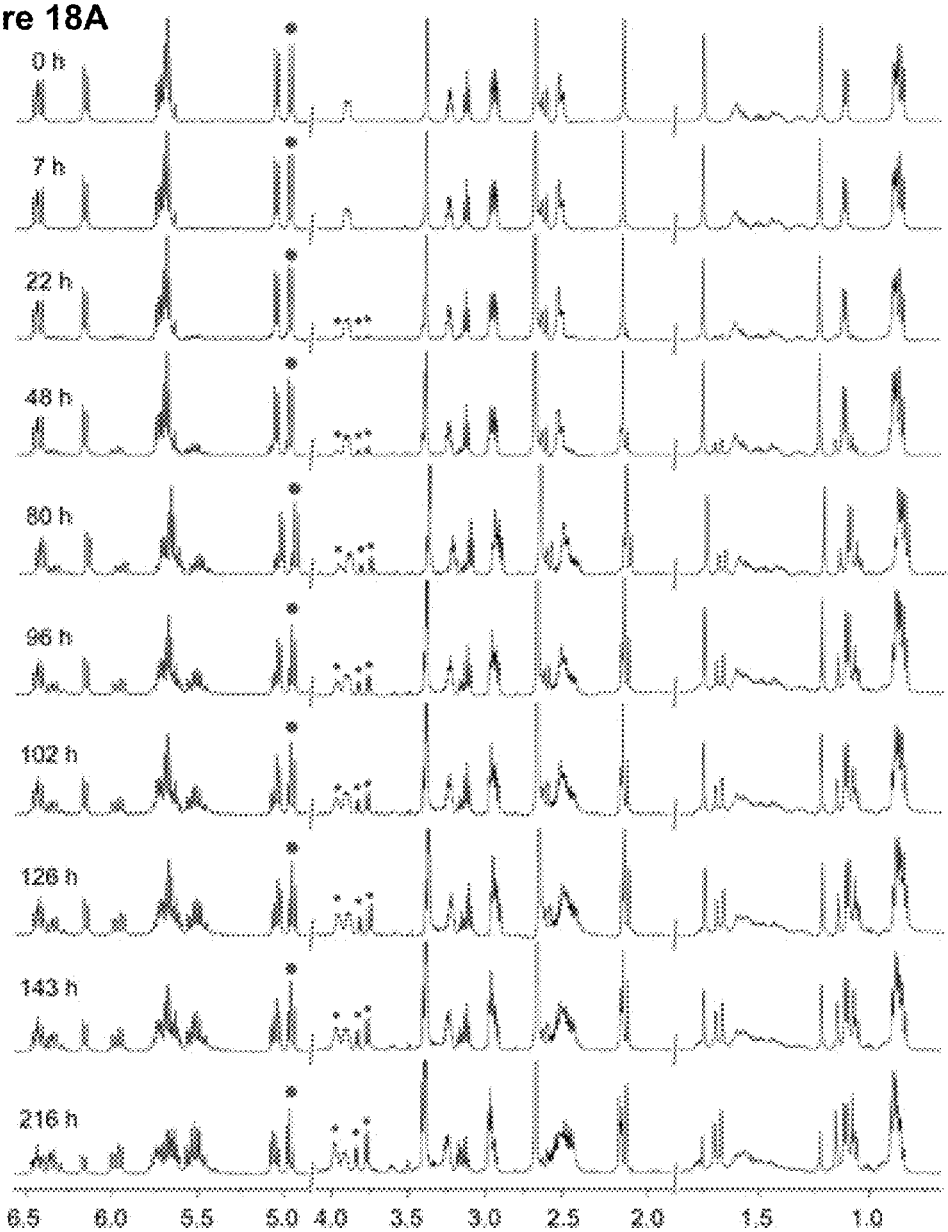
Figure 18B
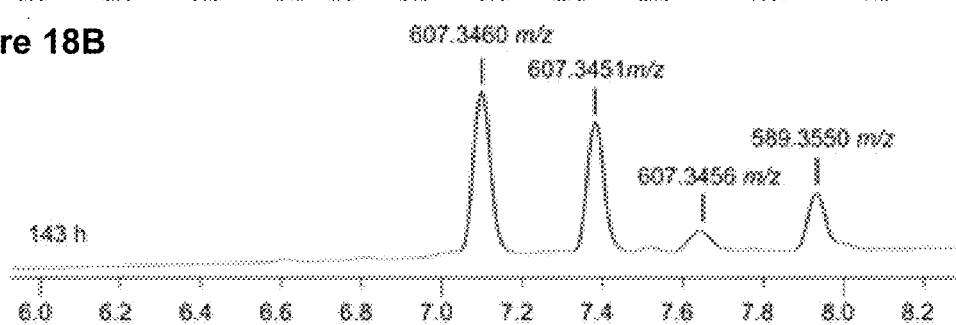

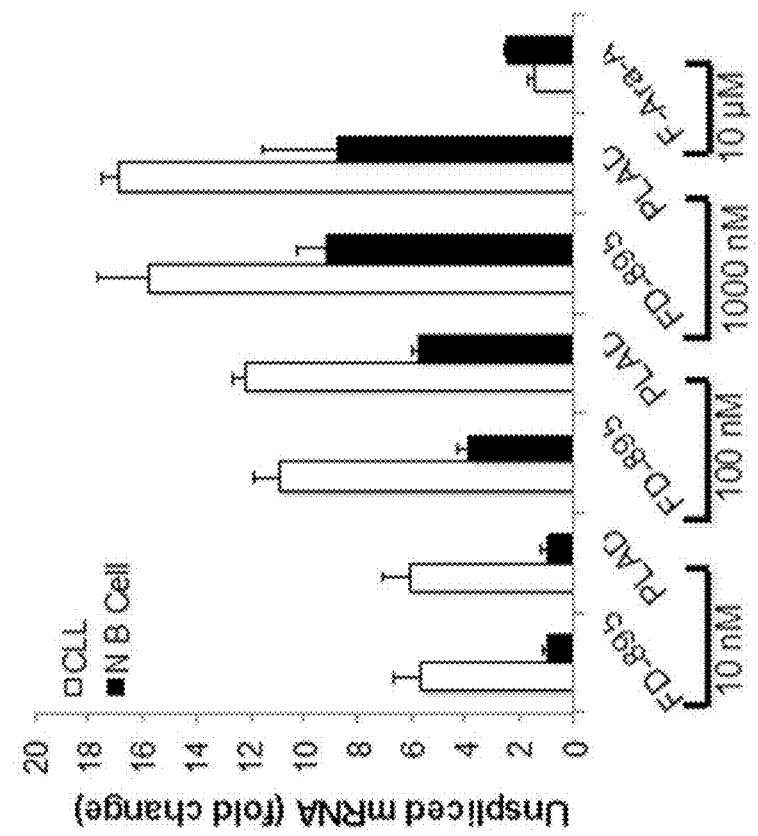
Figure 25A. DNAJB1
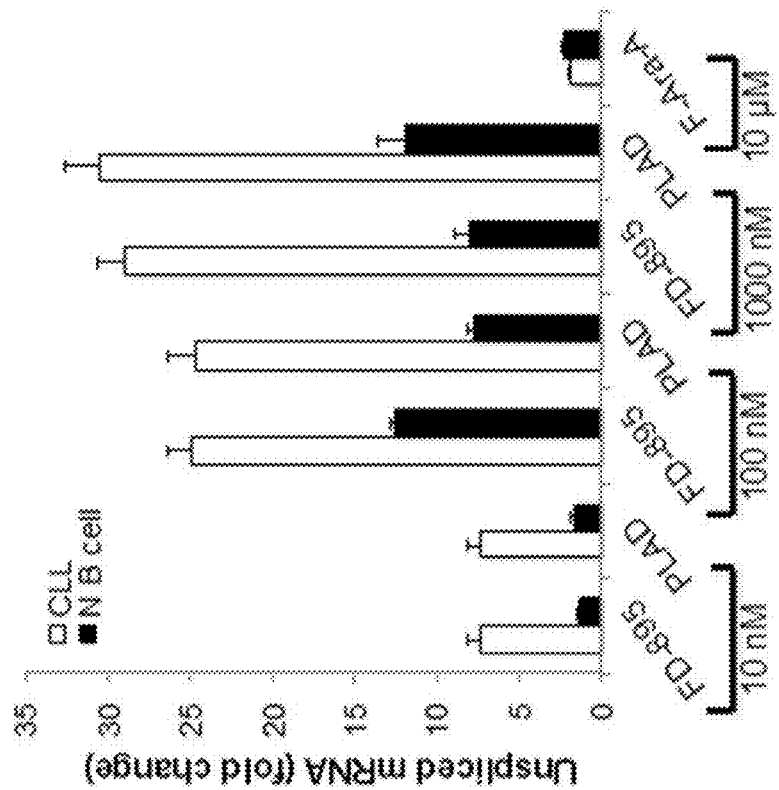
Figure 25B. RIOK3

ANTI-CANCER POLYKETIDE COMPOUNDS

CROSS-REFERENCES TO RELATED APPLICATIONS

This application is a continuation of PCT Application No. PCT/US2013/032179, filed Mar. 15, 2013, which claims priority to Provisional Application No. 61/615,862 filed Mar. 26, 2012.

STATEMENT AS TO RIGHTS TO INVENTIONS MADE UNDER FEDERALLY SPONSORED RESEARCH AND DEVELOPMENT

This invention was made with government support under grants: RSG-06-011-01-CDD awarded by the American Cancer Society, and grant 3R01GM086225-01S1 awarded by the National Institutes of Health (NIH). The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 88654-920523_ST25.TXT, created Nov. 10, 2014, 2,909 bytes, machine format IBM-PC, MS-Windows operating system, is hereby incorporated by reference.

FIELD OF THE INVENTION

The present invention relates in general to the field of anticancer agents, and methods of synthesis and use of the same.

BACKGROUND OF THE INVENTION

FD-895 was the first member of a family of 12-membered macrolides identified with potent cytotstatic activity in select tumor cell lines during hypoxia response. FD-895 is shown to inhibit the proliferation of tumor cell growth by altering natural gene splicing. FD-895 has $IC_{50}$ value of 24.2±0.9 nM and has been reported to have hydrolytic instability. Additional studies have led to the isolation of a family of related macrolides including pladienolides. The early suspension of clinical trials for such compounds has created a need for new cancer therapies.

Chronic lymphocytic leukemia (CLL), one of the most common types of leukemia, characterized by an abnormal population of B lymphocytes in the blood that display a unique but characteristic pattern of cell surface markers such as the atypical co-production of CD5 and CD23. Despite the recent advance of combination treatments such as FCR (fludarabine, cyclophosphamide and rituximab) that confers a survival advantage, there is still no cure for CLL. Additionally, high-risk CLL groups such as patients with 17p deletion have a worse diagnosis and often fail to respond to therapy. Given these complications, there is an immediate need for agents that act on CLL through novel pathways.

Splicing, the removal of introns and joining of exons from nascent pre-mRNA, has recently gained attention as a target for cancer given the distinct splicing patterns identified both in tumor cell and metastatic tumor populations. Recently, a series of studies identified heterozygous missense mutations in U2AF1 and SF3B1 genes associated with myelodysplastic syndrome (MDS), and SF3B1 is frequently mutated in both MDS and chronic lymphocytic leukemia (CLL). Splicing plays an important role in human biology and its relevance in cancer is rapidly emerging. Recent advances in oligonucleotide sequencing demonstrate that alternative splicing and gene mutations involved in the spliceosome system can have a role in tumorigenesis and confer clinical prognosis in haematologic diseases including chronic lymphocytic leukemia (CLL). However, there are few, if any, well-defined molecular probes that can be used to monitor splicing events the role of the spliceosome system, as a molecular target in cancer has not been completely defined. Thus, the identification of selective and potent derivatives of macrolides like FD-895 with enhanced efficacy is of crucial and significant value. Provided herein are solutions to these and other problems in the art.

BRIEF SUMMARY OF THE INVENTION

Provided herein, inter alia, are synthetic analogues of a class of macrolides. The analogues may be used in the treatment of cancer. A method of detecting spliceosome inhibition using a test compound is also provided.

In a first aspect is a compound having the formula:

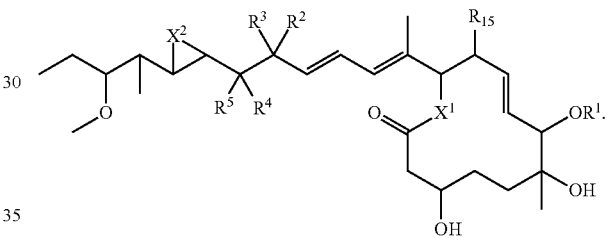

$X^1$ is N, O, or $CH_2$. $X^2$ is O or $C(R^6)(R^7)$. $R^6$ and $R^2$ are independently hydrogen, halogen, substituted or unsubstituted alkyl, substituted or unsubstituted aryl, —$OR^{12}$, —OC(O)$R^{12}$, —OC(O)O$R^{12}$, or —OC(O)N$R^{13}R^{14}$. $R^1$ is hydrogen, —C(O)$R^8$, —OC(O)$R^8$, —OC(O)O$R^8$, or —NHC(O)NH$R^8$. $R^2$, $R^3$, $R^4$, and $R^5$ are each independently selected from hydrogen, substituted or unsubstituted alkyl, —$OR^9$, —OC(O)$R^9$, —OC(O)O$R^9$, or —OC(O)N$R^{16}R^{11}$. $R^8$, $R^9$, $R^{10}$, $R^{11}$, $R^{12}$, $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{15}$ is hydrogen, halogen, $CF_3$, $CCl_3$, $CBr_3$, $CI_3$, substituted or unsubstituted alkyl.

In another aspect is a compound having the formula:

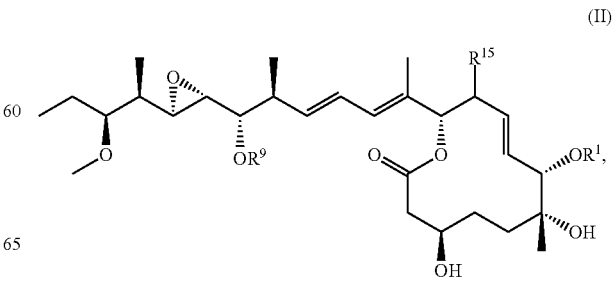

(II)

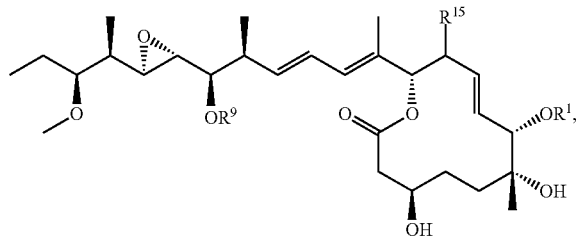
(III)

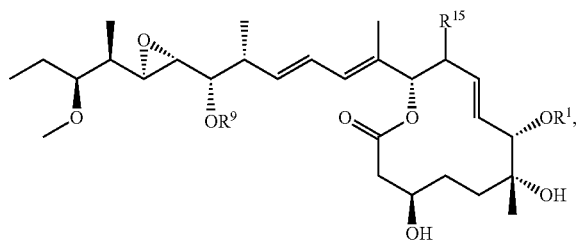
(IV)

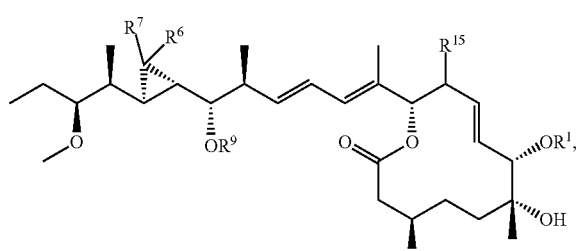
(V)

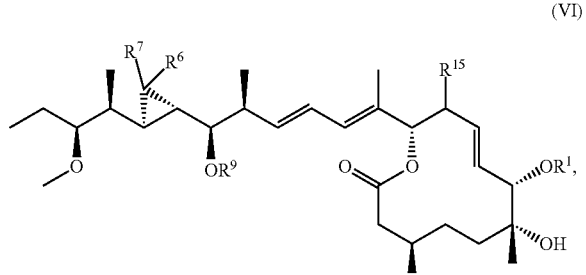
(VI)

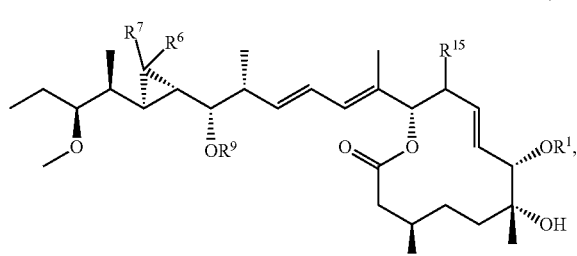
(VII)

or

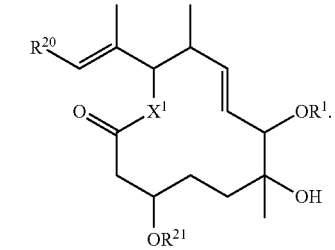
(VIII)

$R^1$, $R^6$, $R^7$, $R^9$, and $R^{15}$ are as defined herein.

In another aspect is a compound having formula:

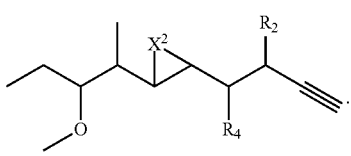
(XVI)

$X^1$ and $R^1$ are as defined herein. $R^{20}$ is halogen, —SO$_3$CF$_3$, or —SO$_3$(C$_6$H$_6$)CH$_3$. $R^{21}$ is hydrogen, —C(O)R$^8$, —OCO(O)R$^8$, —OC(O)OR$^8$, NHC(O)NHR$^8$.

In another aspect is a compound having formula:

(XVII)

$X^2$, $R^2$, and $R^4$ are as defined herein.

In another aspect is provided a pharmaceutical composition. The composition includes a compound having formula (I), (II), (III), (IV), (V), (VI), (VII), or (VIII) and a pharmaceutically acceptable excipient.

In another aspect a method of treating cancer is provided. The method includes administering to a subject in need thereof, a therapeutically effective amount of a compound of formula (I), (II), (III), (IV), (V), (VI), (VII), or (VIII).

In another aspect, a method of detecting spliceosome inhibition using a test compound is provided. The method includes contacting a cell with the test compound, extracting an mRNA from the cell to produce an extracted mRNA, reverse transcribing the mRNA using intron-specific primers to form an intron cDNA, amplifying the intron cDNA to form a plurality of amplified intron cDNA's, and detecting the presence of the amplified intron cDNAs to detect spliceosome inhibition resulting from the test compound.

BRIEF DESCRIPTION OF THE DRAWINGS

FIG. 5: Biological activities of synthetic analogues 1SS, 1SR, 1RR (FD-895), and 1RS.Biological

FIG. 18A-18B: Hydrolysis of FD-895 (1a).
FIG. 18A) NMR monitoring of the incubation of 10 mM 1a in D$_2$O/DMSO-d$_6$ (10:1) at 37° C. Hydrolysis occurs as marked by a shift of the C11 proton (large to small circles). Assignments of 3a, 3b and 3c were made based on coupling constant and gCOSY analyses.
FIG. 18B) LdC-HRMS trace depicting the products at 143 h including acids 3a-3c (mass calcd. for C$_{31}$H$_{52}$O$_{10}$Na=607.3453 m/z) along with unhydrolized 1a (mass calcd. for C$_{31}$H$_{50}$O$_9$Na=589.3347 m/z). Exact masses [M+Na]$^+$ are provided for each peak.

FIG. 25A-25B: Dose-dependent increase of unspliced mRNA by FD-895 and PLAD in CLL but not significantly in normal B cells: CLL and normal B cells were treated with 10, 100, and 1000 nM of FD-895 and PLAD and 10 µM of F-Ara-A for 4 hours. Quantitative RT-PCR using primers specific for each intron quantified unspliced mRNA for DNAJB1 (FIG. 25A) and RIOK3 (FIG. 25B). GAPDH was used for normalization. This result validated two times independently. Error bars indicate S.D.

DETAILED DESCRIPTION

I. Definitions

Figure 1:
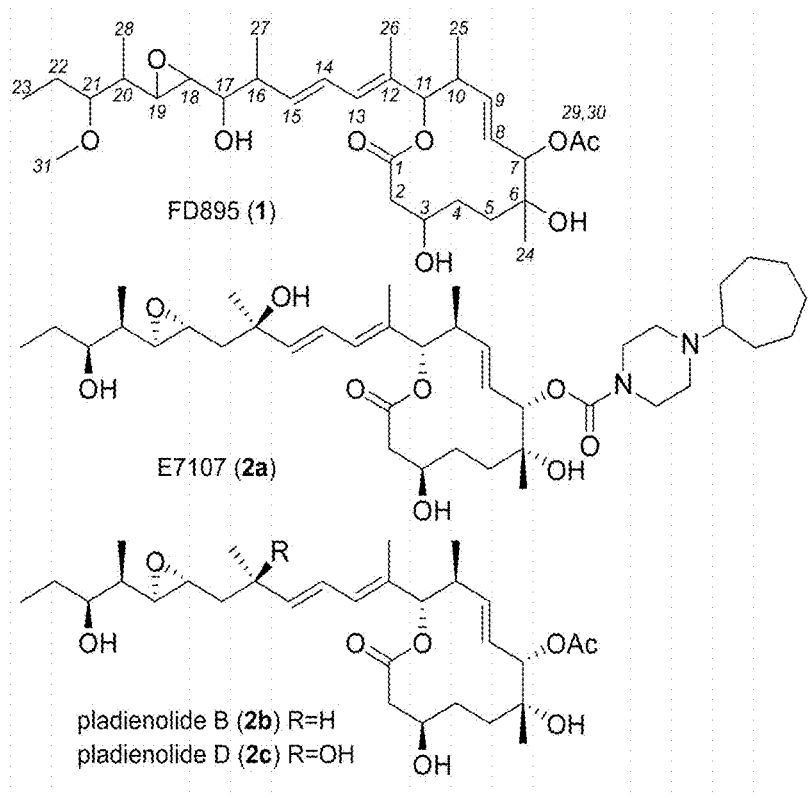
FIG. 1: Structure of natural analogue FD-895, E7107 and pladienolides B and D.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, B, As, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—$S(O)_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. A heteroaryl group substituent may be a —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein. Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substitutents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The term "oxo," as used herein, means an oxygen that is double bonded to a carbon atom.

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —NR'SO$_2$R", —NR'C=(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —NR'NR"R'", —ONR'R", —NR'C=(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C=(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), Boron (B), Arsenic (As), and silicon (Si).

A "substituent group," as used herein, means a group selected from the following moieties:
(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, and heteroaryl, substituted with at least one substituent selected from:
  (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, and heteroaryl, substituted with at least one substituent selected from:
    (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, or heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O) NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and each substituted or unsubstituted heterocycloalkyl is a substituted or unsubstituted 3 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, and/or each substituted or unsubstituted heterocycloalkyl is a substituted or unsubstituted 3 to 7 membered heterocycloalkyl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, and/or each substituted or unsubstituted heterocycloalkylene is a substituted or unsubstituted 3 to 7 membered heterocycloalkylene.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present invention, whether radioactive or not, are encompassed within the scope of the present invention.

The symbol "⌇" denotes the point of attachment of a chemical moiety to the remainder of a molecule or chemical formula.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13}B$, $R^{13C}$, $R^{13D}$, etc. is defined within the scope of the definition of $R^{13}$ and optionally differently.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA.

The terms "DNA" and "RNA" refer to deoxyribonucleic acid and ribonucleic acid, respectively.

Where a method disclosed herein refers to "amplifying" a nucleic acid, the term "amplifying" refers to a process in which the nucleic acid is exposed to at least one round of extension, replication, or transcription in order to increase (e.g., exponentially increase) the number of copies (including complimentary copies) of the nucleic acid. The process can be iterative including multiple rounds of extension, replication, or transcription. Various nucleic acid amplification techniques are known in the art, such as PCR amplification or rolling circle amplification.

A "primer" as used herein refers to a nucleic acid that is capable of hybridizing to a complimentary nucleic acid sequence in order to facilitate enzymatic extension, replication or transcription.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The terms "identical" or percent "identity," in the context of two or more nucleic acids, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

A variety of methods of specific DNA and RNA measurements that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., quantitative PCR, dot blot, or array).

The sensitivity of the hybridization assays may be enhanced through use of a nucleic acid amplification system that multiplies the target nucleic acid being detected. Amplification can also be used for direct detection techniques. Examples of such systems include the polymerase chain reaction (PCR) system and the ligase chain reaction (LCR) system. Other methods include the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including Taqman® and molecular beacon probes can be used to monitor amplification reaction products in real time.

The terms "spliceosome" or "spliceosomal" are used according to their common and ordinary meaning and refer to the process or complex involved in removal of introns from transcribed pre-mRNA. A spliceosome may include a complex of small nuclear RNA (snRNA) and protein subunits.

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or psychiatric evaluation. The term "treating" and conjugations thereof, include prevention of an injury, pathology, condition, or disease.

A "therapeutically effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

A "test compound" as used herein refers to an experimental compound used in a screening process to identify activity, non-activity, or other modulation of a particularized biological target or pathway.

The term "modulation", "modulate", or "modulator" are used in accordance with their plain ordinary meaning and refer to the act of changing or varying one or more properties. "Modulator" refers to a composition that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

"Disease" or "condition" refer to a state of being or health status of a patient or subject capable of being treated with the compounds or methods provided herein.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The term "associated" or "associated with" in the context of a substance or substance activity or function associated with a disease means that the disease is caused by (in whole or in part), or a symptom of the disease is caused by (in whole or inpart) the substance or substance activity or function.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, metastatic bone cancer, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The $P_{388}$ leukemia model is widely accepted as being predictive of in vivo anti-leukemic activity. It is believed that a compound that tests positive in the $P_{388}$ assay will generally exhibit some level of anti-leukemic activity in vivo regardless of the type of leukemia being treated. Accordingly, the present invention includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

II. COMPOSITIONS OF MATTER

In a first aspect is a compound having the formula:

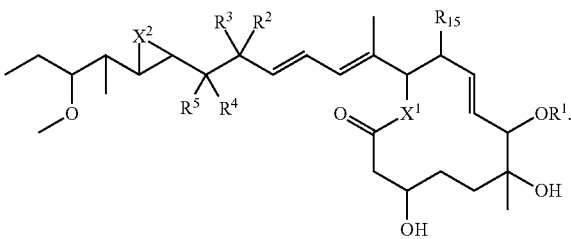

$X^1$ is N, O, or $CH_2$. $X^2$ is O or $C(R^6)(R^7)$. $R^6$ and $R^7$ are independently hydrogen, halogen, substituted or unsubstituted alkyl, substituted or unsubstituted aryl, $-OR^{12}$, $-OC(O)R^{12}$, $-OC(O)OR^{12}$, or $-OC(O)NR^{13}R^{14}$. $R^1$ is hydrogen, —C(O)R$^8$, —OC(O)R$^8$, —OC(O)OR$^8$, or —NHC(O)NHR$^8$. R$^2$, R$^3$, R$^4$, and R$^5$ are each independently selected from hydrogen, substituted or unsubstituted alkyl, —OR$^9$, —OC(O)R$^9$, —OC(O)OR$^9$, or —OC(O)NR$^{10}$R$^{11}$. R$^8$, R$^9$, R$^{10}$, R$^{11}$, R$^{12}$, R$^{13}$ and R$^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{15}$ is hydrogen, halogen, CF$_3$, CCl$_3$, CBr$_3$, CI$_3$, or substituted or unsubstituted alkyl.

In certain embodiments X$^1$ is O. In certain embodiments R$^2$ is methyl. In certain embodiments R$^4$ is —OR$^9$ where R$^9$ may be hydrogen or C$_1$-C$_4$ unsubstituted alkyl. R$^9$ may be hydrogen. When X$^1$ is O, R$^2$ is attached to a chiral carbon having (S) stereochemistry, and R$^4$ may be attached to a carbon having (S) or (R) stereochemistry. When R$^2$ is attached to a carbon having (S) stereochemistry, R$^4$ may be attached to a carbon having (S) stereochemistry. The compound may have formula (II). When R$^2$ is attached to a carbon having (S) stereochemistry, R$^4$ may be attached to a carbon having (R) stereochemistry. The compound may have formula (III). When X$^1$ is O, R$^2$ may be attached to a chiral carbon having (R) stereochemistry, and R$^4$ may be attached to a carbon having (S) stereochemistry. The compound may have formula (IV).

In another aspect is a compound having the formula:

(II)

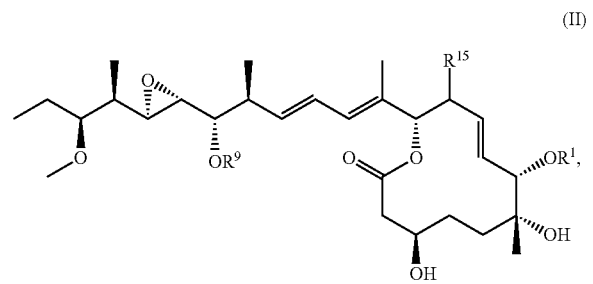

(III)

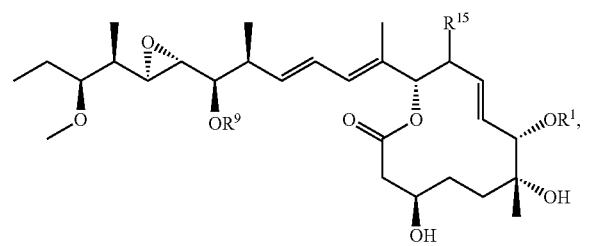

(IV)

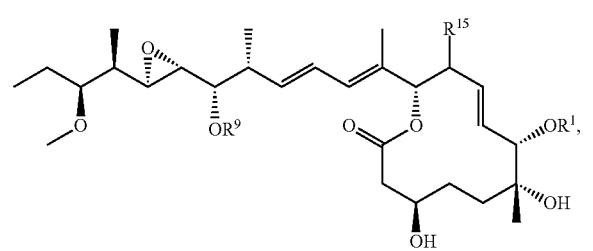

(V)

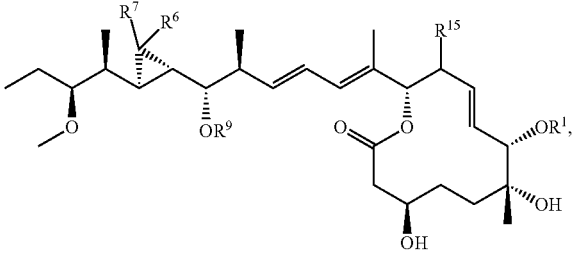

(VI)

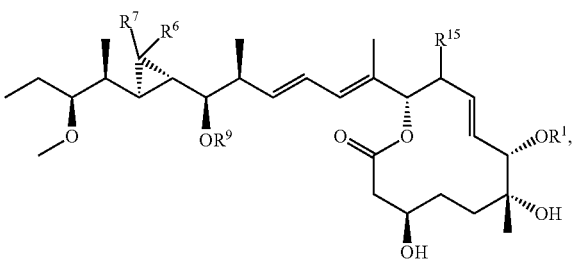

(VII)

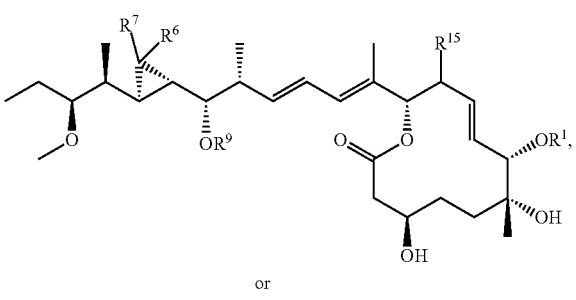

or (VIII)

R$^1$, R$^6$, R$^7$, and R$^{15}$ are as defined herein.

R$^1$ may be acetyl or hydrogen. R$^1$ may be acetyl. R$^{15}$ may be hydrogen or C$_1$-C$_4$ unsubstituted alkyl. R$^{15}$ may be C$_1$-C$_4$ unsubstituted alkyl. R$^{15}$ may be C$_1$-C$_4$ unsubstituted alkyne or C$_1$-C$_4$ alkene. R$^{15}$ may be methyl. R$^{15}$ may be hydrogen. R$^9$ may be hydrogen or C$_1$-C$_4$ unsubstituted alkyl. R$^9$ may be hydrogen. R$^9$ may be acetyl. X$^2$ may be C(R$^6$)(R$^7$), as exemplified by formula (V), (VI), (VII), or (VIII). R$^6$ and R$^7$ may independently be hydrogen, halogen, or methyl. R$^6$ and R$^7$ may both be hydrogen. R$^6$ and R$^7$ may both be fluoride.

When X$^2$ is C(R$^6$)(R$^7$), R$^2$ may be attached to a chiral carbon having (S) stereochemistry, and R$^4$ may be attached to a carbon having (S) or (R) stereochemistry. R$^2$ and R$^4$ may both be attached to a chiral carbon having (S) stereochemistry. The compound may have formula (V). When R$^2$ is attached to a carbon having (S) stereochemistry, R$^4$ may be attached to a carbon having (R) stereochemistry. The compound may have formula (VI). When X$^2$ is C(R$^6$)(R$^7$), and $R^2$ is attached to a chiral carbon having (R) stereochemistry, $R^4$ may be attached to a carbon having (S) or (R) stereochemistry. Both $R^2$ and $R^4$ may be attached to a chiral carbon having (R) stereochemistry. When $R^2$ is attached to a carbon having (R) stereochemistry and $R^4$ may be attached to a carbon having (S) stereochemistry. The compound may have formula (VIII).

The compound of formula (I) may have formula:

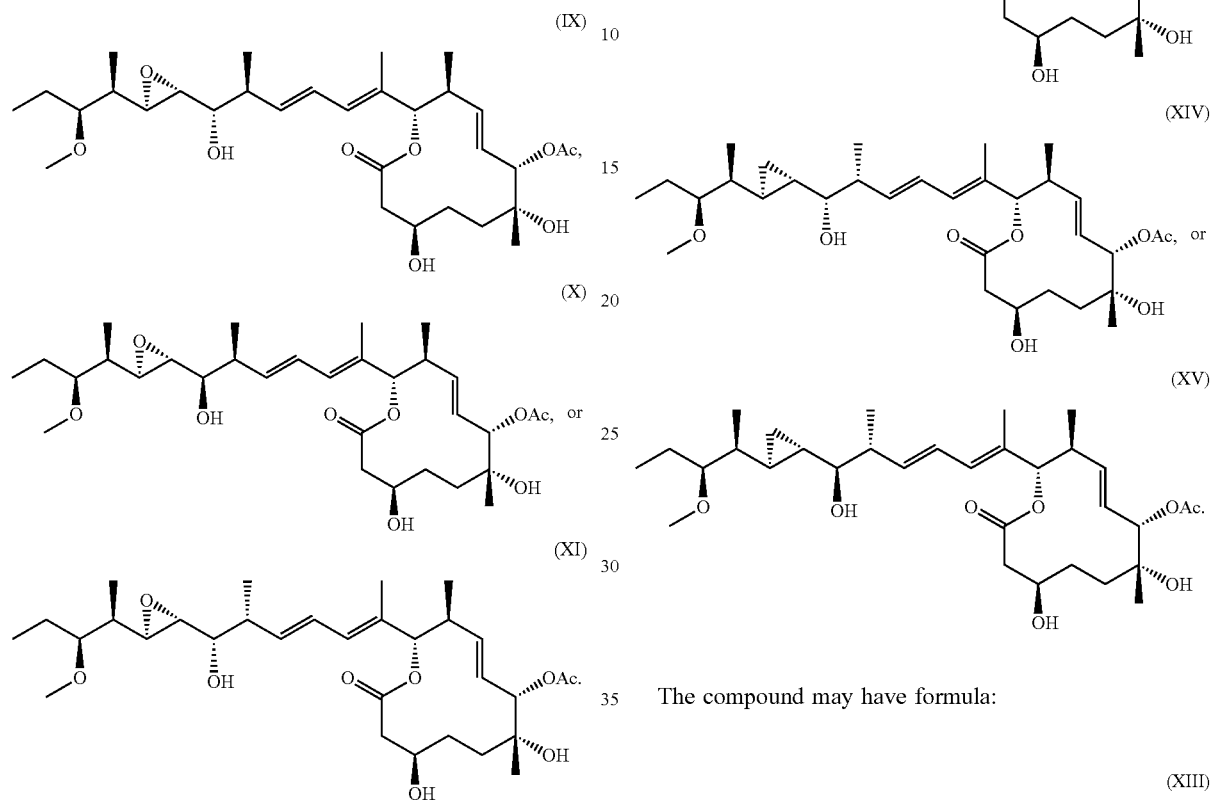

In another embodiment the compound of formula (I) has formula:

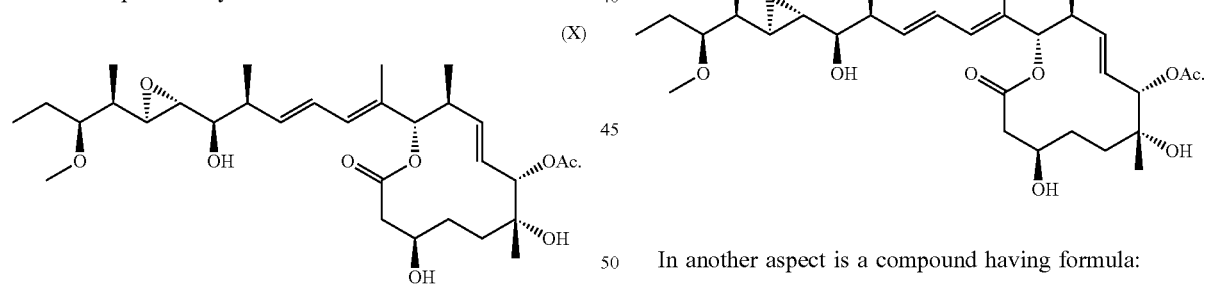

The compound may have formula:

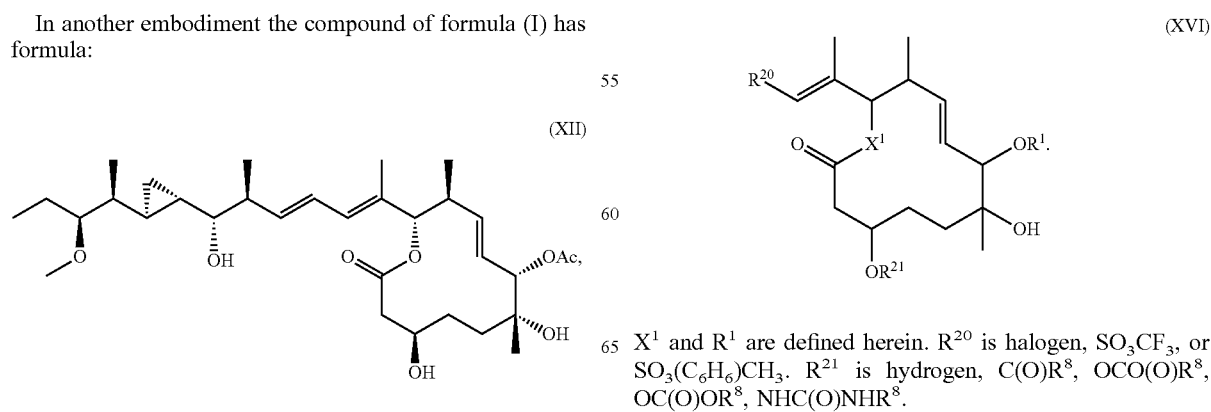

In another aspect is a compound having formula:

(XVI)

$X^1$ and $R^1$ are defined herein. $R^{20}$ is halogen, $SO_3CF_3$, or $SO_3(C_6H_6)CH_3$. $R^{21}$ is hydrogen, $C(O)R^8$, $OCO(O)R^8$, $OC(O)OR^8$, $NHC(O)NHR^8$.

The compound of formula (XVI) may have formula:

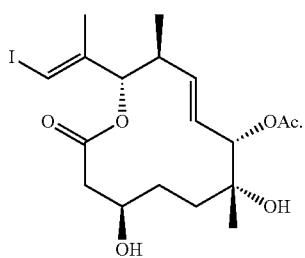
(XVIa)

In another aspect is a compound having formula:

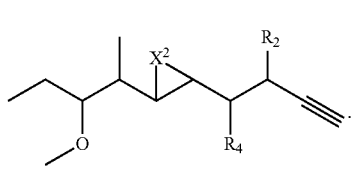
(XVII)

$X^1$, $R^2$, and $R^4$ are as defined herein.

$X^2$ may be O. In such instances, when $R^2$ is attached to a chiral carbon having (S) stereochemistry, $R^4$ may be attached to a carbon having (S) or (R) stereochemistry. When $R^2$ is attached to a carbon having (S) stereochemistry, $R^4$ may be attached to a carbon having (S) stereochemistry. When $R^2$ is attached to a carbon having (S) stereochemistry, $R^4$ may be attached to a carbon having (R) stereochemistry. In another embodiment, when $X^1$ is O, $R^2$ is attached to a chiral carbon having (R) stereochemistry, and $R^4$ is attached to a carbon having (S) stereochemistry. $R^2$ and $R^4$ may be methyl.

Compound (XVII) may have formula:

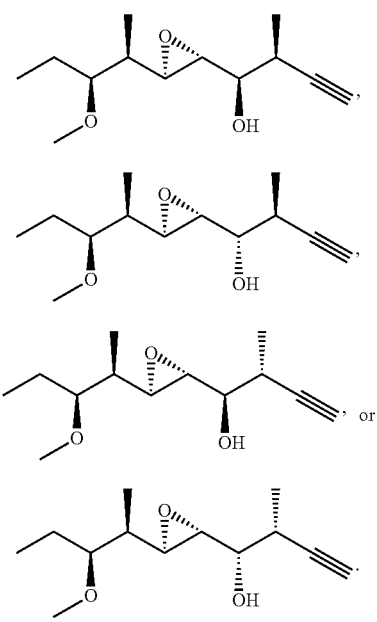
(XVIIa)
(XVIIb)
(XVIIc)
(XVIId)

In another embodiment, $X^2$ may be $C(R^6)(R^7)$. In such instances, $R^6$ and $R^7$ may independently be hydrogen, halogen, or methyl. Both $R^6$ and $R^7$ may be hydrogen. Both $R^6$ and $R^7$ may be fluoride. When $X^2$ is $C(R^6)(R^7)$, $R^2$ may be attached to a chiral carbon having (S) stereochemistry, and $R^4$ may be attached to a carbon having (S) or (R) stereochemistry. Both $R^2$ and $R^4$ may be attached to a chiral carbon having (S) stereochemistry. When $R^2$ is attached to a carbon having (S) stereochemistry, $R^4$ may be attached to a carbon having (R) stereochemistry. In another embodiment, when $R^2$ is attached to a chiral carbon having (R) stereochemistry, $R^4$ may be attached to a carbon having (S) or (R) stereochemistry. Both $R^2$ and $R^4$ may be attached to a chiral carbon having (R) stereochemistry. When $R^2$ is attached to a carbon having (R) stereochemistry and $R^4$ may be attached to a carbon having (S) stereochemistry. $R^2$ and $R^4$ may be methyl.

Compound (XVII) may have formula:

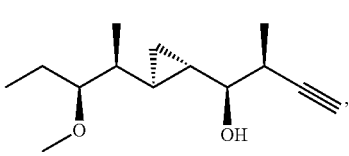
(XVIIe)

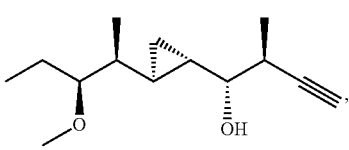
(XVIIf)

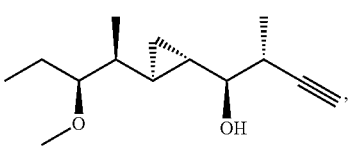
(XVIIg)

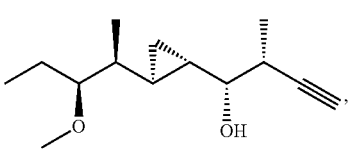
(XVIIh)

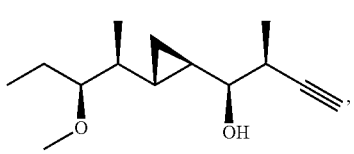
(XVIIi)

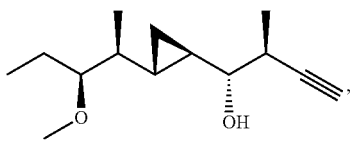
(XVIIj)

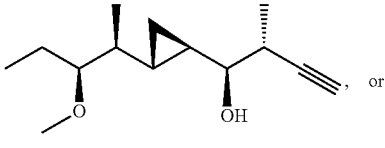
(XVIIk)

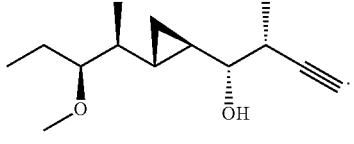
(XVIIl)

III. PHARMACEUTICAL COMPOSITIONS

In another aspect is provided a pharmaceutical composition. The composition includes a compound having formula (I), (II), (III), (IV), (V), (VI), (VII), or (VIII) and a pharmaceutically acceptable excipient. The compound may have formula (IX), (X), or (XI). Alternatively the compound may have formula (XII), (XIII), (XIV), or (XV). The pharmaceutical composition may include more than one compound having formula (I), (II), (III), (IV), (V), (VI), (VII), or (VIII). The pharmaceutical composition may contain dosages of the compounds in a therapeutically effective amount. The pharmaceutical composition may include one amount of a compound having formula (I), (II), (III), (IV), (V), (VI), (VII), or (VIII) and a second amount of a second compound having (I), (II), (III), (IV), (V), (VI), (VII), or (VIII). The pharmaceutical composition may include at least one compound having formula (IX), (X), (XI), (XII), (XIII), (XIV), or (XV). The pharmaceutical composition may include one amount of a compound having formula (IX), (X), (XI), (XII), (XIII), (XIV), or (XV) and a second amount of a second compound having formula (IX), (X), (XI), (XII), (XIII), (XIV), or (XV).

1. Formulations

The pharmaceutical composition may be prepared and administered in a wide variety of dosage formulations. Compounds having formula (I), (II), (III), (IV), (V), (VI), (VII), or (VIII) may be administered orally, rectally, or by injection (e.g. intravenously, intramuscularly, intracutaneously, subcutaneously, intraduodenally, or intraperitoneally).

For preparing pharmaceutical compositions from compounds having formula (I), (II), (III), (IV), (V), (VI), (VII), or (VIII), pharmaceutically acceptable carriers can be either solid or liquid. Solid form preparations include powders, tablets, pills, capsules, cachets, suppositories, and dispersible granules. A solid carrier may be one or more substance that may also act as diluents, flavoring agents, binders, preservatives, tablet disintegrating agents, or an encapsulating material.

In powders, the carrier may be a finely divided solid in a mixture with the finely divided active component. In tablets, the active component may be mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight. Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

The pharmaceutic composition may be intended for intravenous use. The pharmaceutically acceptable excipient can include buffers to adjust the pH to a desirable range for intravenous use. Many buffers including salts of inorganic acids such as phosphate, borate, and sulfate are known.

2. Effective Dosages

The pharmaceutical composition may include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat leukemia (e.g., chronic lyphocytic leukemia), such compositions will contain amounts of active ingredients effective to achieve the desired result (e.g. increasing the extent of cancer cell death in the patient).

The dosage and frequency (single or multiple doses) of compounds administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds disclosed herein.

For any compound described herein or combination thereof, the therapeutically effective amounts can be initially determined from cell culture assays. Target concentrations will be those concentrations of active compound(s) that are capable of increasing the extent of cancer cell death as measured, for example, using methods known in the art.

Therapeutically effective amounts for use in humans may be determined from animal models. For example, a dose for humans can be formulated to achieve a concentration that has been found to be effective in animals. The dosage in humans can be adjusted by monitoring response of the cancer to the treatment and adjusting the dosage upwards or downwards, as described above.

Dosages may be varied depending upon the requirements of the subject and the compound being employed. The dose administered to a subject, in the context of the pharmaceutical compositions presented herein, should be sufficient to effect a beneficial therapeutic response in the subject over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached.

Dosage amounts and intervals can be adjusted individually to provide levels of the administered compounds effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

3. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

When parenteral application is needed or desired, particularly suitable admixtures for the compounds included in the pharmaceutical composition may be injectable, sterile solutions, oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. Pharmaceutical admixtures suitable for use in the pharmaceutical compositions presented herein may include those described, for example, in Pharmaceutical Sciences (17th Ed., Mack Pub. Co., Easton, Pa.) and WO 96/05309, the teachings of both of which are hereby incorporated by reference.

IV. METHODS

1. Methods of Treating Cancer

In another aspect a method of treating cancer is provided. The method includes administering to a subject in need thereof, a therapeutically effective amount of a compound of formula (I), (II), (III), (IV), (V), (VI), (VII), or (VIII). The compound may be co-administered with a pharmaceutically acceptable excipient, as addressed in previous sections. The cancer may be leukemia, lymphoma, metastatic cancer or bone cancer. The cancer may be leukemia or lymphoma. The cancer may be chronic lyphocytic cancer (CLL).

2. Methods of Detecting Spliceosome Inhibition

In another aspect, a method of detecting spliceosome inhibition using a test compound is provided. The method includes contacting a cell with the test compound, extracting an mRNA from the cell to produce an extracted mRNA, reverse transcribing the mRNA using intron-specific primers to form an intron cDNA, amplifying the intron cDNA to form a plurality of amplified intron cDNA's, and detecting the presence of the amplified intron cDNAs to detect spliceosome inhibition resulting from the test compound.

The extracting step may include lysing the cell. The lysing may be performed using techniques such as but not limited to sonication, freeze-thaw cycling, or French pressing. It is understood that any method which disrupts the cell membrane is appropriate. In certain embodiments the intron-specific primers are primers for DNAJBG1, or RIOK3. The method may include using a control primer to form a control cDNA. The control primer may form a complement with a sequence not affected by the spliceosome. In certain embodiments the intro-specific primers are set forth in Table 1.

TABLE 1

Sequence of Primers used in RT-PCR and qRT-PCR experiments:

| Probe | Location | RT-PCR Sequence | RT-PCR Sequence |
|---|---|---|---|
| DNAJAB1-FW | Exon 2 | 5'gaaccaaaatcacttccccaaggaagg3' (SEQ ID NO: 1) | 5'ggcctgatgggtcttatctatgg3' (SEQ ID NO: 2) |
| DNAJB1-RV | Exon 3 | 5'aatgaggtccccacgtttctcgggtgt3' (SEQ ID NO: 3) | 5'ttagatggaagctggctcaagag3' (SEQ ID NO: 4) |
| RIOK3-FW | Exon 3 | 5'gctgaaggaccatttattactggag3' (SEQ ID NO: 5) | 5'tcaatggagatagcaaaggtattataac3' (SEQ ID NO: 6) |
| RIOK3-RV | Exon 4 | 5'ttcttgctgtgttctttctcccaca3' (SEQ ID NO: 7) | 5'agatttactaggagcacattatgagtg3' (SEQ ID NO: 8) |
| GAPDH-FW | | 5'tggtcaccagggctgctt3' (SEQ ID NO: 9) | 5'tggtcaccagggctgctt3' (SEQ ID NO: 10) |
| GAPDH-RV | | 5'agcttcccgttctcagcctt3' (SEQ ID NO: 11) | 5'agcttcccgttctcagcctt3' (SEQ ID NO: 12) |

The test compound may be a compound having formula (I), (II), (III), (IV), (V), (VI), (VII), or (VIII). The test compound may be a compound having formula (XI), (X), or (XI). The test compound may be a compound having formula (XII), (XIII), (XIV), or (XV).

The reverse transcribing may be done using PCR. The amplification may further include forming a plurality of amplified complementary intron cDNAs. The detection step may detect the presence of the amplified complementary intron cDNAs. The detection step may detect the presence of both the amplified intron cDNAS and the amplified complementary intron cDNAs. The detection step may detect the presence of either the amplified intron cDNAs or the amplified complementary intron cDNAs. The detection step may be performed following purification of the amplified intron cDNAs or following purification of the amplified complementary cDNAs. The detection step may be performed without any purification step prior to the detection. In certain embodiments the detecting further includes determining an amount of the plurality of amplified intron cDNAs, based on the amount, determining a level of the mRNA within the sample, and comparing the level to a standard control level. An elevated level of the mRNA relative to the control level may indicate that the test compound interferes with splicing and targets the spliceosome. The detection of an amount of cDNAs may be performed for amplified complementary intron cDNAs. The detection of an amount of cDNAs may be performed for both amplified intron cDNAs and amplified complementary intron cDNAs.

The method of detecting spliceosome inhibition using a test compound may include using a cell derived from a cancer patient. The cell may be obtained through biopsy. The cell may be from a cancer patient having leukemia, lymphoma, metastatic cancer, or bone cancer. The cell may be from a cancer patient having chronic lyphocytic leukemia (CLL). The cell may be a cancer cell line. The cancer cell line may be RAJI, Jurkat, or MEC1.

V. EXAMPLES

Example 1

Synthesis of Component A, aldehyde 8.

Scheme 1: Construction of side chain component A, aldehyde 8, in 13 steps.

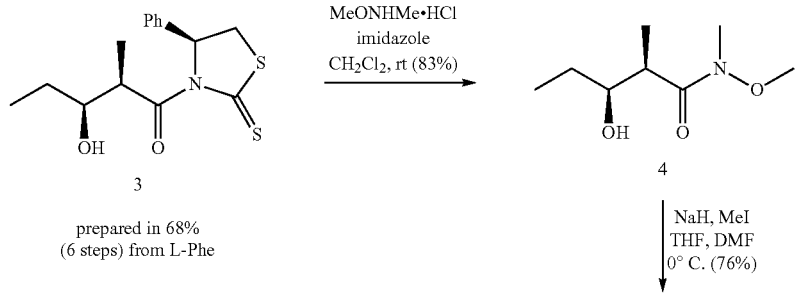

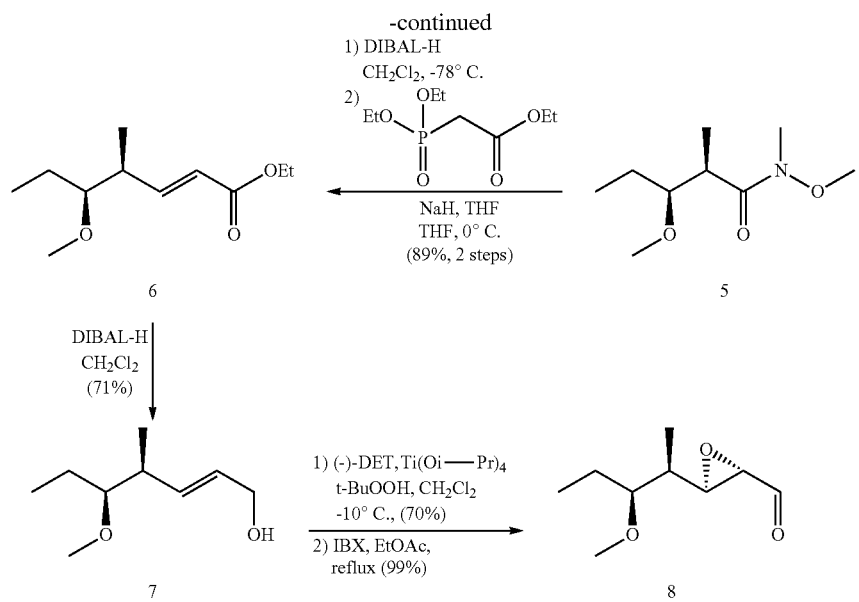

Figure 2:
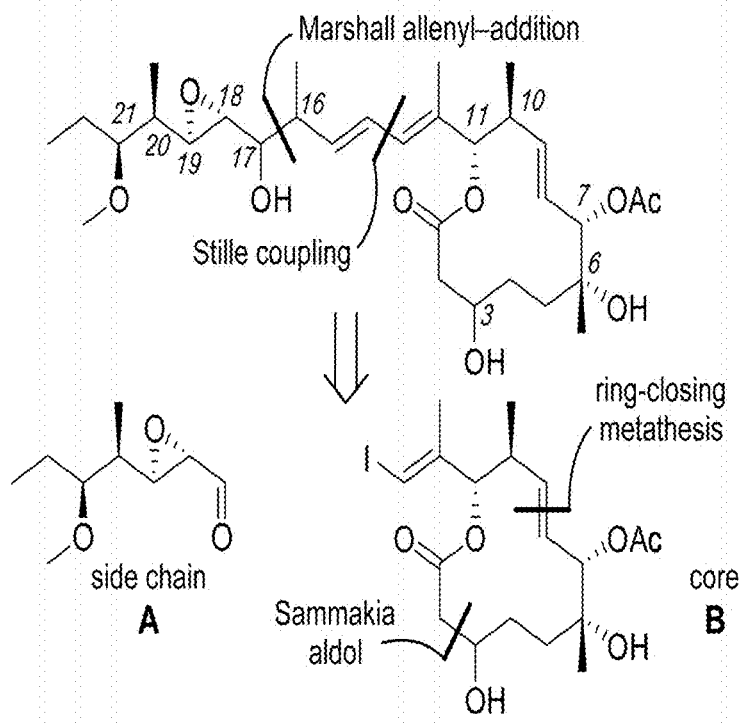
FIG. 2: Retrosynthetic analysis for preparation of cis- and trans-isomers 1RS, 1SR, 1RR and 1RR respectively showing, late-staged Marshall allenyl-addition and Stille coupling sequence provide the disconnections to components Side chain A and core macrolide B.

Synthesis of side component A, aldehyde 8 is shown in Scheme 1. (See FIG. 2). Briefly, application of a Crimmins auxiliary set the C20-C21 stereodiad by providing adduct 3 with ~5:1 de, which was chromatographically purified to provide 3. Conversion of 3 to Weinreb's amide 4 allowed methylation provided amide 5. Reduction of 5 with DIBAL-H, followed by a Homer-Wadsworth-Emmons (HWE) olefination, provided ester 6. The HWE reaction was completed immediately after isolation of the aldehyde. Exhaustive reduction of 6 with DIBAL-H provided intermediate alcohol 7. Aldehyde 8 was synthesized through installation of the C18-C19 epoxide by a Sharpless oxidation, following IBX oxidation.

Example 2

Synthesis of Component B, macrolide 21

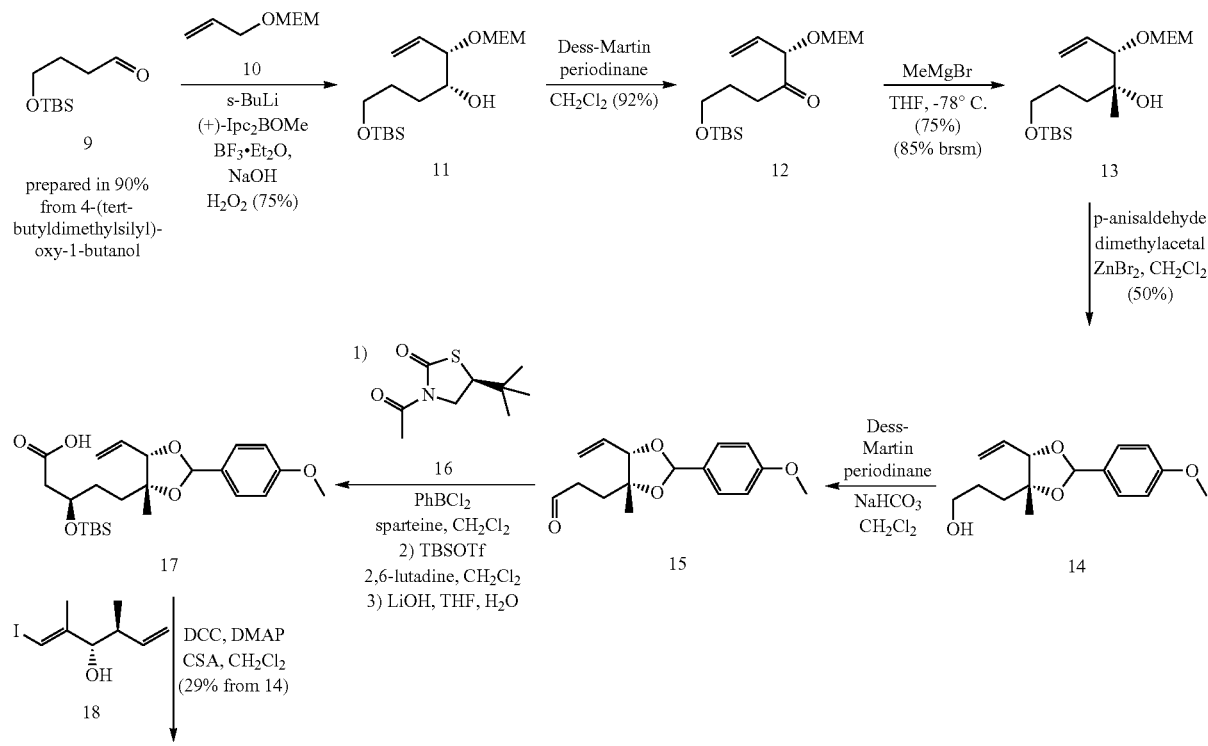

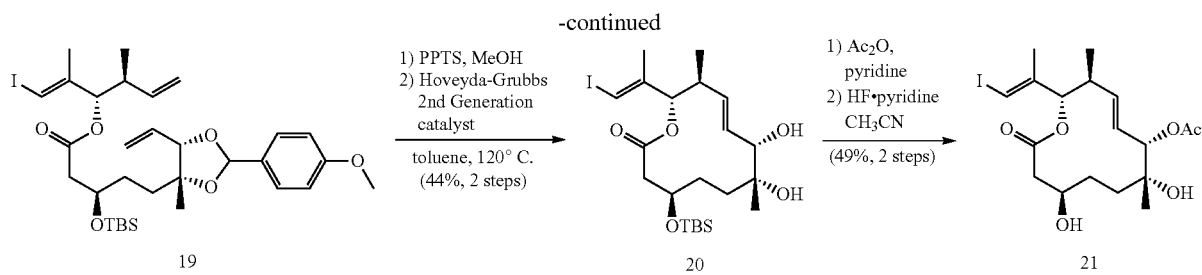

Synthesis of component B, macrolide 21 is shown in Scheme 2. (See FIG. 2). Brown chelation-controlled addition of the MEM ether 10 to aldehyde 9 provided the C7 stereocenter in 11. Oxidation of 11 to ketone 12, followed by a chelate-controlled addition of MeMgBr, afforded adduct 13. Treatment of MEM ether with p-anisaldehyde dimethylacetal and $ZnBr_2$ both converted the MEM ether to PMP acetal and deprotected the TBS ether in one operation, affording carbinol 14.

Oxidation of 14 to aldehyde 15 using Dess-Martin periodinane, followed by condensation with the Sammakia auxiliary 16, provided acid 17 after hydrolytic workup. Acid 17 was coupled to alcohol 18 to afford ester 19. Removal of the PMP acetal enabled the preparation of lactone 20 by means of an RCM reaction using Hoveyda-Grubbs 2nd generation catalyst. Macrolide 21 was obtained by acylation of the secondary carbinol at C7 and TBS deprotection at C3.

Example 3

Preparation of cis-isomers 1RS and 1SR.

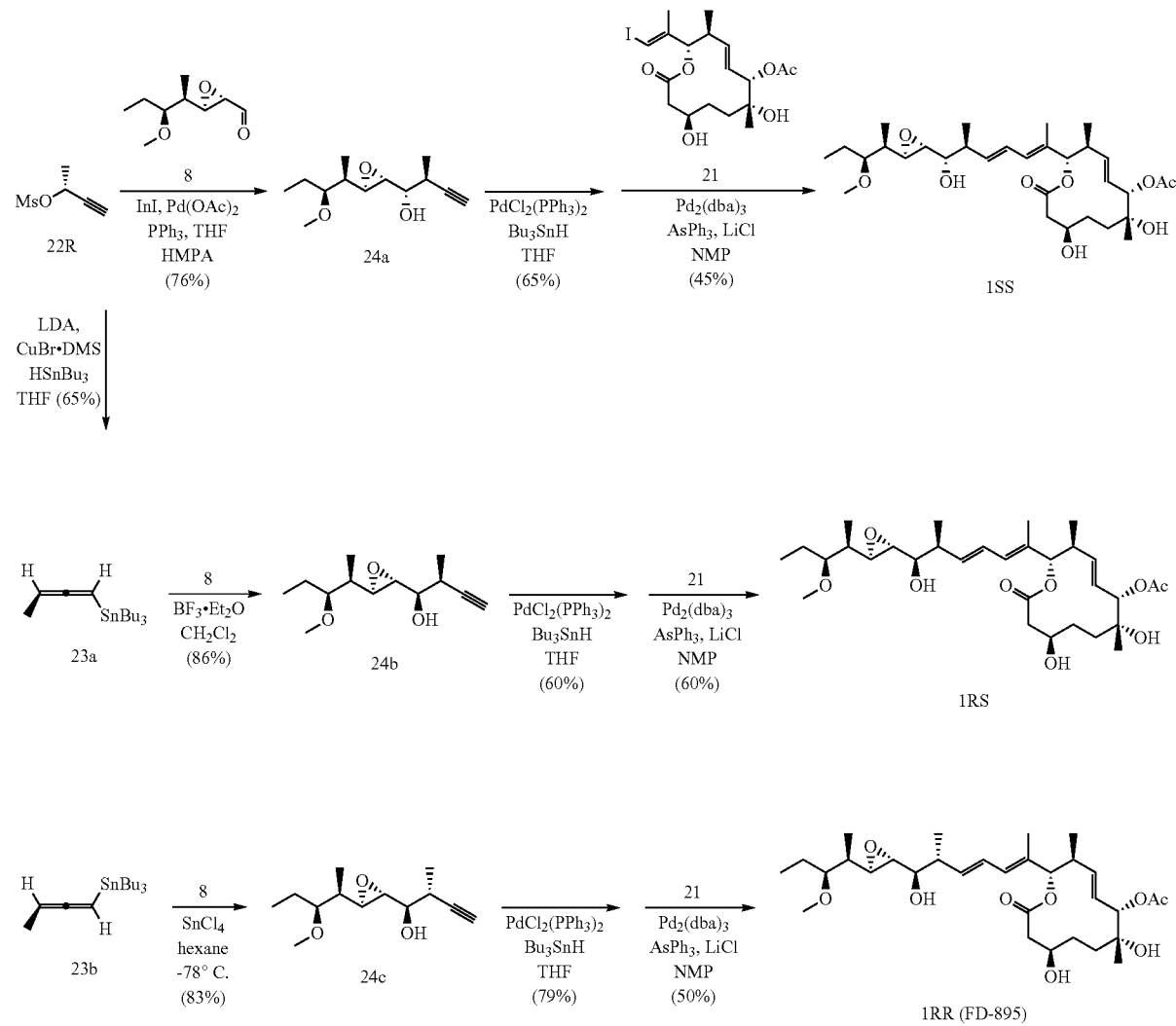

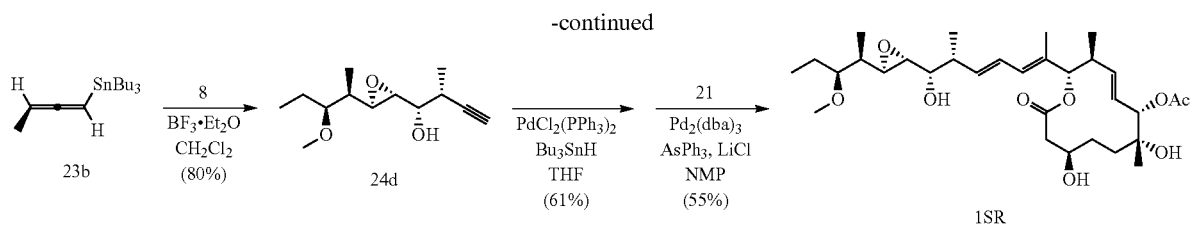

Figure 3:
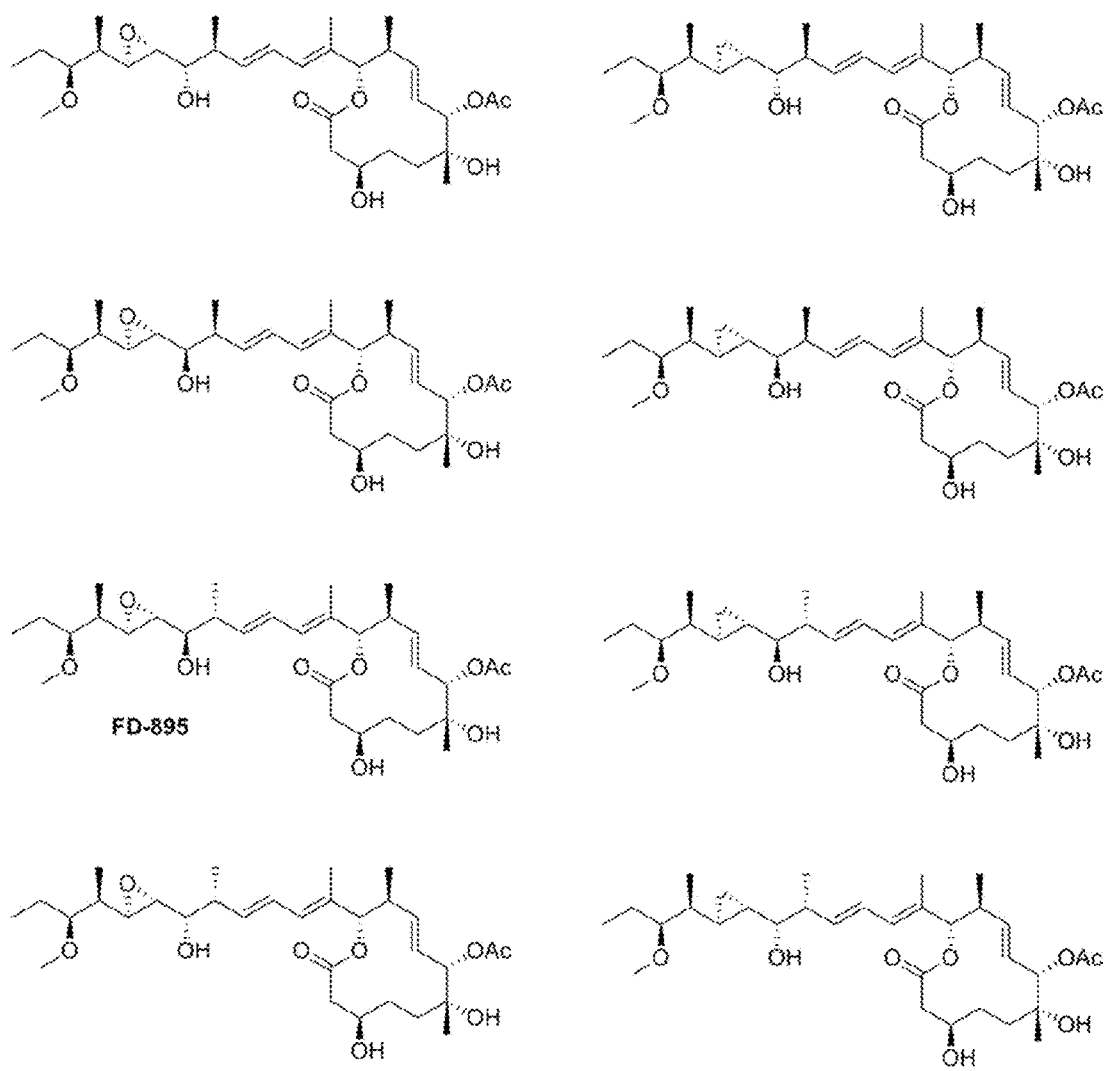
FIG. 3: Epoxide and cyclopropane synthetic derivatives of FD-895.

Synthesis of cis- and trans-isomers 1SS, 1RS, 1RR, and 1SR is shown in Scheme 3. (See FIG. 2). Addition of terminal alkynes 23a or 23b to aldehyde 8 in the presence of $BF_3 \cdot Et_2O$ led to the formation of 24b or 24d, respectively. Alkynes 24b and 24d were then hydrostannylated to their corresponding vinylstannanes and coupled to core fragment 21 under modified Stille conditions to afford the cis-isomers 1RS and 1SR from 24b and 24d, respectively. NMR studies on both materials indicated that neither matched the natural 1RR (FD-895) analogue (FIG. 3).

Example 4

Preparation of the trans-isomers 1SS and 1RR. Using a mixture of InI and $Pd(OAc)_2$, alkyne 24a was provided from aldehyde 8 as a single product. Hydrostannylation and Stille coupling to 21 afforded trans-isomer 1SS (Scheme 3). NMR data collected from 1SS (FIG. 3) did not match the natural 1RR (FD-895) analogue 1 Treating 23a and 8 with $SnCl_4$ at −78° C. in hexane provided 24c. Hydrostannylation and Stille coupling of 24c afforded the final isomer 1RR whose $^1H$ NMR spectral data matched that of natural analogue FD-895 (FIG. 3).

Example 5

Figure 4:
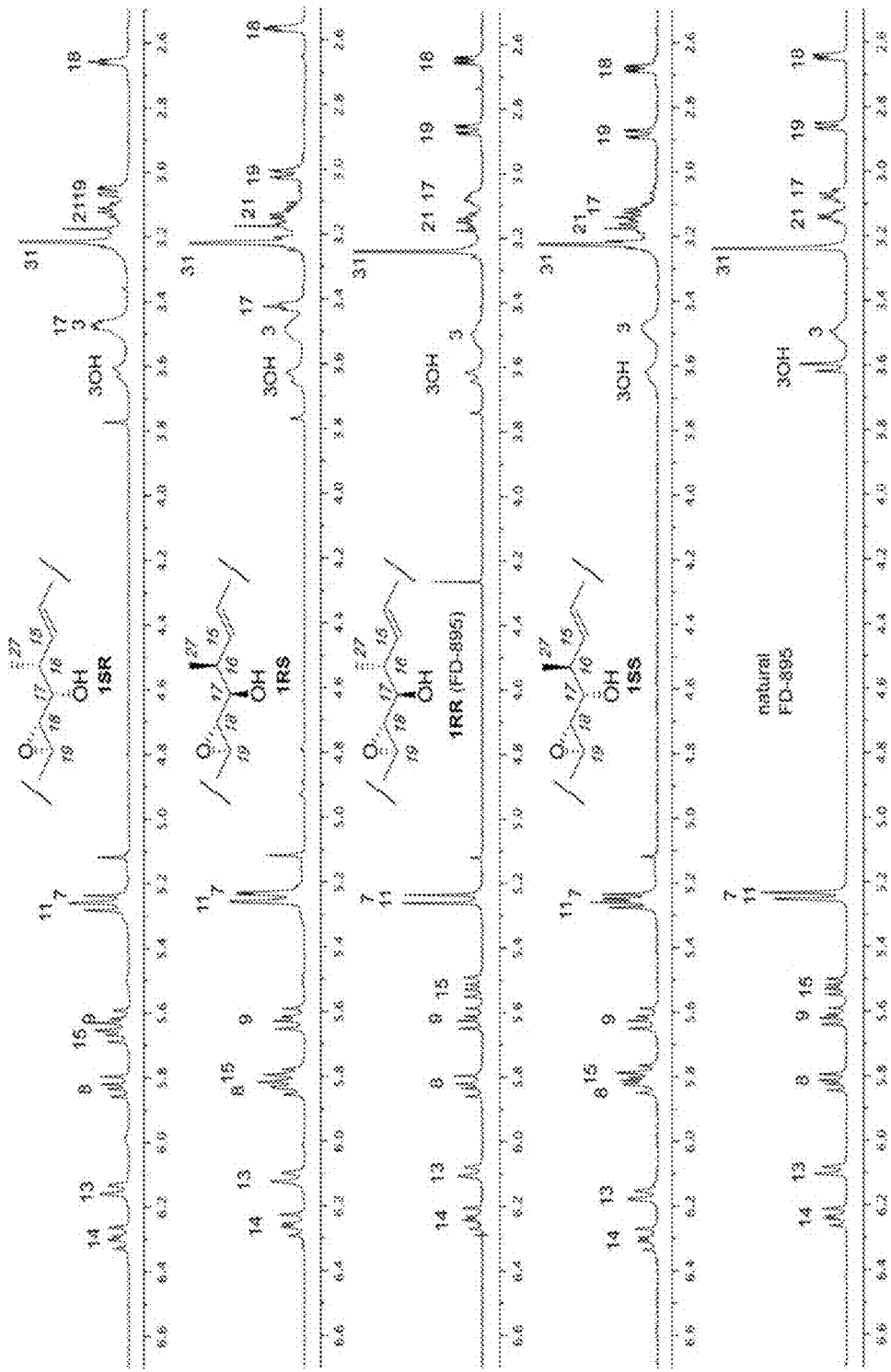
FIG. 4: $^1$H NMR spectra of synthetic isomers 1SR, 1RS, 1RR, 1SS and the $^1$H NMR spectra of the natural FD-895 (1) compound.

Structure Activity Relationships (SAR) studies for 1SS, 1RR, 1RS, and 1RR. It has been reported that ablation of C3, C6 and C7 substituents is detrimental to activity. Application of the MTT cell proliferation assay to 1SS, 1RS, 1RR and 1SR indicated that all four isomers displayed sub-nM to nM activity when examining the HCT-116 cell line ($IC_{50}$ value of 23.0±1.2 nM for 1SS, 0.80±0.05 nM for 1RS, 24.2±0.9 nM for 1RR, and 3.7±0.2 nM for 1SR). While the activity for 1RR matched that of naturally isolated FD-895 ($IC_{50}$ value of 23.5±0.2 nM), isomers with the natural R-configuration at C16 were less active than the synthetic analogs bearing S at C16. (See FIG. 4). Additional activity was also observed when C17 was left in its natural R configuration. Isomer 1RS was nearly 25 times more active than FD-895, providing a strong foundation for isomer 1RS as a clinically-relevant synthetic analog.

Example 6

General experimental methods: Chemical reagents were purchased from Acros, Fluka, Sigma-Aldrich, or TCI. Deuterated NMR solvents were purchased from Cambridge Isotope Laboratories. All reactions were conducted with rigorously dried anhydrous solvents that were obtained by passing through a solvent column composed of activated Al alumina Anhydrous N,N-dimethylformamide was obtained by passage over activated molecular sieves and a subsequent NaOCN column to remove traces of dimethylamine Triethylamine (Et3N) was dried over Na and freshly distilled. Ethyl-N,N-diisopropylamine (EtNiPr2) was distilled from ninhydrin, then from potassium hydroxide. Anhydrous CH3CN was obtained by distillation from CaH2. All reactions were performed under positive pressure of Ar in oven-dried glassware sealed with septa, with stirring from a Teflon coated stir bars using an IKAMAG RCT-basic mechanical stirrer (IKA GmbH). Solutions were heated using either a sand or silicon oil bath. Analytical Thin Layer Chromatography (TLC) was performed on Silica Gel 60 F254 precoated glass plates (EM Sciences). Preparative TLC (pTLC) was conducted on Silica Gel 60 plates (EM Sciences). Visualization was achieved with UV light and/or an appropriate stain (I2 on SiO2, KMnO4, bromocresol green, dinitrophenylhydrazine, ninhydrin, and ceric ammonium molybdate). Flash chromatography was carried out Geduran Silica Gel 60 (40-63 mesh) from EM Biosciences.

Yields and characterization data correspond to isolated, chromatographically and spectroscopically homogeneous materials. 1H NMR spectra were recorded on Varian Mercury 300, Varian Mercury 400 spectrometers, Varian Mercury Plus 400, a JEOL ECA500, or a Varian VX500 spectrometer. A majority of the 13C NMR spectra were recorded at 125 MHz on a Varian VX500 spectrometer equipped with an XSens Cold probe. The remaining spectra were either collected at 125 MHz on a JEOL ECA 500, 100 MHz on a Varian Mercury 400 or 100 MHz on a Varian Mercury Plus 400 spectrometer. Chemical shifts for 1H NMR and 13C NMR analyses were referenced to the reported values of Gottlieb, 1 using the signal from the residual solvent for 1H spectra, or to the 13C signal from the deuterated solvent. Chemical shift δ values for 1H and 13C spectra are reported in parts per million (ppm) relative to these referenced values, and multiplicities are abbreviated as s=singlet, d=doublet, t=triplet, q=quartet, m=multiplet, br=broad. All 13C NMR spectra were recorded with complete proton decoupling. FID files were processed using Mestrallova 6.0.2. (MestreLab Research). Electrospray (ESI) mass spectrometric analyses were performed using a ThermoFinnigan LCQ Deca spectrometer, and high-resolution analyses were conducted using a ThermoFinnigan MAT900XL mass spectrometer with electron impact (EI) ionization. A Thermo Scientific LTQ Orbitrap XL mass spectrometer was used for high-resolution electrospray ionization mass spectrometry analysis (HR-ESI-MS). FTIR spectra were obtained on a Nicolet magna 550 series II spectrometer as thin films on either KBr or NaCl discs, and peaks are reported in wavenumbers (cm-1). Optical rotations $[\alpha]_D$ were measured using a Perkin-Elmer Model 241 polarimeter with the specified solvent and concentration and are quoted in units of deg cm2 g-1. Spectral data and procedures are provided for all new compounds and copies of select spectra have been provided.

Example 7

Gram scale synthesis of side chain component 8. Component 8 was prepared in 13 steps in 19% yield from L-phenylalanine as shown in Scheme 1 (in the manuscript) and Scheme S1 (below). The following section provides a complete description of the synthetic procedures and spectroscopic properties of each intermediate.

Conversion to auxiliary S2 involved a three-step procedure described by Le Corre.3 The following procedure was conducted without purification of the intermediates with the entire crude product carried on at each stage. Triethylamine

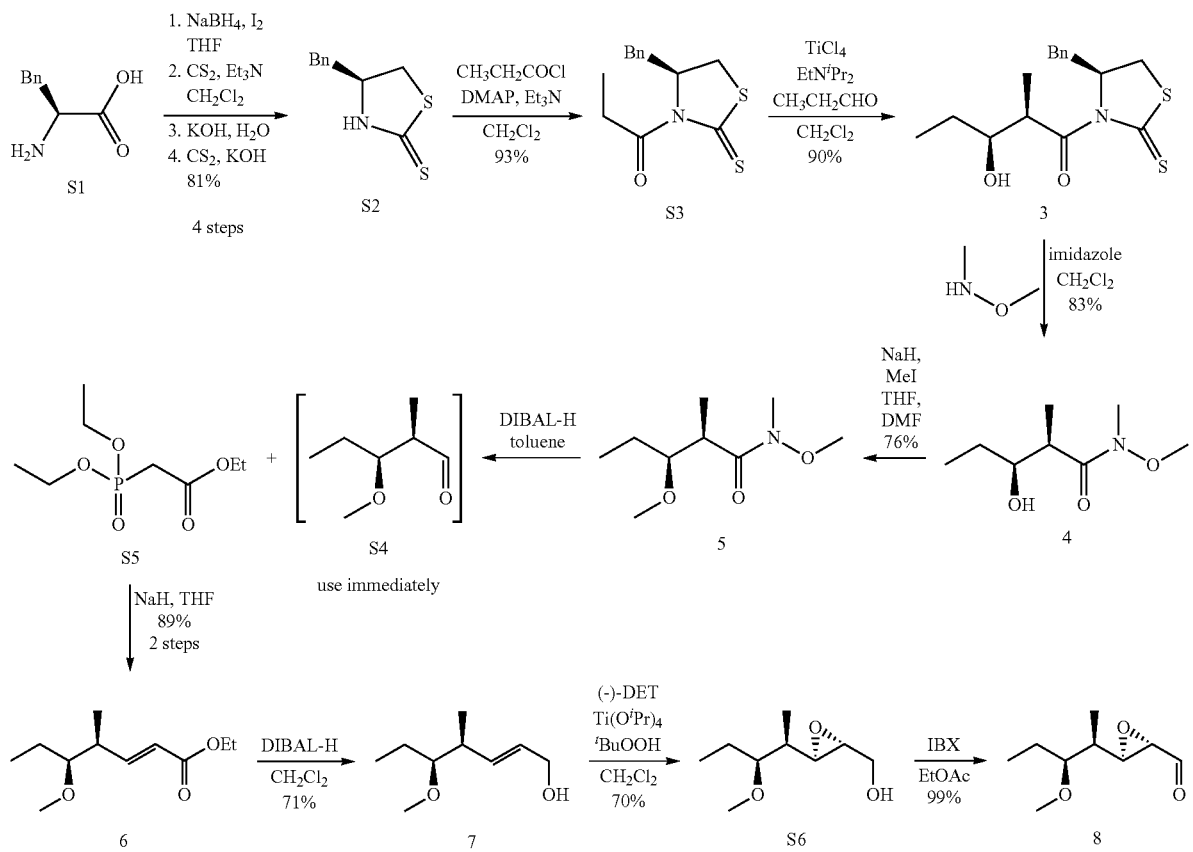

Scheme S1. Gram scale synthesis of component 8.

Example 8

(S)-4-benzylthiazolidine-2-thione (S2). A four-step procedure was used following literature precedent beginning with reduction of L-phenylalanine.2 All four steps were conducted in a 22 L heavy walled three-neck flask equipped with a RW-16 overhead stirrer (IKA GmbH), reflux condenser and an addition funnel. The flask was charged with NaBH4 (113.49 g, 3 mol) and 3 L THF and charged with an Ar atmosphere. L-Phenylalanine (198.2 g, 1.2 mol) was added and the mixture was cooled to 0° C. A solution of iodine (303.8 g, 1.2 mol) in 0.7 L THF was added dropwise via an addition funnel over a period of 45 min. After a decreasing gas evolution the mixture was heated to reflux for 18 h. The flask was cooled to 0° C. and MeOH (0.8 L) was added cautiously until the mixture became a clear solution. The resulting solution slowly warmed to rt over 1 h and stirred at rt further 45 min. The solvent was removed under reduced pressure and the white residue was dissolved in 2.5 L of 20% aq. KOH and stirred at rt for 4 h. The reaction mixture was extracted with CH2Cl2 (3 #2 L) and dried over Na2SO4, and concentrated on a rotary evaporator. Dry Column Vacuum Chromatography (DCVC) using a 1 kg plug of SiO2 and washing with EtOAc (1 L) afforded (S)-2-amino-3-phenylpropan-1-ol (S1) (181.2 g, 1.19 mol, 99%).

(200 mL, 1.43 mol) was added to an ice-cooled solution of compound S1 (181.2 g, 1.19 mol) and CS2 (87.4, 1.43 mol) in CH2Cl2 (2.5 L). The mixture was refluxed overnight and washed with 1N HCl (3×0.8 L). The organic layers were combined, dried with Na2SO4 and evaporated to afford the corresponding dithiocarbamic acid, which was used without further purification.

A solution of NaOH (48.5 g, 1.21 mol) in H2O (200 mL) was added to a solution of the crude dithiocarbamic acid dissolved THF (500 mL). The mixture was refluxed for 1 h and then neutralized to pH 7 by addition of 1N HCl. The resulting solution was extracted with CH2Cl2 (3 #1 L). The organic layers were combined, dried over Na2SO4, flushed with 1:1 hexanes/EtOAc through a plug of SiO2 (800 g) and concentrated via rotary evaporation to afford the corresponding oxazolidinethione.

The crude oxazolidinethione was dissolved in CS2 (364.0 mL, 5.95 mol) and aqueous 1N KOH (5.95 L) was added. The mixture was warmed to 100° C. After stirring at 100° C. for 16 h, the mixture was cooled to rt and was extracted with CH2Cl2 (3×3 L). The organic layers were combined, dried over Na2SO4, flushed with 1:1 hexanes/EtOAc (2 L) through a plug of SiO2 (800 g), and concentrated via rotary evaporation to afford a crude product. Pure S2 (201.5 g, 81%) was obtained by flash chromatography eluting with a gradient of hexanes to 1:1 hexanes/EtOAc.

Auxilary S2: TLC (1:1 hexanes/EtOAc): Rf=0.31; 1H NMR (CDCl3, 500 MHz) δ 8.36 (bs, 1H), 7.32 (m, 2H), 7.26 (m, 1H), 7.18 (m, 2H), 4.46 (dd, J=7.5, 15.0 Hz, 1H), 3.50 (dt, J=7.9, 11.5 Hz, 1H), 3.25 (dt, J=7.2, 11.5 Hz, 1H), 3.04 (m, 1H), 2.93 (m, 1H); 13C NMR (CDCl3, 125 MHz) δ 200.5, 135.7, 129.0, 128.9, 127.2, 65.1, 39.7, 37.8; FTIR (film) vmax 3154, 1602, 1495, 1437, 1327, 1297, 1279, 1233, 1204, 1040, 1008, 957, 743 cm-1; HR-ESI-MS m/z calcd. For C10H11NS2 [M]+: 209.0333. found 209.0342.

Example 9

(S)-1-(4-benzyl-2-thioxothiazolidin-3-yl)-propan-1-one (S3). Acylation of S2 was ideally conducted in batches at the 0.075±0.025 mol scale using a conventional RCT basic stir plates (IKA GmbH). An exemplary procedure was as follows: compound S2 (17.5 g, 0.084 mol) was dissolved in CH2Cl2 (400 mL). Et3N (14.0 mL, 0.10 mol) and 4-dimethylaminopyridine (DMAP, 2.0 g, 0.017 mol) were added sequentially. Freshly distilled propionyl chloride (9.5 mL 0.11 mol) in CH2Cl2 (100 mL) added dropwise over 1 h. After stirring at rt for 3 h, satd. NH4Cl (100 mL) was added and the mixture was extracted with CH2Cl2 (3 #200 mL). The organic layers were combined, washed with satd. NaHCO3 (100 mL) and brine (100 mL), dried with Na2SO4, and concentrated on a rotary evaporator. Recrystallization from CH3CN afforded pure S3 (20.7 g, 94%). Over 12 batches, yields were observed in the range of 93±2%.

Acylated auxilary S3: TLC (1:1 hexanes/EtOAc): Rf=0.62; 1H NMR (CDCl3, 500 MHz) δ 7.33 (m, 2H), 7.27 (m, 3H), 5.37 (ddd, J=3.8, 7.3, 10.9 Hz, 1H), 3.41 (m, 2H), 3.20 (dd, J=3.7, 13.2 Hz, 1H), 3.11 (qd, J=7.1, 18.1 Hz, 1H), 2.87 (d, J=11.5 Hz, 1H), 1.18 (t, J=7.2 Hz, 3H); 13C NMR (CDCl3, 125 MHz) δ 201.1, 175.0, 136.6, 129.5, 128.9, 127.2, 68.7, 36.8, 32.4, 32.0, 8.9; FTIR (film) vmax 2979, 2933, 1695, 1602, 1488, 1455, 1378, 1322, 1265, 1133, 1034, 952, 951, 849, 760 cm-1; HR-ESI-MS m/z calcd. for C13H15NOS2 [M]+: 265.0595. found 265.0601.

Example 10

(2R,3S)-4-(S)-4-benzyl-2-thioxothiazolidin-3-yl)-3-hydroxy-2-methylpentan-1-one (3). The Crimmin's aldol reaction used to prepare 3 was ideally conducted at the 0.5±0.1 mol scale by stirring with a RCT basic stir plate (IKA GmbH). Larger scale reactions required use of overhead-stirred reactor as efficient mixing was critical to this step. An exemplary procedure is as follows: acylated auxiliary S3 (14.2 g, 0.054 mol) was dissolved in CH2Cl2 (430 mL). After cooling to 0° C., TiCl4 (6.2 mL, 0.056 mmol) was added over 5 min. EtNiPr2 (10.3 mL, 0.059 mol) was added. The mixture was stirred for 15 min at 0° C. and then cooled to −78° C. Propional (4.6 mL, 0.060 mol) was added and the mixture was warmed to 0° C. over 2 h. Satd. NaHCO3 (100 mL) was added cautiously and then extracted with CH2Cl2 (3×300 mL). The organic layers were combined, washed with satd. brine (100 mL), dried with Na2SO4, and concentrated on a rotary evaporator. Flash chromatography with a gradient from hexanes to 1:1 hexanes/EtOAc afforded pure 3 (15.58 g, 90%).

Adduct 3: TLC (1:1 hexanes/EtOAc): Rf=0.41; 1H NMR (CDCl3, 500 MHz) δ 7.33 (m, 2H), 7.27 (m, 3H), 5.36 (ddd, J=4.1, 7.2, 10.8 Hz, 1H), 4.63 (qd, J=2.0, 7.1 Hz, 1H), 3.97 (m, 1H), 3.36 (dd, J=7.2, 11.5 Hz, 1H), 3.24 (dd, J=4.0, 13.2 Hz, 1H), 3.04 (dd, J=10.4, 13.1 Hz, 1H), 2.88 (d, J=11.6 Hz, 1H), 2.79 (d, J=2.9 Hz, 1H), 1.61 (m, 1H), 1.45 (m, 1H), 1.18 (d, J=7.1 Hz, 3H), 0.97 (t, J=7.4 Hz, 3H); 13C NMR (CDCl3, 125 MHz) δ 201.6, 178.6, 136.5, 129.5, 129.0, 127.3, 72.6, 69.0, 42.3, 37.0, 31.9, 26.7, 10.6, 10.5; FTIR (film) vmax 3444, 3027, 2964, 2937, 2876, 1689, 1455, 1352, 1258, 1191, 1164, 1041, 1029, 960 cm-1; HR-ESI-MS m/z calcd. For C16H21NO2S2 [M]+: 323.1014. found 323.1143.

Example 11

(2R,3S)-3-hydroxy-N-methoxy-N,2-dimethylpentanamide (4). Adduct 3 (32.0 g, 0.10 mol) was dissolved in CH2Cl2 (1.45 L). Imidazole (19.3 g, 0.30 mol) and N, O, dimethylhydroxylamine HCl (19.3 g, 0.20 mol) was added. After stirring at rt for 6 h, 1 M HCl was added until the pH neutral (pH 7) and the mixture was extracted with CH2Cl2 (3×300 mL). The organic layers were combined, washed with satd. brine (100 mL), dried with Na2SO4, and concentrated on a rotary evaporator. Flash chromatography with a gradient from 1:1 hexanes/CH2Cl2 to 1:1 hexanes/EtOAc afforded pure 4 (14.37 g, 83%).

Amide 4: TLC (1:2 hexanes/EtOAc): Rf=0.35; 1H NMR (CDCl3, 500 MHz) δ 3.65 (bs, 1H), 3.61 (ddd, J=3.7, 5.3, 8.8 Hz, 1H), 3.58 (s, 3H), 3.06 (s, 3H), 2.70 (bs, 1H), 1.42 (m, 1H), 1.28 (m, 1H), 1.03 (d, J=7.1 Hz, 3H), 0.83 (t, J=7.5 Hz, 3H); 13C NMR (CDCl3, 125 MHz) δ 178.1, 73.0, 61.4, 38.4, 31.7, 26.8, 10.3, 10.2; FTIR (film) vmax 2969, 2917, 2855, 1719, 1449, 1265, 1178, 1108, 1020, 715 cm-1; HR-ESI-MS m/z calcd. for C8H17NO3 [M]+: 175.1208. found 175.1310.

Example 12

(2R,3S)—N,3-dimethoxy-N,2-dimethylpentanamide (5). Amide 4 (12.0 g, 0.068 mol) was dissolved in THF (480 mL) and DMF (120 mL). Methyliodide (61.2 mL, 1.37 mol) was added. The flask was purged with Ar and cooled to 0° C. NaH (6.8 g, 0.171 mol) was added slowly in portions as a mixture of 60% in oil. Care was taken to avoid too rapid evolution of H2. At all times a strict Ar atmosphere was maintained. The mixture was stirred at 0° C. for 2.5 h at which time TLC analysis indicated complete conversion. A solution of phosphate buffered saline pH 7 (120 mL) was added dropwise at 0° C. Care must be taken due to the vigorous reaction with the excess NaH. After the addition was complete, the mixture was extracted with CH2Cl2 (3 #200 mL). The organic layers were combined, washed with satd. brine (100 mL), dried with Na2SO4, and concentrated on a rotary evaporator. Flash chromatography with a gradient from hexanes to 1:1 hexanes/EtOAc afforded pure 5 (9.84 g, 76%).

Amide 5: TLC (2:1 hexanes/EtOAc): Rf=0.25; 1H NMR (CDCl3, 500 MHz) δ 3.65 (s, 3H), 3.37 (s, 3H), 3.27 (ddd, J=3.9, 6.9, 8.2 Hz, 1H), 3.14 (s, 3H), 3.00 (bs, 1H), 1.54 (ddd, J=4.0, 7.5, 14.9 Hz, 1H), 1.38 (tq, J=7.4, 14.9 Hz, 1H), 1.17 (d, J=6.9 Hz, 3H), 0.88 (t, J=7.4 Hz, 3H); 13C NMR (CDCl3, 125 MHz) δ 176.4, 83.8, 61.5, 58.5, 39.5, 32.2, 25.1, 14.3, 9.5; FTIR (film) vmax 3581, 3502, 2969, 2934, 2882, 2820, 1658, 1457, 1379 cm-1; HR-ESI-MS m/z calcd. For C9H19O3N [M]+: 189.1365. found 189.1362; $[\alpha]^{25}_D$=−13.0° (c=1.0 CHCl3).

Example 13

(4S,5S,E)-ethyl 5-methoxy-4-methylhept-2-enoate (6). Conversion of amide 5 to unsaturated ester 6 was conducted in a single day, as optimal yields were obtained when both steps were run without interruption. Amide 6 (19.2 g, 0.101 mol) was dissolved in CH2Cl2 (1 L) and cooled to −78° C. DIBAL-H as a 1M solution in hexanes (202 mL, 0.202 mol) was added slowly over 20 min. It was key to use DIBAL-H in hexanes as the resulting aldehyde S4 co-distilled with toluene upon rotary evaporation. The mixture was stirred for 2 h at −78° C. (during this period the phosphate anion was prepared as described in the next paragraph). Care was taken to prevent warming Acetone (100 mL) was added over 25 min at −78° C. and the mixture was warmed to 0° C. A satd. solution of Rochelle salt (300 mL) was added and the mixture was warmed to rt and stirred until clear, typically within 5 h. The mixture was extracted with CH2Cl2 (3 #200 mL). The organic layers were combined, washed with satd. brine (100 mL), dried with Na2SO4, filtered through a plug of SiO2 (250 g) washing with EtOAc (150 mL), concentrated on a rotary evaporator with the bath cooled to 4° C. to afford crude aldehyde S4, which was diluted in THF (100 mL) immediately after concentration, and used immediately thereafter.

NaH (11.4 g, 0.284 mol) was suspended in THF (1 L) and cooled to 0° C. Ethyl 2-(diethoxyphosphoryl)acetate (S5) (48.1 mL, 0.304 mol) in THF (100 mL) was added dropwise over 30 min. The mixture was stirred at 0° C. for 2 h at which point crude aldehyde S4 dissolved in THF (100 mL) was added over 15 min. The mixture was stirred at 0° C. After 3 h, TLC analysis indicated completion. A 25% solution of NH4Cl (200 mL) was added and the mixture was extracted with EtOAc (3×600 mL). The organic layers were combined, washed with satd. brine (500 mL), dried with Na2SO4, filtered through a plug of SiO2 (200 g) washing with EtOAc (300 mL), concentrated on a rotary evaporator. Flash chromatography with a gradient from hexanes to 1:1 hexanes/EtOAc afforded pure 6 (9.84 g, 89%).

Ester 6: TLC (10:1 hexanes/EtOAc): Rf=0.35; 1H NMR (CDCl3, 500 MHz) δ 6.94 (dd, J=7.7, 15.8 Hz, 1H), 5.81 (dd, J=1.2, 15.8 Hz, 1H), 4.17 (q, J=7.2 Hz, 2H), 3.35 (s, 3H), 2.99 (dt, J=5.1, 10.0 Hz, 1H), 2.57 (pd, J=1.2, 6.9 Hz, 1H), 1.50 (dqd, J=4.4, 7.5, 14.8 Hz, 1H), 1.40 (dp, J=7.3, 14.5 Hz, 1H), 1.27 (t, J=7.2 Hz, 3H), 1.01 (d, J=6.8 Hz, 3H), 0.90 (t, J=7.4 Hz, 3H); 13C NMR (CDCl3, 125 MHz) δ 166.8, 151.3, 121.1, 85.6, 60.3, 57.9, 39.3, 23.9, 14.9, 14.4, 9.9; FTIR (film) vmax 2978, 2934, 2882, 2820, 1719, 1650, 1466 cm-1; HR-ESI-MS m/z calcd. for C11H20O3 [M]+: 200.1407. found 200.1405; $[\alpha]^{25}_D$=−45.4° (c=1.0, CH2Cl2).

Example 14

(4S,5S,E)-5-methoxy-4-methylhept-2-en-1-ol (7). Ester 6 (18.2 g, 0.091 mol) was dissolved in CH2Cl2 (0.9 L) and cooled to −78° C. DIBAL-H as a 1M solution in hexanes (272 mL, 0.273 mol) was added over 20 min. After 1 h, acetone (100 mL) was added at −78° C. over 20 min and the mixture was cooled over 30 min to 0° C. A satd. solution of Rochelle salt (300 mL) was added and the mixture was warmed to rt and stirred until clear, typically 4-5 h. The mixture was extracted with CH2Cl2 (3 #500 mL). The organic layers were combined, washed with satd. brine (100 mL), dried with Na2SO4, filtered through a plug of SiO2 (200 g) washing with EtOAc (300 mL), and concentrated on a rotary evaporator. Flash chromatography with a gradient from hexanes to 1:1 hexanes/EtOAc afforded pure 7 (10.2 g, 71%). Allylic alchol 7 dissolved in benzene (0.1 g/mL) and stored frozen at −80° as the stock material for the preparation of 8. As needed, samples of 7 were thawed, concentrated on a rotary evaporator and converted to 8.

Allylic alcohol 7: TLC (6:1 hexanes/EtOAc): Rf=0.40; 1H NMR (CDCl3, 400 MHz) δ 5.65 (m, 2H), 4.10 (m, 2H), 3.36 (s, 3H), 2.92 (ddd, J=4.3, 5.7, 7.5 Hz, 1H), 2.44 (m, 1H), 1.52 (dqd, J=4.3, 7.5, 19.2 Hz, 1H), 1.41 (m, 1H), 1.01 (d, J=6.8 Hz, 3H), 0.90 (t, J=7.4 Hz, 3H), 13C NMR (CDCl3, 100 MHz) δ 135.3, 129.0, 86.4, 64.0, 57.8, 39.0, 23.6, 16.0, 10.0; FTIR (film) vmax 3388, 2968, 2932, 2876, 2826, 1460, 1375 cm-1; HR-ESI-MS m/z calcd. for C9H17O2 [M−H]+: 157.1223. found 157.1226; $[\alpha]^{25}_D$=−34.5° (c=0.2, CHCl3).

Example 15

((2R,3R)-3-((2R,3S)-3-methoxypentan-2-yl)oxiran-2-yl) methanol (S6). Ti(OiPr)4 (2.71 mL, 8.94 mmol) was added to (−)-diethyl tartrate (1.9 mL, 11.18 mmol) in CH2Cl2 (100 mL) over 4 Å molecular sieves (1 g) cooled to −20° C. The resulting mixture was stirred at −20° C. for 30 min. A solution of allylic alcohol 7 (1.18 g, 7.45 mmol) in CH2Cl2 (10 mL) was added dropwise. The reaction was warmed to −10° C. over 1 h and stirred at −10° C. for 2 h. The reaction was poured onto a solution of 30% FeSO4 (30 mL) and 10% tartaric acid (100 mL) that was precooled to 0° C. The mixture was stirred for 20 min and the layers were separated. The aqueous layer was extracted with Et2O (3 #30 mL). The organic layers were combined, treated with 30% NaOH in brine (15 mL) at 0° C. for 1 h. The mixture was separated and the aqueous layer extracted with Et2O (3 #50 mL). The organic layers were combined, washed with brine, dried with Na2SO4 and concentrated. Flash chromatography with a gradient from 2:1 hexanes/EtOAc to 1:1 hexanes/EtOAc afforded epoxyalcohol S6 (910 mg, 70%), as a clear oil.

Epoxyalcohol S6: TLC (2:1 hexanes/EtOAc): Rf=0.10; 1H NMR (CDCl3, 400 MHz) δ 3.93 (ddd, J=2.4, 5.7, 12.4 Hz, 2H), 3.63 (ddd, J=4.3, 7.2, 12.8 Hz, 1H), 3.41 (s, 3H), 3.21 (dt, J=4.1, 6.5 Hz, 1H), 2.98 (m, 2H), 1.63 (m, 1H), 1.54 (m, 1H) 1.51 (m, 1H), 0.92 (d, J=6.9 Hz, 3H), 0.90 (d, J=6.7 Hz, 3H); 13C NMR (CDCl3, 100 MHz) δ 83.9, 62.1, 58.3, 58.0, 58.0, 38.5, 23.9, 10.3, 10.2; FTIR (film) vmax 3422, 2972, 2930, 2879, 1468, 1103 cm-1; HR-ESI-MS m/z calcd. for C9H18O3 [M]+: 174.1250. found 174.1249; $[\alpha]^{25}_D$=+4.0° (c=0.075, CHCl3).

Example 16

(2S,3R)-3-((2R,3S)-3-methoxypentan-2-yl)oxirane-2-carbaldehyde (8). 2-Iodoxybenzoic acid (IBX) (4.0 g, 14.1 mmol) was added to epoxyalcohol S6 (1.23 g, 7.07 mmol) dissolved in EtOAc (70 mL). The suspension heated to 80° C. overnight. The resulting mixture was cooled to 0° C. and filtered through a plug of SiO2 eluting with EtOAc. The solvent was evaporated to afford aldehyde 8 (1.20 g, 99%) as a clear oil.

Aldehyde 8: TLC (2:1 hexanes/EtOAc): Rf=0.55; 1H NMR (CDCl3, 400 MHz) δ 9.03 (d, J=6.3 Hz, 1H), 3.41 (s, 3H), 3.28 (dd, J=2.0, 7.5 Hz, 1H), 3.23 (td, J=3.7, 6.6 Hz, 1H), 3.17 (dd, J=2.0, 6.3 Hz, 1H), 1.64 (m, 2H), 1.49 (qd, J=7.4, 13.9 Hz, 1H), 0.93 (d, J=7.1 Hz, 3H), 0.92 (t, J=7.5 Hz, 3H); 13C NMR (CDCl3, 100 MHz) δ 198.6, 83.7, 59.0, 58.7, 58.3, 38.3, 23.7, 10.2, 10.0; FTIR (film) vmax 2972, 2930, 2879, 2828, 1732, 1468, 1103 cm-1; HR-ESI-MS m/z calcd. for C9H17O3 [M+H]+: 173.1172. found 173.1174.

Example 17

B. Synthesis of core component 21. Component 21 was prepared in 14 steps in 2% yield from 4-(tert-butyldimethylsilyl)-oxo-1-butanol.

(100 mL) and brine (100 mL), dried with MgSO4, and concentration under reduced pressure. Flash chromatography with a gradient from hexanes to 10:1 hexanes/EtOAc afforded pure aldehyde 9 (8.0 g, 90%) that matched previously published spectra.

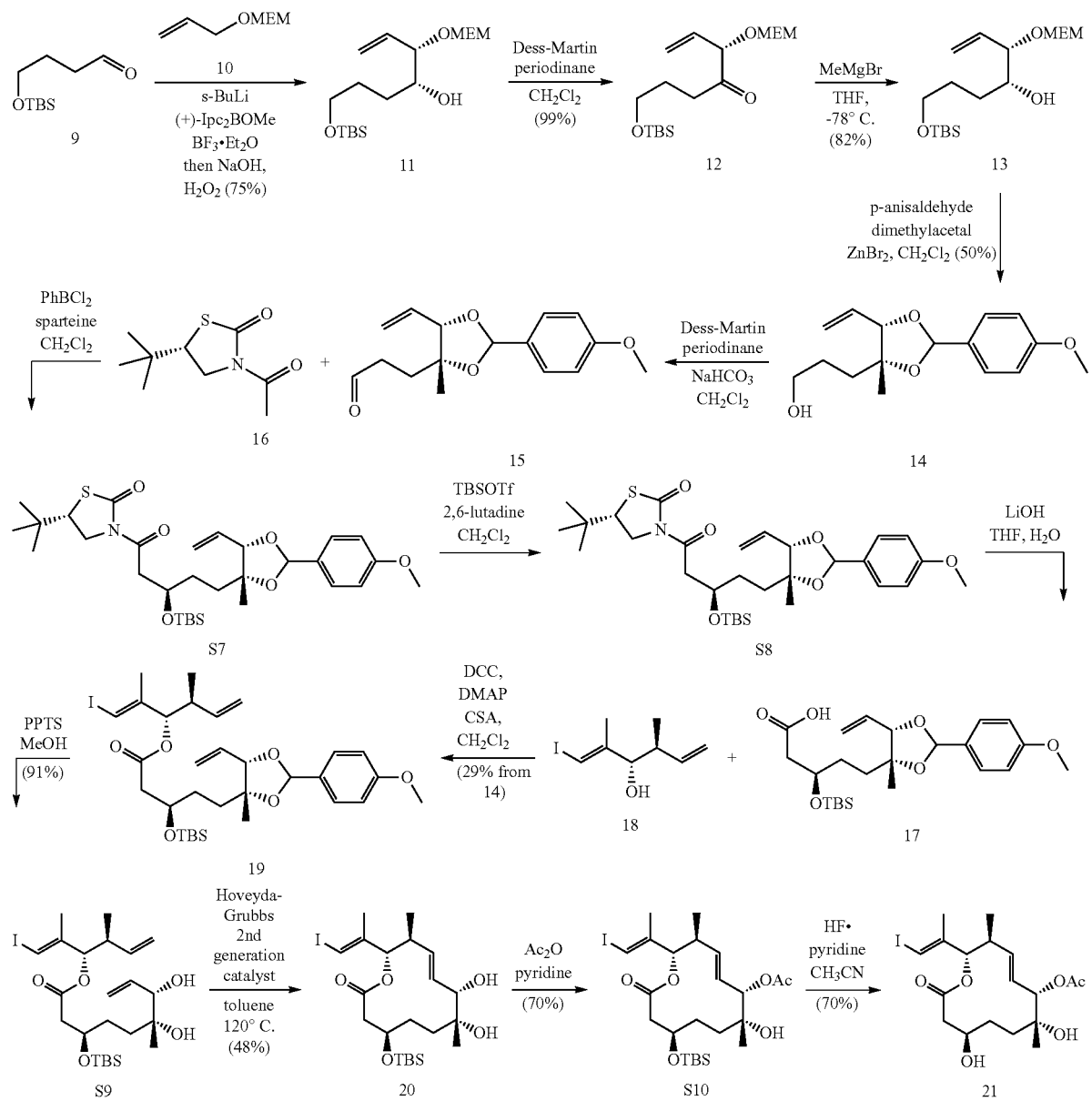

Scheme S2. Synthesis of core macrolide 21.

4-(tert-butyl-dimethyl-silanyloxy)-butyraldehyde (9). Oxalyl chloride (5.7 mL, 66.1 mmol) was added dropwise to the mixture of CH2Cl2 (300 mL) and DMSO (9.4 mL, 132.2 mmol) at −78° C. and stirred for 20 min. A solution of 4-(tert-butyldimethylsilyl)-oxy-1-butanol (9.0 g, 44.1 mmol) dissolved in CH2Cl2 (15 mL) was added dropwise, and the mixture was stirred for 1 h at −78° C. Triethylamine (29.2 mL, 208.0 mmol) was added and the mixture was warmed gradually to rt. After 1 h, satd. NaHCO3 (15 mL) was added. The mixture was extracted with Et2O (3 #50 mL). The organic layers were combined, washed with $H_2O$

Example 18

(8S,9S)-14,14,15,15-tetramethyl-8-vinyl-2,5,7,13-tetraoxa-14-silahexadecan-9-ol (11). A 1.3 M solution of s-BuLi in cyclohexane (16.1 mL, 20.9 mmol) was added to a solution of 3-((2-methoxyethoxy)methoxy)prop-1-ene5 (3.6 g, 24.9 mmol) in THF (20 mL) at −78° C. over 30 min. After an additional 30 min at −78° C., a solution was (+)-Ipc2B(OMe) (5.1 g, 20.9 mmol) in THF (15 mL) was added. The cold bath was removed and the reaction mixture was warmed to rt over 45 min. The mixture was then cooled to −78° C. and BF3.Et2O (3.4 mL, 26.9 mmol) was added dropwise. Aldehyde 9 (4.2 g, 20.8 mmol) in THF (9 mL) was added immediately thereafter. The mixture was stirred at −78° C. for 3 h and then slowly warmed to rt overnight. The solvent was removed under vacuum and the residue was dissolved in Et20 (100 mL). After cooling to 0° C., the Et2O solution was treated with a mixture of 30% H2O2 (6.7 mL) and 1N NaOH (54 mL). The ice bath was removed and the reaction stirred at rt for 4 h. The layers were separated and the aqueous layer was extracted with EtOAc (3×50 mL). The organic layers were combined, washed with brine, dried with Na2SO4 and concentrated. Flash chromatography with a gradient from hexanes to 2:1 hexanes/EtOAc provided alcohol 11 (6.5 g, 75%), as a colorless oil.

Alcohol 11: TLC (1:1 hexanes/EtOAc): Rf=0.40; 1H NMR (CDCl3, 400 MHz) δ 5.67 (ddd, J=18.3, 10.7, 7.9 Hz, 1H), 5.28 (m, 2H), 4.77 (d, J=6.9 Hz, 1H), 4.68 (d, J=6.9 Hz, 1H), 3.89 (t, J=7.3 Hz, 1H), 3.81 (ddd, J=10.9, 4.9, 4.0 Hz, 1H), 3.67-3.58 (m, 3H), 3.57-3.49 (m, 3H), 3.37 (s, 3H), 2.95 (d, J=3.5 Hz, 1H), 1.75-1.55 (m, 4H), 1.45-1.33 (m, 1H), 0.87 (s, 9H), 0.02 (s, 6H); 13C NMR (CDCl3, 100 MHz) δ 135.0, 120.0, 93.2, 81.7, 73.3, 71.9, 67.6, 63.3, 59.2, 29.6, 29.0, 26.1, 18.5, −5.0; FTIR (film) vmax 3347, 2927, 2856, 1616, 1250, 1021 cm-1; HR-ESI-MS m/z calcd. for C17H36O5 SiNa [M+Na]+: 371.2224. found 371.2223.

Example 19

(S)-14,14,15,15-tetramethyl-8-vinyl-2,5,7,13-tetraoxa-14-silahexadecan-9-one (12). Dess-Martin periodinane (9.0 g, 21.3 mmol) was added to a suspension of NaHCO3 (5.4 g, 64.4 mmol) and alcohol 11 (6.2 g, 17.8 mmol) in CH2Cl2 (350 mL) at 0° C. The ice bath was immediately removed and solution was stirred at rt. After 2 h, satd. NaHCO3 (40 mL) was added followed by 1N Na2S2O3 (30 mL). The biphasic mixture was stirred for 2 h and the layers separated. The aqueous layer was extracted with EtOAc (3 #50 mL). The organic layers were combined, washed with H2O (10 mL) and brine (10 mL), and dried with Na2SO4 and concentrated. The residue filtered through a plug of SiO2 with EtOAc to yield ketone 12 (6.1 g, 99%), as a colorless oil.

Ketone 12: TLC (1:1 hexanes/EtOAc): Rf=0.67; 1H NMR (CDCl3, 500 MHz) δ 5.76 (ddd, J=11.3, 7.3, 6.8 Hz, 1H), 5.45 (dt, J=17.2, 1.3 Hz, 1H), 5.35 (dt, J=10.3, 1.2 Hz, 1H), 4.79 (d, J=6.9 Hz, 1H), 4.74 (d, J=7.0 Hz, 1H), 4.61 (dt, J=6.7, 1.3 Hz, 1H), 3.76 (m, 1H), 3.67 (m, 1H), 3.59 (t, J=6.1 Hz, 2H), 3.52 (d, J=4.5 Hz, 1H), 3.51 (d, J=3.8 Hz, 1H) 3.36 (s, 3H), 2.62 (qt, J=18.1, 7.3 Hz, 2H), 1.76 (qd, J=6.8, 3.4 Hz 2H), 0.86 (s, 9H), 0.01 (s, 6H); 13C NMR (CDCl3, 125 MHz) δ 208.2, 132.6, 120.1, 93.7, 82.6, 82.6, 71.7, 67.5, 62.0, 59.1, 34.8, 26.3, 25.9, 26.3, 18.3, −5.2; FTIR (film) vmax 2954, 2929, 2857, 1720, 1472, 1256, 1101 cm-1; HR-ESI-MS m/z calcd. for C17H34O5SiNa [M+Na]+: 369.2068. found 369.2067.

Example 20

(8S,9R)-9,14,14,15,15-pentamethyl-8-vinyl-2,5,7,13-tetraoxa-14-silahexadecan-9-ol (13). A solution of 12 (6.1 g, 17.5 mmol) in THF (250 mL) at −78° C. was treated dropwise with a 3M solution of MeMgBr in THF (8.8 mL, 26.2 mmol). The resulting mixture was stirred for 30 min at −78° C. before slowly warming to rt. After 1 h at rt, the solution was cooled to −78° C. and quenched by the dropwise addition of 20 mL of a saturated NH4Cl (20 mL). The resulting mixture was warmed to rt, diluted with Et2O (100 mL), and the layers were separated. The aqueous layer was further extracted with Et2O (3 #50 mL). The organic layers were combined, washed with H2O (10 mL) and brine (10 mL), dried with Na2SO4 and concentrated. Flash chromatography with a gradient from hexanes to 4:1 hexanes/EtOAc provided alcohol 13 (5.2 g, 82%) as a colorless oil.

Alcohol 13: TLC (1:1 hexanes/EtOAc): Rf=0.45; 1H NMR (CDCl3, 500 MHz) δ 5.74 (ddd, J=18.4, 10.2, 8.1 Hz, 1H), 5.30 (m, 2H), 4.76 (d, J=7.1 Hz, 1H), 4.67 (d, J=7.1 Hz, 1H), 3.86 (d, J=8 Hz, 1H), 3.82 (ddd, J=10.9, 5.2, 3.7 Hz, 1H), 3.65-3.50 (m, 5H), 3.37 (s, 3H), 2.70 (s, 1H), 1.70-1.55 (m, 3H), 1.48-1.38 (m, 1H), 1.15 (s, 3H), 0.87 (s, 9H) 13C NMR (CDCl3, 125 MHz) δ 134.3, 120.2, 93.2, 84.4, 73.4, 71.8, 67.5, 63.9, 59.1, 33.8, 26.5, 26.0, 23.5, 18.4, −5.2; FTIR (film) vmax 2954, 2929, 2857, 2359, 1472, 1255, 1097, 1037 cm-1; HR-ESI-MS m/z calcd. for C18H38O5SiNa [M+Na]+: 385.2381. found 385.2380.

Example 21

3-((4R,5S)-2-(4-methoxyphenyl)-4-methyl-5-vinyl-1,3-dioxolan-4-yl)propan-1-ol (14). p-Anisaldehyde dimethylacetal (10.1 mL, 57.4 mmol) and anhydrous ZnBr2 (12.9 g, 57.4 mmol) were added sequentially to a solution of 13 (5.2 g, 14.3 mmol) in CH2Cl2 (250 mL). The mixture was stirred for 48 h at rt. Satd. NaHCO3 (100 mL) was added. After stirring for 1 h, the organic layer was collected and the aqueous layer was further extracted with EtOAc (3 #50 mL). The organic layers were combined, washed with H2O (50 mL) and brine (50 mL), dried with Na2SO4, and concentrated. Flash chromatography with a gradient from 2:1 hexanes/EtOAc to 1:1 hexanes/EtOAc yielded a 3:5 mixture of acetal diastereomers 14 (1.9 g, 50%).

Alcohols 14: TLC (1:1 hexanes/EtOAc): Rf=0.37; 1H NMR Major (CDCl3, 400 MHz) δ 7.43 (d, J=8.7 Hz, 2H), 6.91 (d, J=8.7 Hz, 2H), 5.89 (s, 1H), 5.97-5.82 (m, 1H), 5.42 (dt, J=17.1, 1.3 Hz, 1H), 5.31 (dt, J=10.4, 1.2 Hz, 1H), 4.27 (dt, J=7.1, 1 Hz, 1H), 4.24 (dt, J=7.1, 1 Hz), 3.81 (s, 3H), 3.71 (dd, J=9.7, 5.6 Hz, 1H), 3.64-3.58 (m, 1H), 1.90-1.58 (m, 4H), 1.38 (s, 3H); Minor: δ 7.40 (d, J=8.7 Hz, 2H), 6.90 (d, J=8.6 Hz, 2H), 6.01 (s, 1H), 5.97-5.82 (m, 1H), 5.40 (dt, J=17.1, 1.4 Hz, 1H), 5.28 (dt, J=10.3, 1.3 Hz, 1H), 4.24 (dt, J=7.1, 1 Hz, 1H), 3.81 (s, 3H), 3.71 (dd, J=9.7, 5.6 Hz, 1H), 3.64-3.58 (m, 1H), 1.90-1.58 (m, 4H), 1.39 (s, 3H); 13C NMR (CDCl3, 100 MHz) δ 160.6, 159.9, 133.7, 133.6, 132.7, 131.8, 131.0, 128.3, 127.7, 117.6, 117.6, 113.8, 113.7, 102.3, 102.0, 87.8, 86.0, 83.3, 82.2, 62.9, 62.8, 54.6, 33.6, 29.8, 27.3, 26.9, 22.3, 21.9; FTIR (film) vmax 3421, 3080, 2938, 1718, 1614, 1516, 1932, 1303, 1249, 1170, 1032 cm-1; HR-ESI-MS m/z calcd. for C16H22O4 Na [M+Na]+: 301.1410. found 301.1411.

Example 22

((3R)-(3S,4S,E)-1-iodo-2,4-dimethylhexa-1,5-dien-3-yl-3-((tert-butyldimethylsilyl)oxy)-5-((4R,5S)-2-(4-methoxyphenyl)-4-methyl-5-vinyl-1,3-dioxolan-4-yl)pentanoate (19). Esters 19 were prepared through a five-step sequence from alcohols 14, which was optimally conducted in rapid succession without the purification of the resulting intermediates. The following provides a detailed procedure for this process.

Dess-Martin periodinane (3.9 g, 9.3 mmol) was added to a solution of alcohols 14 (2.15 g, 7.7 mmol) and NaHCO3 (3.2 g, 37.5 mmol) in CH2Cl2 (70 mL) at 0° C. After 1 h, satd. NaHCO3 (10 mL) and 1N Na2S2O3 (10 mL) were added and the mixture was stirred at rt for an additional 1 h.

The layers were separated and the aqueous layer was further extracted with CH2Cl2 (3 #30 mL). The organic layers were combined, washed with $H_2O$ (50 mL) and brine (50 mL), dried with Na2SO4 and concentrated to yield aldehydes 15 (1.6 g). The resulting product was used immediately.

PhBCl2 (1.0 mL, 7.7 mmol) was added dropwise to a solution of N-acetyl thiazolidinethione 16 (1.7 g, 7.7 mmol) in CH2Cl2 (30 mL) resulting in an orange solution. After stirring for 10 min, (−)-sparteine (3.5 mL, 15.1 mmol) was added dropwise. The reaction was stirred at rt for 30 min and then cooled to −78° C. A solution of aldehydes 15 (1.5 g, 5.8 mmol) in CH2Cl2 (5 mL) was added dropwise. The reaction was stirred for 5 h at −78° C. and then warmed to rt over 2 h by allowing the dry ice to evaporate. After stirring at rt for an additional 30 min, hexanes (40 mL) and 30% H2O2 (20 mL) were added and the resulting mixture was stirred for 5 min at rt. The solution was diluted with hexanes (320 mL) and CH2Cl2 (80 mL) and the layers were separated. The organic layer was further washed with $H_2O$ (5 mL) and brine (50 mL), dried over Na2SO4, filtered, and concentrated at reduced pressure to afford an orange oil. The product was filtered through a pad of neutral alumina eluting with 5:1 hexanes/CH2Cl2 to EtOAc to provide the crude aldol adduct (3.7 g) as a yellow oil, which was used immediately.

2,6-Lutidine (2.6 mL, 22.5 mmol) and TBSOTf (2.6 mL, 11.3 mmol) were added sequentially in a dropwise fashion to a solution of crude aldol adduct (3.7 g) in CH2Cl2 (50 mL) cooled to −78° C. The reaction was warmed to rt by removing the cooling bath and stirred at rt for 1 h. Satd. NaHCO3 (4 mL) was added and the layers separated. The aqueous layer was further extracted with EtOAc (3 #20 mL). The organic layers were combined, washed with brine (20 mL), dried with Na2SO4, and concentrated to give a crude TBS-ether as an orange oil, which was used immediately after preparation.

LiOH.H2O (900.0 mg, 21.4 mmol) was added to solution of crude TBS-ether adduct in MeCN (8 mL) and $H_2O$ (2 mL) at 0° C. The resulting mixture was warmed to rt and stirred overnight. The pH was adjusted to 7 by the addition of 1N HCl. The resulting mixture was extracted with EtOAc (3 #20 mL), dried with Na2SO4, and concentrated to provide a light yellow oil. Flash chromatography with a gradient from hexanes to 2:1 hexanes/EtOAc yielded acids 17 (1.4 g) as a colorless oil. As a means of checking the purity, acids 17 (~20 mg scale) were converted to their corresponding methylesters by treatment with trimethylsilyldiazomethane (spectral properties reported below). Samples of acids 17 were best used immediately after preparation and if needed could be stored for a few days frozen in benzene solutions at −80° C.

Methylester of acids 17: TLC (2:1 hexanes/EtOAc): Rf=0.55; 1H NMR Major (CDCl3, 400 MHz) δ 7.40 (m, 2H), 6.89 (m, 2H), 5.87 (s, 1H), 5.99-5.77 (m, 1H), 5.40 (dd, J=17.1, 4.9 Hz, 1H), 5.31-5.27 (m, 1H), 4.25 (d, J=6.9 Hz, 1H), 4.19-4.04 (m, 1H), 3.81 (s, 3H), 3.64 (s, 3H), 2.54-2.34 (m, 2H), 1.78-1.50 (m, 4H), 1.33 (s, 3H), 0.85 (s, 9H), 0.09 (s, 3H), 0.05 (s, 3H). Minor δ 7.40 (m, 2H), 6.89 (m, 2H), 5.95 (s, 1H), 5.99-5.77 (m, 1H), 5.40 (dd, J=17.1, 4.9 Hz, 1H), 5.31-5.27 (m, 1H), 4.22 (d, J=6.9 Hz, 1H), 4.19-4.04 (m, 1H), 3.80 (s, 3H), 3.67 (s, 3H), 2.54-2.34 (m, 2H), 1.78-1.50 (m, 4H), 1.34 (s, 3H), 0.88 (s, 9H), 0.04 (s, 3H), 0.02 (s, 3H); 13C NMR (CDCl3, 100 MHz) δ 172.3, 172.2, 160.5, 160.4, 132.9, 131.9, 130.3, 128.3, 127.9, 118.9, 118.9, 113.9, 113.9, 102.4, 101.9, 88.0, 86.3, 83.5, 82.3, 69.8, 69.7, 55.5, 55.5, 51.7, 51.6, 42.8, 42.6, 32.4, 31.6, 31.1, 29.9, 28.2, 25.9, 25.9, 22.7, 22.1, 18.2, 18.1, −4.5, −4.7; FTIR (film) vmax 2972, 2930, 2879, 2828, 1732, 1468, 1103 cm-1; HR-ESI-MS m/z calcd. for C25H40O6SiNa [M+Na]+: 487.2486. found 487.2485.

Acids 17 (1.3 g) and allylic alcohol 18 (780.0 mg, 3.1 mmol)6 were dissolved in CH2Cl2 (100 mL). After cooling to 0° C., DMAP (400.0 mg, 3.3 mmol), camphorsulfonic acid (CSA) (616.0 mg, 2.7 mmol) and dicyclohexylcarbodiimide (DCC) (962.0 mg, 4.6 mmol) were added sequentially. After 15 min at 0° C., the mixture was warmed to rt and stirred overnight. The resulting mixture was concentrated via rotary evaporation. Flash chromatography eluting with 10:1 hexanes/EtOAc afforded esters 19 (1.54 g, 29% over 5 steps from 14) as a colorless oil.

Esters 19: TLC (5:1 hexanes/EtOAc): Rf=0.55; 1H NMR Major (CDCl3, 400 MHz) δ 7.40 (t, J=8.5 Hz, 2H), 6.88 (m, 2H), 6.32 (d, J=7.9 Hz, 1H), 5.87 (s, 1H), 5.98-5.78 (m, 1H), 5.72-5.58 (m, 1H), 5.45-5.36 (m, 1H), 5.32-5.25 (m, 1H), 5.13 (t, J=8.3 Hz, 1H), 5.09-4.96 (m, 2H), 4.25 (d, J=6.9 Hz, 1H), 4.16-4.00 (m, 1H), 3.81 (s, 3H), 2.55-2.32 (m, 3H), 1.79 (s, 3H), 1.73-1.51 (m, 3H), 1.33 (s, 3H), 1.29-1.15 (m, 1H), 0.95-0.82 (m, 12H), 0.10-0.01 (m, 6H); 13C NMR (CDCl3, 100 MHz) δ 170.5, 170.4, 160.5, 160.3, 155.9, 144.6, 144.5, 139.4, 139.4, 133.0, 128.4, 127.9, 127.9, 118.9, 116.0, 116.0, 113.9, 113.8, 102.4, 101.9, 87.9, 86.3, 83.4, 82.3, 81.8, 80.7, 80.6, 69.5, 69.4, 55.5, 55.5, 43.1, 42.9, 40.3, 40.3, 32.7, 31.5, 31.0, 26.0, 22.7, 22.1, 20.4, 20.4, 18.2, 18.2, 16.6, 16.5, −4.3, −4.4; FTIR (film) vmax 2956, 2929, 2856, 1739, 1616, 1517, 1378, 1249, 1170, 1070 cm-1; HR-ESI-MS m/z calcd. for C32H49IO6SiNa [M+Na]+: 707.2235. found 707.2237.

Example 23

(3R,6R,7S)-(3S,4S,E)-1-iodo-2,4-dimethylhexa-1,5-dien-3-yl-3-((tert-butyldimethyl-silyl)oxy)-6,7-dihydroxy-6-methylnon-8-enoate (S9). Pyridinium p-toluenesulfonate (PPTS) (220.0 mg, 875.0% mol) was added to a solution of 19 (202.0 mg, 295.0% mol) in MeOH (8 mL) at 0° C. The reaction was warmed to rt. After 4 h at rt, satd. NaHCO3 (3 mL) was added. The layers were separated and the aqueous layer further extracted with EtOAc (3 #3 mL). The organic layers were combined, washed with brine (5 mL), dried with Na2SO4 and concentrated. Flash chromatography with a gradient from hexanes to 4:1 hexanes/EtOAc afforded diol S9 (150.0 mg, 91%), as a colorless oil. Diol S9: TLC (4:1 hexanes/EtOAc): Rf=0.30; 1H NMR (CDCl3, 400 MHz) δ 6.31 (s, 1H), 5.91 (ddd, J=17.1, 11.0, 6.4 Hz, 1H), 5.65 (ddd, J=17.6, 10.2, 7.9 Hz, 1H), 5.33 (d, J=17.5 Hz, 1H), 5.24 (d, J=10.4 Hz, 1H), 5.12 (d, J=8.3 Hz, 1H), 5.08-4.98 (m, 2H), 4.08 (m, 1H), 3.94 (d, J=5.8 Hz, 1H), 2.54-2.37 (m, 3H), 1.81 (s, 3H), 1.71-1.55 (m, 4H), 1.37-1.26 (m, 1H), 1.16 (s, 3H), 0.92 (d, J=6.9 Hz, 3H), 0.86 (s, 9H), 0.06 (s, 3H), 0.04 (s, 3H); 13C NMR (CDCl3, 100 MHz) δ 170.5, 144.5, 139.4, 136.7, 117.8, 116.1, 81.9, 80.6, 79.7, 74.1, 69.5, 42.7, 40.3, 31.8, 30.7, 26.0, 23.5, 20.4, 18.2, 16.6, −4.3, −4.7; FTIR (film) vmax 3431, 2929, 2856, 1739, 1472, 1378, 1255, 1169, 1095 cm-1; HR-ESI-MS m/z calcd. for C24H43IO5SiNa [M+Na]+: 589.1817. found 589.1819.

Example 24

(4R,7R,8S,11S,12S,E)-4-((tert-butyldimethylsilyl)oxy)-7,8-dihydroxy-12-(E)-1-iodoprop-1-en-2-yl)-7,11-dimethyloxacyclododec-9-en-2-one (20). A solution of Hoveyda-Grubbs 2nd generation catalyst (5.4 mg, 8.9% mol) in degassed toluene (5 mL) was added over 1 min to a solution of diol S9 (29.0 mg, 51.1% mol) in degassed toluene (15 mL) at 120° C. The mixture was stirred for 20 min. The mixture was cooled immediately to 0° C. by use of an ice bath and filtered through a pad of silica eluting with EtOAc (25 mL) and the solution was concentrated by a stream of N2 or Ar. Flash chromatography with a gradient from hexanes to 3:1 hexanes/EtOAc yielded macrolide 20 (13.0 mg, 48%), as a colorless oil.

Macrolide 20: TLC (2:1 hexanes/EtOAc): Rf=0.35; 1H NMR (CDCl3, 400 MHz) δ 6.45 (s, H), 5.72 (dd, J=15.1, 9.7 Hz, 1H), 5.43 (dd, J=15.1, 9.8 Hz, 1H), 5.12 (d, J=10.7 Hz, 1H), 3.86-3.77 (m, 2H), 2.56-2.35 (m, 4H), 2.29-2.12 (m, 1H), 1.78 (s, 3H), 1.59 (m, 4H), 1.30 (s, 3H), 0.89 (s, 9H), 0.06 (s, 3H), 0.04 (s, 3H); 13C NMR (CDCl3, 100 MHz) δ 168.8, 143.9, 137.2, 130.3, 83.9, 80.4, 77.4, 73.8, 70.7, 40.6, 40.6, 36.1, 30.4, 26.0, 24.9, 19.2, 18.3, 16.6, −4.5; FTIR (film) vmax 3446, 2975, 2928, 2875, 1734, 1256 cm-1; HR-ESI-MS m/z calcd. for C22H39IO5SiNa [M+Na]+: 561.1504. found 561.1506.

Example 25

(2 S,3 S,6S,7R,10R,E)-10-((tert-butyldimethylsilyl)oxy)-7-hydroxy-2-(E)-1-iodoprop-1-en-2-yl)-3,7-dimethyl-12-oxooxacyclododec-4-en-6-yl acetate (S10). Acetic anhydride (0.41 mL) was added to a solution of diol 20 (47.0 mg, 87.3% mol) in pyridine (2 mL) at rt. The reaction was terminated after 2 h by the addition of H2O (5 mL) followed by extraction with EtOAc (3×5 mL). The organic layer was washed with H2O (5 mL) and brine (5 mL), dried with Na2SO4 and concentrated. Flash chromatography with 2:1 hexanes/EtOAc afforded acetate S10 (36 mg, 70%), as a colorless oil.

Acetate S10: TLC (2:1 hexanes/EtOAc): Rf=0.30 1H NMR (CDCl3, 400 MHz) δ 6.45 (s, 1H), 5.57-5.56 (m, 2H), 5.08 (d, J=10.6, 1H), 5.04 (d, J=9.3 Hz, 1H), 3.83 (s, 1H), 2.56-2.31 (m, 3H), 2.08 (s, 3H), 1.77 (s, 3H), 1.70-1.38 (m, 4H), 1.20 (s, 3H), 0.95-0.82 (m, 12H), 0.88 (s, 9H), 0.06 (s, 3H), 0.04 (s, 3H); 13C NMR (CDCl3, 100 MHz) δ 169.9, 168.6, 143.8, 140.0, 125.9, 84.0, 80.4, 79.0, 73.8, 70.4, 40.6, 40.5, 35.6, 30.4, 26.0, 25.0, 21.5, 19.2, 18.3, 16.5, −4.5; FTIR (film) vmax 3462, 2929, 1740, 1462, 1369, 1249, 1166, 1089 cm-1; HR-ESI-MS m/z calcd. for C24H41IO6SiNa [M+Na]+: 603.1609. found 603.1613.

Example 26

(2S,3S,6S,7R,10R,E)-7,10-dihydroxy-2-(E)-1-iodoprop-1-en-2-yl)-3,7-dimethyl-12-oxooxacyclododec-4-en-6-yl acetate (21). HF.pyridine (2.5 mL) was added dropwise over 2 min to a solution of S10 (50.0 mg, 862.0% mol) in a mixture of MeCN (2.5 mL) and pyridine (2.5 mL) cooled to 0° C. After addition was complete, the solution was slowly warm to rt. After 2 h, satd. NaHCO3 (3 mL) was added and the mixture was extracted with EtOAc (3×5 mL). The organic layers were combined, washed with H2O (5 mL) and brine (5 mL), dried with Na2SO4 and concentrated. Flash chromatography with a gradient from hexanes to 3:1 hexanes/EtOAc yielded core 21 (11.0 mg, 70%), as a colorless oil.

Core 21: TLC (3:1 hexanes/EtOAc): Rf=0.16; 1H NMR (CDCl3, 400 MHz) δ 6.47 (s, 1H), 5.67 (dd, J=15.2, 9.5 Hz, 1H), 5.57 (dd, J=15.2, 9.7, 1H), 5.29 (d, J=10.5 Hz, 1H), 5.05 (d, J=9.5 Hz, 1H), 3.75 (bs, 1H), 3.42 (d, J=11.1 Hz, 1H), 2.66-2.44 (m, 3H), 2.09 (s, 3H), 1.82 (s, 3H), 1.62-1.31 (m, 4H), 1.20 (s, 3H), 0.90 (d, J=6.7 Hz, 3H); 13C NMR (CDCl3, 100 MHz) δ 172.0, 169.8, 143.5, 139.8, 126.3, 84.4, 80.4, 78.9, 73.5, 69.3, 41.1, 38.4, 35.3, 29.9, 24.8, 21.5, 19.2, 16.5; FTIR (film) vmax 3502, 3058, 2959, 2873, 1733, 1616, 1368, 1243, 1168, 1021 cm-1; HR-ESI-MS m/z calcd. for C18H27IO6Na [M+Na]+: 489.0745. found 489.0742.

Example 27

Synthesis of isomer 1SS. A three-step procedure was used to prepare isomer 1SS. This began by preparation of alkyne 24a from aldehyde 8 and mesylate 22a. Hydrostannylation of 24a afforded stannane S11a, which not characterized and used immediately after preparation. Stannane S11a was coupled to core 21 to afford isomer 1SS.

Scheme S3. Synthesis of isomers 1SS, 1SR, 1RS, and 1RR.

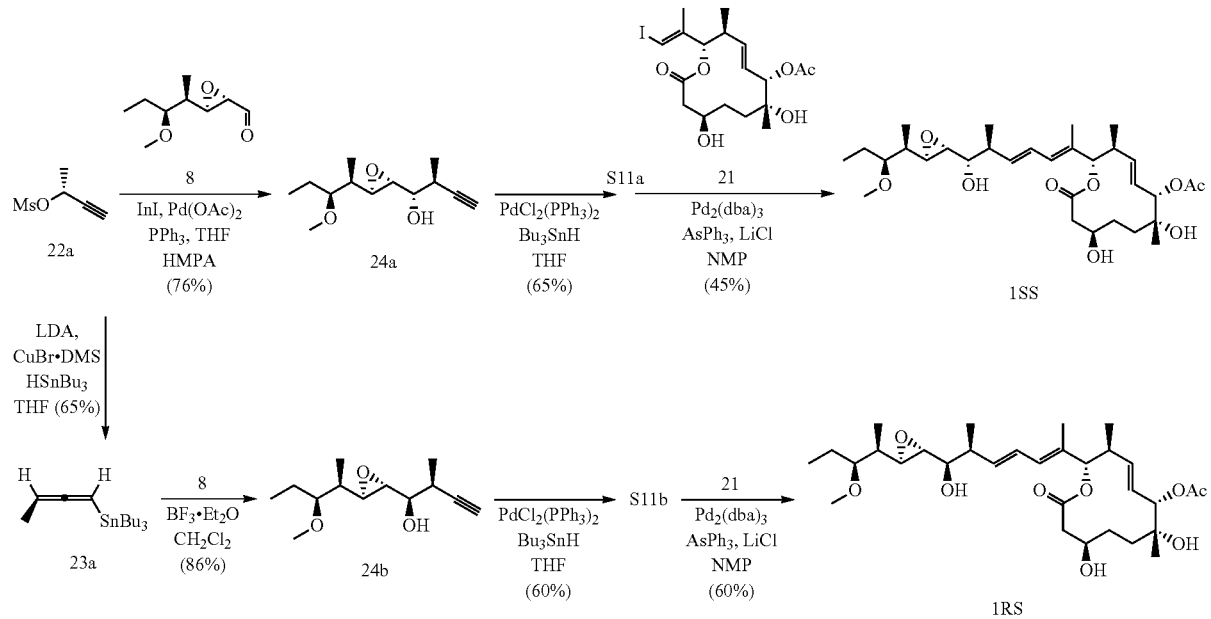

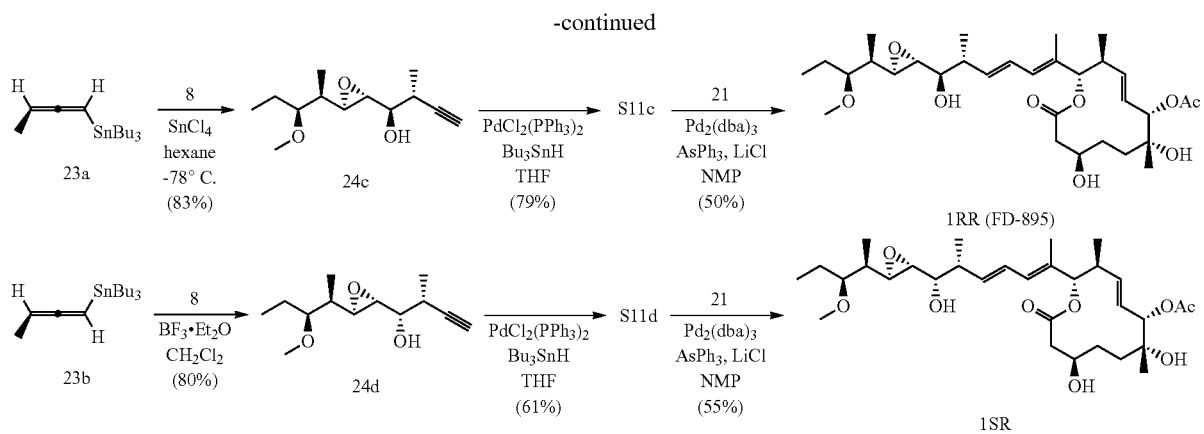

Example 28

(1S,2S)-1-((2R,3R)-3-((2R,3S)-3-methoxypentan-2-yl)oxiran-2-yl)-2-methylbut-3-yn-1-ol (24a). Pd(OAc)2 (7.0 mg, 31.0% mol) and PPh3 (8.0 mg, 30.0% mol) were sequentially added to a solution of aldehyde 8 (89.0 mg, 516.0% mol) in THF (2.25 mL) and HMPA (0.75 mL) cooled to 0° C. After 2 min, InI (184.0 mg, 761.0 mmol) and mesylate 22a7 (100 mg, 674.0% mol) were added sequentially. After 1 h at 0° C., H$_2$O (10 mL) was added and the mixture was extracted with EtOAc (3×10 mL). The organic layers were combined, washed with water (5 mL) and brine (5 mL), dried with Na2SO2 and concentrated. Flash chromatography with 3:1 hexanes/EtOAc yielded alkyne 24a (86.0 mg, 76%) as a clear oil.

Alkyne 24a: TLC (2:1 hexanes/EtOAc): Rf=0.50; 1H NMR (CDCl3, 400 MHz) δ 3.46 (d, J=3.46 Hz, 1H), 3.39 (s, 3H), 3.18 (ddd, J=10.3, 6.3, 3.9 Hz, 1H), 2.96 (dd, J=4.5, 2.3 Hz, 1H), 2.93 (dd, J=7.8, 2.3 Hz, 1H), 2.72 (m, 1H), 2.39 (d, J=5.8 Hz, 1H), 2.16 (d, J=2.5 Hz, 1H), 1.64 (m, 1H), 1.52-1.40 (m, 2H), 1.27 (d, J=7.1 Hz, 1H), 0.92 (d, J=7.1 Hz, 2H), 0.88 (t, J=7.4 Hz, 3H); 13C NMR (CDCl3, 100 MHz) δ 84.7, 83.8, 73.0, 71.3, 59.1, 58.3, 58.3, 38.8, 31.2, 23.9, 16.7, 10.4, 10.2; FTIR (film) vmax 3502, 3058, 2959, 2873, 1733, 1616, 1368, 1243, 1168, 1021 cm-1; HR-ESI-MS m/z calcd. for C13H22O3Na [M+Na]+: 249.1461. found 249.1460.

Example 29

(1S,2S,E)-1-((2R,3R)-3-((2R,3S)-3-methoxypentan-2-yl)oxiran-2-yl)-2-methyl-4-(tributylstannyl)but-3-en-1-ol (S11a). n-Bu3SnH (80.3 mg, 275.0% mol) was added in a dropwise fashion to a solution of alkyne 24a (57.0 mg, 252.0% mol) and PdCl2 (PPh3)2 (9.0 mg, 13.0% mol) in THF (5 mL) cooled to 0° C. This mixture was warmed to rt. After 15 min at rt, the alkyne was consumed as indicated by TLC analysis. The solution was concentrated and filtered quickly through a plug of silica gel deactivated with Et3N to afford S11a (84.0 mg, 65%), as a light yellow oil, which was used immediately after preparation.

Isomer 1SS. Pd2(dba)3 (1.5 mg, 1.6% mol), Ph3As (5.7 mg, 18.6% mol), and LiCl (1.0 mg, 23.5% mol) were added sequentially to a solution of vinyl iodide 21 (8.0 mg, 17.0% mol) and the crude stannane S11a (13.0 mg, 25.0% mol) in dried and degassed N-methylpyrrolidone (NMP) (1 mL). The reaction was stirred for 24 h at which point an additional Pd2(dba)3 (1.5 mg, 1.6% mol) and Ph3As (5.7 mg, 18.6% mol) were added. After stirring for an additional 24 h at rt, H$_2$O (3 mL) was added and the mixture was extracted with EtOAc (3×5 mL). The organic layers were combined, washed with H$_2$O (5 mL) and brine (5 mL), dried with Na2SO4 and concentrated. The remaining NMP was removed under a stream of N2 or Ar. Flash chromatography with a gradient from 1:1 hexanes/EtOAc to 2:1 EtOAc/hexanes followed by pTLC eluting with 2:1 EtOAc/hexanes afforded isomer 1SS (4.0 mg, 45%) a white wax.

Isomer 1SS: 1H NMR (C6D6, 400 MHz) δ 6.31 (dd, J=15.4, 10.9 Hz, 1H), 6.16 (d, J=9.9 Hz, 1H), 5.85-5.76 (m, 2H), 5.62 (dd, J=15.1, 9.9 Hz, 1H), 5.27 (d, J=6.4 Hz, 1H), 5.25 (d, J=5.4 Hz, 1H), 3.63 (d, J=11.5 Hz, 1H), 3.48 (bs, 1H); 13C NMR (C6D6, 100 MHz) δ 171.9, 168.7, 140.4, 138.0, 131.4, 131.4, 126.2, 126.0, 83.4, 82.4, 79.0, 74.9, 73.1, 69.1, 60.3, 59.4, 57.5, 42.4, 40.9, 39.1, 38.3, 35.6, 30.1, 24.5, 23.7, 20.5, 16.8, 16.2, 11.6, 10.4, 9.8; FTIR (film) vmax 2969, 2917, 2855, 1719, 1449, 1265, 1178, 1108, 1020, 715 cm-1; HR-ESI-MS m/z calcd. For C31H50O9Na [M+Na]+: 589.3347. found 589.3345.

Example 30

D. Synthesis of isomer 1RS. A three-step procedure was used to prepare isomer 1RS. This began by preparation of alkyne 24b from aldehyde 8 and allenylstannane 23a. Hydrostannylation of 24b afforded stannane S11b, which not characterized and used immediately after preparation. Stannane S11b was coupled to core 21 to afford isomer 1SS.

Example 31

(1R,2S)-1-((2R,3R)-3-((2R,3S)-3-methoxypentan-2-yl)oxiran-2-yl)-2-methylbut-3-yn-1-ol (24b). BF3.Et2O (673.0% L, 5.4 mmol) was added dropwise over 5 min to a solution of aldehyde 8 (310.0 mg, 1.8 mmol) and allenylstannane 23a8 (926.0 mg, 2.7 mmol) in dry CH2Cl2 (6 mL) cooled to −78° C. The reaction was stirred for 1 h at −78° C. MeOH (2.6 mL) and satd. NaHCO3 (0.3 mL) were added and the mixture was warmed to rt. The layers were separated and the aqueous layer further extracted with ether (3 #20 mL). The organic layers were combined, washed with brine and dried with Na2SO4 and concentrated. The residue was chromatographed on silica gel eluting with 4:1 hexanes/EtOAc to give alkyne 24b (350.0 mg, 86%) as a clear oil.

Alkyne 24b: TLC (2:1 hexanes/EtOAc): Rf=0.50; 1H NMR (CDCl3, 400 MHz) δ 3.56 (dd, J=7.5, 3.7 Hz, 1H), 3.41 (s, 3H), 3.19 (ddd, J=10.4, 6.3, 4.1 Hz, 1H), 3.05 (dd, J=8.0, 2.2 Hz, 1H), 2.90 (dd, J=4.4, 2.2 Hz, 1H), 2.80 (m, 1H), 2.16 (d, J=2.4 Hz, 1H), 2.08 (d, J=3.5 Hz, 1H), 1.67 (m, 1H), 1.54-1.43 (m, 2H), 1.30 (d, J=7.1 Hz, 3H), 0.97 (d, J=7.0 Hz, 3H), 0.90 (t, J=7.4 Hz, 3H); 13C NMR (CDCl3, 100 MHz) δ 84.5, 83.9, 72.3, 71.4, 64.3, 59.0, 58.3, 38.9, 30.5, 23.9, 17.2, 10.6, 10.2; FTIR (film) vmax 3438, 3309, 2972, 2937, 2879, 1647, 1465, 1089 cm-1; HR-ESI-MS m/z calcd. for C13H22O3Na [M+Na]+: 249.1461. found 249.1460.

Example 32

(1R,2S,E)-1-((2R,3R)-3-((2R,3S)-3-methoxypentan-2-yl) oxiran-2-yl)-2-methyl-4-(tributylstannyl)but-3-en-1-ol (S11b). n-Bu3SnH (131.4 mg, 450.0% mol) was added in a dropwise fashion to a solution of alkyne 24b (90.0 mg, 397.0% mol) and PdCl2 (PPh3)2 (14.0 mg, 20.0% mol) in THF (6 mL) at 0° C. The reaction was warmed to rt and was complete via TLC analysis after 15 min. The solution was concentrated and filtered quickly through a plug of silica gel deactivated with Et3N to afford S11b (121.0 mg, 65%), which was used immediately.

Isomer 1RS. Pd2(dba)3 (2.0 mg, 2.1% mol), Ph3As (6.4 mg, 20.8% mol), and LiCl (1.3 mg, 30.6 mmol) were added sequentially to a solution of vinyl iodide 21 (5 mg, 10.7% mol) and crude stannane S11b (8.0 mg, 15.0% mol) in dried and degassed NMP (2 mL). The reaction was stirred at rt for 24 h at which point an additional Pd2(dba)3 (2.0 mg, 2.1% mol) and Ph3As (6.4 mg, 20.8% mol) were added. After stirring for an additional 24 h at rt, H₂O (3 mL) was added and the mixture was extracted with EtOAc (3 #5 mL). The organic layers were combined, washed with H₂O (5 mL) and brine (5 mL), dried with Na2SO4 and concentrated. The remaining NMP was removed under a stream of N2 at rt. Flash chromatography with a gradient from 1:1 hexanes/ EtOAc to 2:1 EtOAc/hexanes followed by pTLC eluting with 2:1 EtOAc/hexanes afforded isomer 1RS (4.0 mg, 71%) a white wax.

Isomer 1RS: 1H NMR (C6D6, 400 MHz) δ 6.23 (dd, J=14.7, 10.9 Hz, 1H), 6.08 (d, J=10.6 Hz, 1H), 5.82 (dd, J=15.2, 9.7 Hz, 1H), 5.61 (dd, J=15.2, 10 Hz, 1H), 5.51 (dd, J=15, 8.8 Hz, 1H), 5.24 (d, J=10.2 Hz, 2H), 3.62 (d, J=11 Hz, 1H), 3.49 (bs, 1H), 3.22 (s, 3H), 3.20-3.07 (m, 3H), 2.88 (dd, J=8.0, 2.1 Hz, 1H), 2.67 (dd, J=5.4, 2.1 Hz, 1H), 2.42-2.33 (m, 2H), 2.28-2.14 (m, 3H), 1.61 (s, 3H), 1.60-1.49 (m, 5H), 1.42-1.11 (m, 8H), 1.06 (d, J=6.8 Hz, 3H), 1.00 (s, 3H), 0.88 (d, J=6.8 Hz, 3H), 0.83 (t, J=7.29 Hz, 3H), 0.70 (d, J=6.8 Hz, 3H); 13C NMR (C6D6, 100 MHz) δ 171.9, 168.7, 140.4, 137.7, 131.3, 131.3, 126.2, 126.2, 83.4, 82.3, 79.0, 74.9, 73.1, 69.1, 59.8, 58.7, 57.5, 41.8, 41.0, 38.9, 38.3, 35.6, 30.1, 24.5, 23.6, 20.5, 16.2, 11.7, 14.2, 10.3, 9.8; FTIR (film) vmax 3447, 2962, 2927, 2875, 1734, 1457, 1374, 1240, 1176, 1082, 1021 cm-1; ESI-MS m/z 292.79 [M+Na]+; HR-ESI-MS m/z calcd. for C18H22O2Na1 [M+Na]+: 293.1512. found 293.1513.

Example 33

E. Synthesis of isomer 1RR. A three-step procedure was used to prepare isomer 1RR. This began by preparation of alkyne 24c from aldehyde 8 and allenylstannane 23a. Hydrostannylation of 24c afforded stannane S11c, which not characterized and used immediately after preparation. Stannane S11c was coupled to core 21 to afford isomer 1SS.

Example 34

(1R,2R)-1-((2R,3R)-3-((2R,3S)-3-methoxypentan-2-yl) oxiran-2-yl)-2-methylbut-3-yn-1-ol (24c). SnCl4 (112.0 mg, 430.0% mol) was added in a dropwise fashion over 1 min to a solution of allenylstannane 23a8 (149.0 mg, 434.2% mol) in hexane (2 mL) at 0° C. After 3 h at 0° C., the solution was cooled to −78° C. At −78° C., aldehyde 8 (50.0 mg, 290.0% mol) in hexane (2 mL) was added dropwise over 2 min. After 2 h at −78° C., satd. NaHCO3 (5 mL) was added and the mixture warmed to rt. The layers were separated and the aqueous layer extracted with EtOAc (3×5 mL). The organic layers were combined, washed with brine (5 mL), dried with Na2SO4, filtered and concentrated. Flash chromatography with a gradient from 4:1 hexanes/EtOAc to provided alkyne 24c (66.0 mg, 83%) as a clear oil.

Alkyne 24c: TLC (2:1 hexanes/EtOAc): Rf=0.50; 1H NMR (CDCl3, 400 MHz) δ 3.41 (s, 3H), 3.41 (m, 1H), 3.21 (ddd, J=10.4, 6.4, 3.9 Hz, 1H), 3.07 (dd, J=4.6, 2.3 Hz, 1H), 3.0 (dd, J=8.1, 2.2 Hz, 1H), 2.67 (m, 1H), 2.16 (d, J=2.5 Hz, 1H), 2.07 (bs, 1H), 1.72-1.42 (m, 3H), 1.31 (d, J=6.9 Hz, 3H), 0.97 (d, J=7.0 Hz, 3H), 0.90 (t, J=7.4 Hz, 3H); 13C NMR (CDCl3, 100 MHz) δ 83.8, 77.4, 73.7, 71.2, 59.5, 59.4, 58.3, 39.0, 31.1, 23.9, 17.2, 10.4, 10.2; ESI-MS m/z 249.14 [M+Na]+; FTIR (film) vmax 3430, 3310, 2967, 2935, 2878, 1457, 1379, 1260, 1093 cm-1; HR-ESI-MS m/z calcd. for C13H22O3Na1 [M+Na]+: 249.1461. found 249.1462.

Example 35

(1R,2R,E)-1-((2R,3R)-3-((2R,3S)-3-Methoxypentan-2-yl)oxiran-2-yl)-2-methyl-4-(tributylstannyl)but-3-en-1-ol (S11c). n-Bu3SnH (61.0 mg, 210.0% mol) was added in a dropwise fashion to a solution of alkyne 24d (310 mg, 137.0% mol) and PdCl2 (PPh3)2 (4.5 mg, 6.4% mol) in THF (5 mL) cooled to 0° C. This mixture was warmed to rt. After 15 min at rt, the alkyne was consumed as indicated by TLC analysis. The solution was concentrated and filtered quickly through a plug of silica gel deactivated with Et3N to afford S11c (53 mg, 79%), as a light yellow oil, which was used immediately after preparation.

Isomer 1RR (FD-895). Pd2(dba)3 (2.1 mg, 2.2 mmol), Ph3As (6.4 mg, 21.0% mol), and LiCl (1.3 mg, 31.0% mol) were added sequentially to a solution of vinyl iodide 21 (5 mg, 10.7% mol) and the crude stannane S11c (8.0 mg, 15.4% mol) in dried and degassed NMP (1 mL). The reaction was stirred for 24 h at which point an additional Pd2(dba)3 (2.0 mg, 2.0 mmol) and Ph3As (6.4 mg, 21.0% mol) were added. After stirring for an additional 24 h at rt, H2O (3 mL) was added and the mixture was extracted with EtOAc (3 #5 mL). The organic layers were combined, washed with H2O (5 mL) and brine (5 mL), dried with Na2SO4 and concentrated. The remaining NMP was removed under a stream of N2 at rt. Flash chromatography with a gradient from 1:1 hexanes/EtOAc to 2:1 EtOAc/ hexanes followed by pTLC eluting with 2:1 EtOAc/hexanes afforded isomer 1RR (4.0 mg, 71%) as a white wax.

Isomer 1RR (FD-895): 1H NMR (C6D6, 400 MHz) δ 6.23 (dd, J=14.7, 10.9 Hz, 1H), 6.08 (d, J=10.6 Hz, 1H), 5.82 (dd, J=15.2, 9.7 Hz, 1H), 5.61 (dd, J=15.2, 10 Hz, 1H), 5.51 (dd, J=15, 8.8 Hz, 1H), 5.24 (d, J=10.2 Hz, 2H), 3.62 (d, J=11 Hz, 1H), 3.49 (bs, 1H), 3.24 (s, 3H), 3.14 (dd, J=10.4, 6.3 Hz, 1H), 3.10-3.03 (m, 1H), 2.86 (dd, J=8.2, 2.1 Hz, 1H), 2.65 (dd, J=5.6, 2.1 Hz, 1H), 2.43-2.34 (m, 3H), 2.31-2.17 (m, 3H), 1.89 (bs, 1H), 1.77 (bs, 1H), 1.61 (s, 3H), 1.56 (s, 3H), 1.40-1.14 (m, 9H), 1.0 (s, 3H), 0.83 (m, 6H), 0.69 (d, J=6.8, 3H); 13C NMR (C6D6, 100 MHz) δ 171.9, 168.7, 140.4, 138.0, 131.4, 131.4, 126.2, 126.0, 83.4, 82.4, 79.0, 74.9, 73.1, 69.1, 60.3, 59.4, 57.5, 42.4, 40.9, 39.1, 38.3, 35.6, 30.1, 24.5, 23.7, 20.5, 16.8, 16.2, 11.6, 10.4, 9.8; FTIR (film) vmax 3446, 2957, 1733, 1368, 1251, 1169 cm-1; ESI-MS m/z 292.79 [M+Na]+; HR-ESI-MS m/z calcd. for C18H22O2Na1 [M+Na]+: 293.1512. found 293.1513.

Example 36

Synthesis of isomer 1SR. A three-step procedure was used to prepare isomer 1SR. This began by preparation of alkyne 24d from aldehyde 8 and allenylstannane 23b. Hydrostannylation of 23 d afforded stannane S11d, which not characterized and used immediately after preparation. Stannane S11d was coupled to core 21 to afford isomer 1SS. BF3.Et2O (220.0% L, 1.8 mmol) was added in a dropwise fashion over 5 min to a solution of aldehyde 8 (100.0 mg, 580.0% mol) and allenylstannane 23b8 (300.0 mg, 874.0% mol) in dry CH2Cl2 (3 mL) cooled to −78° C. The reaction was stirred for 1 h at −78° C. A mixture of MeOH (2.6 mL) and satd. NaHCO3 (0.3 mL) was added and the mixture was warmed to rt. The layers were separated and the aqueous layer extracted with ether (3 #20 mL). The organic layers were combined, washed with brine and dried with Na2SO4 and concentrated. Flash chromatography with a gradient from hexanes to 4:1 hexanes/EtOAc afforded alkyne 24d (105.0 mg, 80%) as a clear oil.

Alkyne 24d: TLC (2:1 hexanes/EtOAc): Rf=0.50; 1H NMR (CDCl3, 400 MHz) δ 3.71 (dd J=6.9, 3.2 Hz, 1H), 3.40 (s, 3H), 3.18 (q, J=6.2, 5.2 Hz, 1H), 3.10 (t, J=2.7 Hz, 1H), 3.04 (dd, J=8.0, 2.1 Hz, 1H), 2.60 (dq, 1H), 2.18 (bs, 1H), 2.15 (d, J=1.9 Hz, 1H), 1.65 (sep., 1H), 1.54-1.44 (m, 2H), 1.31 (d, J=6.9 Hz, 3H), 0.96 (d, J=7.0 Hz, 3H), 0.90 (t, J=7.4 Hz, 3H); 13C NMR (CDCl3, 100 MHz) δ 84.9, 83.9, 71.2, 71.1, 58.6, 58.3, 57.0, 38.8, 30.6, 23.9, 17.1, 10.6, 10.2; FTIR (film) vmax 3438, 3310, 2973, 2937, 2879, 1457, 1090 cm-1; HR-ESI-MS m/z calcd. for C13H22O3Na1 [M+Na]+: 249.1461. found 249.1460.

Example 37

(1S,2R,E)-1-((2R,3R)-3-((2R,3S)-3-Methoxypentan-2-yl)oxiran-2-yl)-2-methyl-4-(tributylstannyl)but-3-en-1-ol (S11d). n-Bu3SnH (76.0 mg, 260.0% mol) was added in a dropwise fashion to a solution of alkyne 24d (50.0 mg, 220.0% mol) and PdCl2 (PPh3)2 (8.0 mg, 11.4% mol) in THF (5 mL) cooled to 0° C. This mixture was warmed to rt. After 15 min at rt, the alkyne was consumed as indicated by TLC analysis. The solution was concentrated and filtered quickly through a plug of silica gel deactivated with Et3N to afford S11d (68.0 mg, 60%), as a light yellow oil, which was used immediately after preparation.

Isomer 1SR. Pd2(dba)3 (2.0 mg, 2.1% mol), Ph3As (6.4 mg, 20.8% mol), and LiCl (1.3 mg, 31.0% mol) were added sequentially to a solution of vinyl iodide 21 (5.0 mg, 10.7 mmol) and crude stannane Slld (8.0 mg, 15.0% mol) in dried and degassed NMP (1 mL). The reaction was stirred for 24 h at which point an additional Pd2(dba)3 (2.0 mg, 2.1% mol) and Ph3As (3.2 mg, 10.4% mol) were added. After stirring for an additional 24 h at rt, H2O (3 mL) was added and the mixture was extracted with EtOAc (3×5 mL). The organic layers were combined, washed with H2O (5 mL) and brine (5 mL), dried with Na2SO4 and concentrated. The remaining NMP was removed under a stream of N2 at rt. Flash chromatography with a gradient from 1:1 hexanes/EtOAc to 2:1 EtOAc/hexanes followed by pTLC eluting with 2:1 EtOAc/hexanes afforded isomer 1SR (4.0 mg, 71%) a white wax.

Isomer 1SR: 1H NMR (C6D6, 400 MHz) δ 171.9, 168.7, 140.4, 138.1, 131.4, 131.3, 126.2, 125.8, 83.5, 82.4, 79.0, 73.1, 71.9, 69.1, 58.9, 57.4, 57.0, 41.6, 40.9, 38.9, 38.3, 35.6, 29.9, 24.5, 23.7, 20.5, 16.2, 16.1, 11.6, 10.6, 9.8; 13C NMR (C6D6, 100 MHz) δ 172.1, 169.0, 140.7, 137.9, 132.5, 132.4, 131.7, 131.3, 126.4, 126.4, 83.7, 82.6, 79.2, 73.3, 72.9, 69.3, 59.6, 57.7, 57.7, 41.5, 41.1, 39.3, 38.5, 35.8, 32.4, 30.3, 30.1, 29.8, 24.8, 23.9, 23.1, 20.7, 17.2, 16.4, 14.4, 11.9, 10.8, 10.0; FTIR (film) vmax 3447, 2963, 2930, 2875, 1739, 1457, 1374, 1239, 1176, 1089, 1021 cm-1; [M+Na]+; HR-ESI-MS m/z calcd. for C31H50O9Na1 [M+Na]+: 589.3345. found 589.3347.

Example 38

NMR studies on isomeric C16-C17 isomers. Copies of 1H NMR, 13C-NMR as well as select 2D NMR experiments isomers 1SS, 1RS, 1RR and 1SR and synthetic FD-895 (1) have been provided in the accompanying supporting information spectral data file.

Example 39

FD-895 (1a) undergoes hydrolysis under neutral conditions to afford a mixture of acids 3a-3c.3 As determined by NMR monitoring (FIG. 3), this reaction occurs with the formation of 3a, 3b and 3c in an approximated 3:2:5 ratio, suggesting the hydrolysis occurs via non-selective addition of water to an incipient allylic cation. While not unexpected, the products of this reaction demonstrate a loss of activity with the reaction mixture at 216 h demonstrating an IC50 value of 11.2±1.4 µM in HCT-116 cells.21 See FIG. 18. Based on this observation, we turned our efforts to apply conventional SAR techniques to identify analogs with improved stability.

Example 40

Scheme 1. Synthesis of cyclopropane analogs 7a-7b.[a]

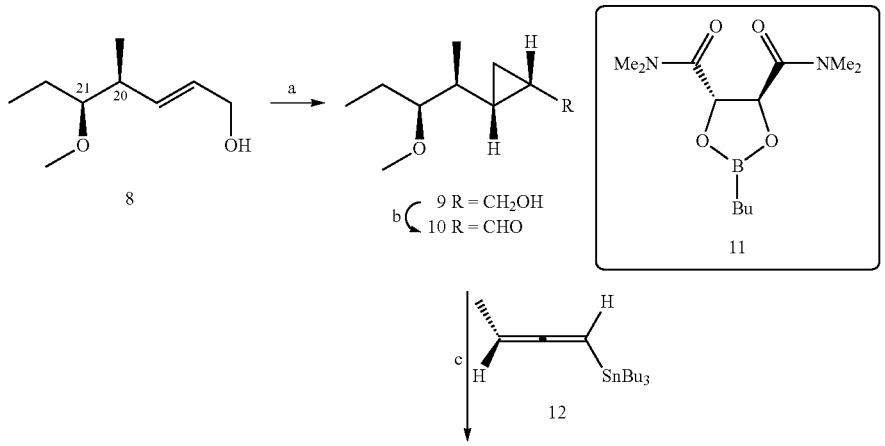

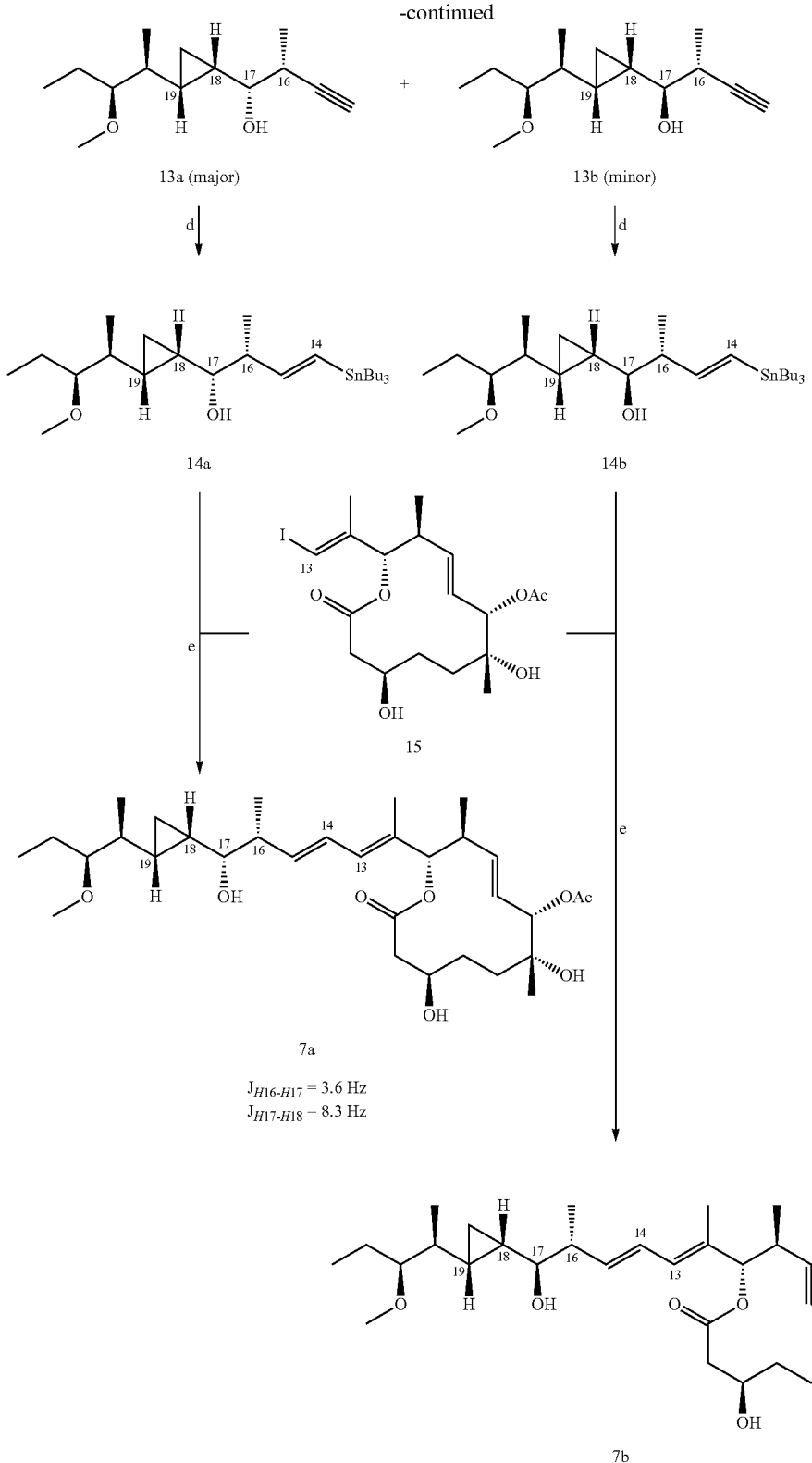
Reagents and conditions: (a) 11, Zn, CH$_2$I$_2$, DME, -10° C. to rt, 83%; (b) Dess-Martin periodinane, CH$_2$Cl$_2$, rt, 80%; (c) 12, BF$_3$•Et$_2$O, CH$_2$Cl$_2$, 80% of a 3:2 mix of 13a:13b; (d) PdCl$_2$(PPh$_3$)$_2$, (n-Bu)$_3$SnH, THF, 44% for 14a or __% for 14b; (e) Pd$_2$(dba)$_3$, AsPh$_3$, LiCl, NMP, 71% for 7a or __% for 7b.

Aldehyde 10 served as a central building block. Using Marshall methods[22] demonstrated in our prior synthesis of FD-895,[3] addition of allenylstannane 12 to aldehyde 10 afforded 143a (major isomer) along with 13b (minor isomer).[3] Fortunately, these materials were chromatographically separable. The assignment of these two isomers was validated by coupling constant analyses, which confirmed the corresponding assignments in 14a

Example 41

All oligos-nucleotides were custom synthesized by Integrated DNA Technologies (Skokie, Ill., USA). Pladienolide B (PLAD) and FD-895 obtained from Dr. Michael Burkart, Department of Chemistry, University of California, San Diego. Fludarabine phosphate (F-Ara-A, catalog #F2773) and Bendamustine (Catalog #B5437) were purchased from Sigma-Aldrich.

Example 42

Cell Line Culture

The leukemia cell lines, MEC1, RAJI and JURKAT were maintained in CLL B cells were maintained in RPMI 1640 medium supplemented with 10% FBS, 2 mM L-glutamine, and 100 U/mL of penicillin and 100 µg/mL of streptomycin at 37° C. in an atmosphere of 5% CO2.

Example 43

Chronic Lymphocytic Leukemia-Samples and Cell Culture Conditions

Peripheral blood mononuclear cells (PBMC) from patients with CLL were obtained from the CLL Research Consortium (CRC) tissue bank. The blood samples were collected after obtaining a written informed consent from the patients under a protocol approved by the institutional review board of The University of California, San Diego. All patients met criteria for CLL.[1] CLL B cells and PBMCs were separated from heparinized venous blood of the B-CLL patients by density gradient centrifugation using Ficoll-Hypaque (GE healthcare) as described earlier.[2] The samples that were used had more than 95% positive cells for CD19 and CD5+, as assessed by flow cytometry. CLL B cells were maintained in RPMI 1640 medium supplemented with 10% FBS, 2 mM L-glutamine, and 100 U/mL of penicillin and 100 µg/mL of streptomycin at 37° C. in an atmosphere of 5% CO2.

Example 44

Normal B Cell Isolation

Normal B cells were purified from buffy coats of healthy volunteers, obtained from San Diego blood bank. Positive isolation with Dynabeads® CD19 pan B and DETACHa-BEAD CD19 (Invitrogen Life Technologies, USA) were used to achieve more than 95% purity by flow cytometry analysis.

Example 45

Flow Cytometry Analysis

Apoptotic and viable cells were discriminated via flow cytometry of cells stained with 3,3' dihexyloxacarbocyanine iodide ($DiOC_6$) (Molecular Probes, Eugene, Oreg., USA) and propidium iodine (Sigma, St Louis, Mo., USA), as described.[3] Using this method viable cells exclude PI and stain brightly positive for $DiOC_6$.

Example 46

RT-PCR Analysis

CLL cells were treated with 10 and 100 nM of FD-895 and PLAD, 33 and 100 µM of bendamustine and 3, 10, and 33 µM of F-Ara-A for 4 h. Normal B and CLL cells were treated with 100 nM of FD-895 and PLAD and 10 µM of F-Ara-A for 15 minutes, 30 minutes, 1, 2 and 4 h. Total RNA was extracted using mirVana™ miRNA isolation kit (Ambion Life Technology, USA). After DNase treatment, 200 ng total RNA was reverse-transcribed using a SuperScript™ III first-strand synthesis system (Invitrogen). PCR was performed on 10 ng of the obtained cDNA (or human genomic DNA as a control) in 25 µl of reaction mixture containing Plantinum® PCR SuperMix High-fidelity (Invitrogen Life Technology, USA), and 0.1 µM of each primer of the appropriate pair.

PCR conditions were 94° C. for 3 min; 35 cycles of 94° C. for 30 s, 60° C. for 30 s, and 72° C. for 1 min; followed by 72° C. for 5 min. PCR products were separated on a 2% agarose gel and stained with ethidium bromide.

Example 47

Quantitative RT-PCR Analysis

CLL cells were treated with 100 nM of FD-895 and PLAD and 10 µM of F-Ara-A for 15 minutes, 1 and 4 h. Normal B and CLL cells were treated with 10, 100, and 1000 nM of FD-895 and PLAD and 10 µM of F-Ara-A for 4 h.

Extraction of total RNA and cDNA synthesis were performed as described earlier. Unspliced mRNA was quantified using a 7900HT fast Real Time PCR System (Applied Biosystems). The amounts of unspliced mRNA of DNAJB1, and RIOK3 were determined by SYBR green (Power SYBR Green PCR Master Mix, Applied Biosystems) real-time quantitative RT-PCR using specific primers designed for the intron of each gene (see additional information section at the end).

PCR using 0.2 µM of each primer was performed on 20 ng of the obtained cDNA. PCR conditions were 50° C. for 2 min; 95° C. for 10 min; 35 cycles of 94° C. for 20 s, 55° C. for 20 s, followed by 72° C. for 30 s. The mRNA levels were calculated using $2^{-\Delta\Delta C_T}$ method.[4] GAPDH was used as a control for normalization.

Example 48

Figure 19:
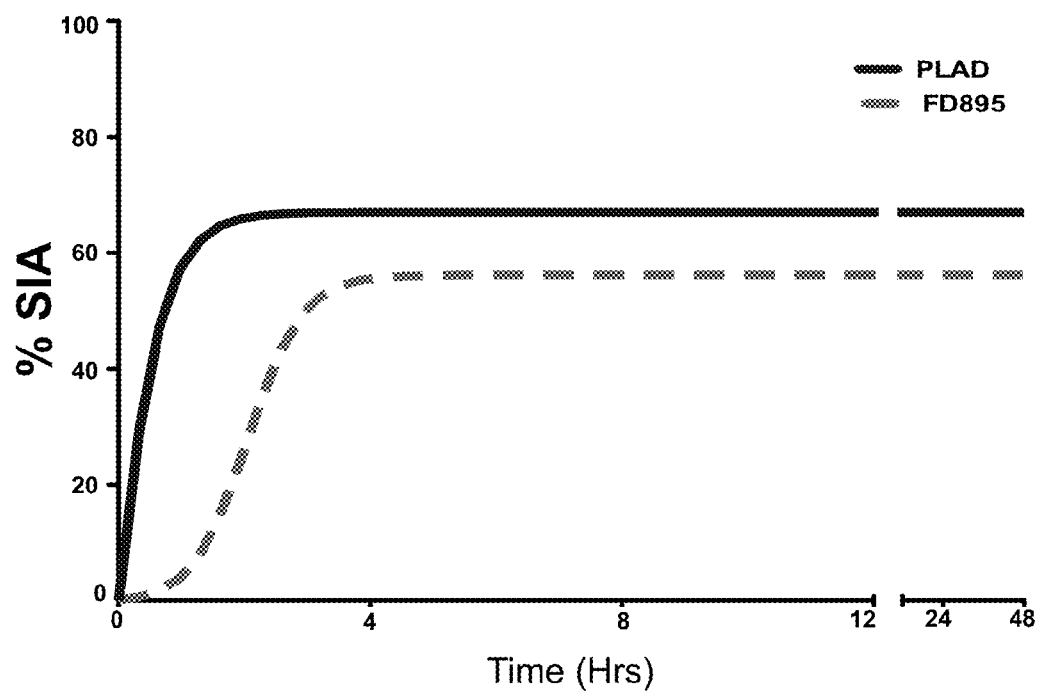
FIG. 19: FD-895 and PLAD induce apoptosis in CLL cells at short time of incubation: Primary leukemia B cells from CLL patient incubated with FD-895 and PLAD with 100 nM. The samples were harvested at different time points (0, 2, 4, 8, 12, 24 and 48 hours) and % SIA was measured by flow cytometry as described above. This result was produced 3 times independently.

Washout Experiment and Testing of FD-895 and PLAD to Test Capability to Induce Apoptosis in CLL Cells at Short Time of Incubation We tested the effect of FD-895 and PLAD with 100 nM in CLL cells in a time dependent manner to know what will be minimum time to induce apoptosis in CLL cells. We harvested the treated CLL cells at different time period viz. 0, 2, 4, 8, 12, 24 and 48 hours. We measured the % specific induced apoptosis (% SIA) by using flow cytometry and observed that both compounds showed apoptosis in CLL cells within 2 hours of incubation period (FIG. 19).

Example 49

FD-895 and PLAD Induce Apoptosis in CLL Cells but not in Normal Lymphocytes with a Tp53 Independent Activity We examined whether FD-895, PLAD and chemokine like F-Ara-A with 0, 10, 100, 1000 or 10,000 nM could induce apoptosis of CLL patients with del (17p) and Tp53 mutation or B cells from healthy donors. We measured the % specific induced apoptosis (% SIA) by using flow cytometry and observed that CLL patients with del (17p) showed resistance to F-Ara-A while FD-895 and PLAD could induce significant killing of CLL B cells (FIG. 2A) within 48 hours.

Figure 20:
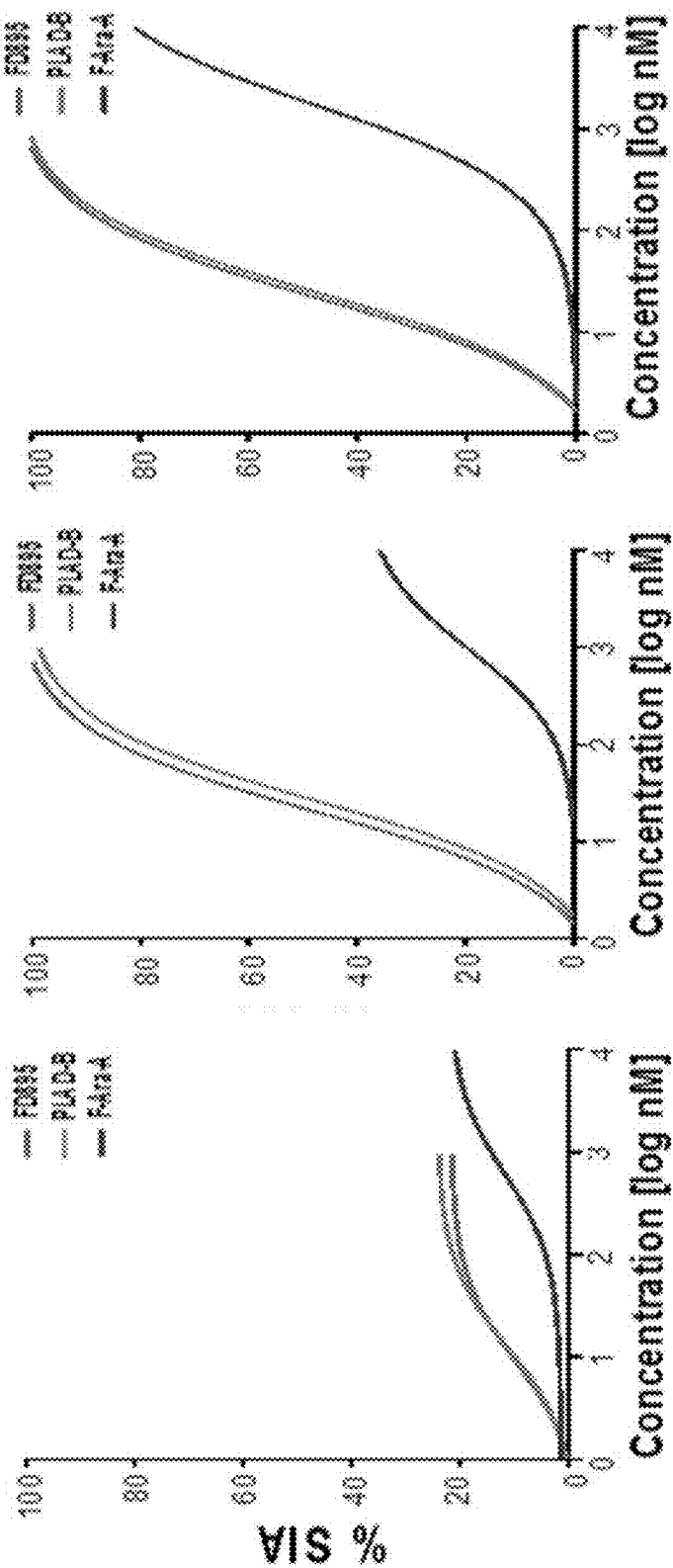
FIG. 20A-20C: FD-895 and PLAD induce apoptosis in CLL cells but not in normal lymphocytes with a TP53 independent activity: Primary leukemia B cells from CLL (FIG. 20A) patient with del (17p) and Tp53 mutation, (FIG. 20B) patient with wild type p53 and sensitive to F-Ara-A and (FIG. 20C) normal lymphocytes from healthy donor were incubated with FD-895, PLAD and F-Ara-A (0, 10, 100, 1000 10,000 nM) for 48 hours. The samples were harvested at 48 hours. % specific induced apoptosis (% SIA) was measured by flow cytometry using propidium iodine (PI) exclusion and mitochondrial membrane potential changes using DiOC$_6$. CLL cells from patient with del (17p) and Tp53 mutation showed resistance to F-Ara-A with IC$_{50}$>10 µM but high sensitive to FD-895 and PLAD with IC$_{50}$ in the range of 10-50 nM (A). CLL cells from patient with wild type p53 and sensitive to F-Ara-A showed also sensitive to FD-895 and PLAD with IC$_{50}$<3 nM (B). Normal B lymphocytes from healthy donor showed very low sensitive to these compounds (C).

CLL patients with Tp53 mutation also showed significant death of CLL B cells treated with FD-895, PLAD and F-Ara-A for 48 hours. These effects were dose dependent. On the other hand, FD-895, PLAD and F-Ara-A did not induce significant apoptosis of B cells from healthy donors after 48 hours (FIG. 20C).

Example 50

Figure 21:
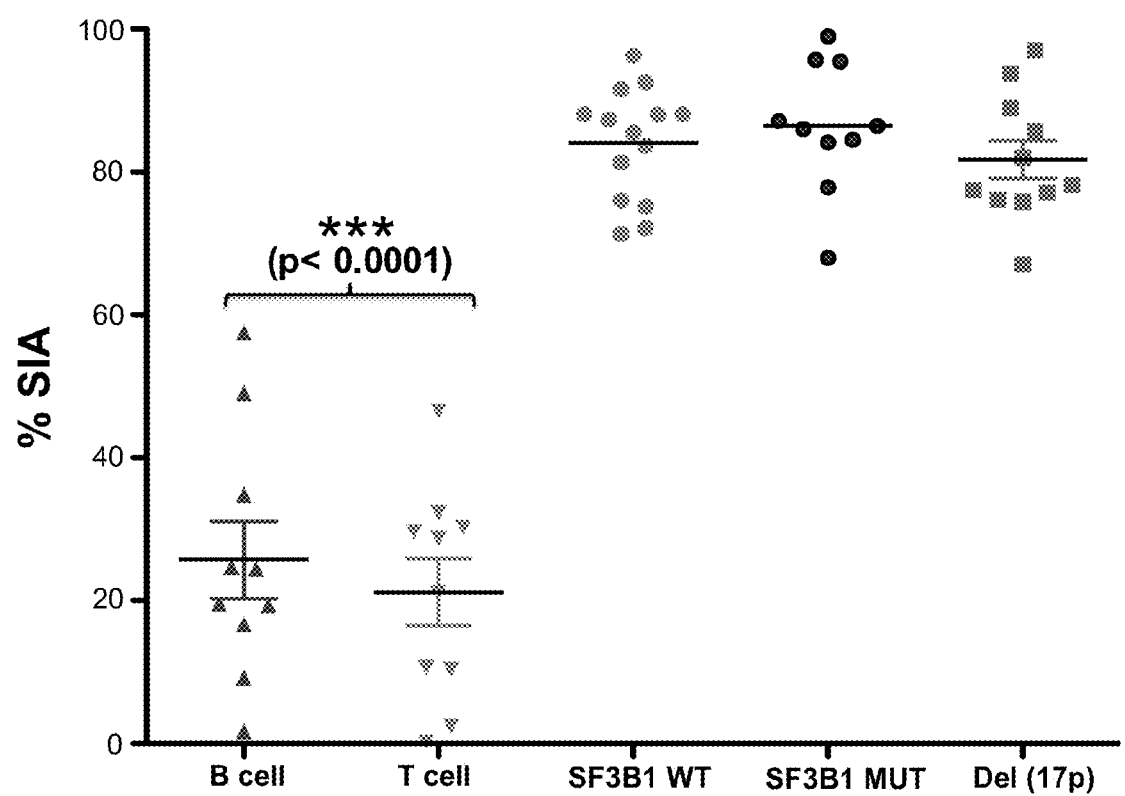
FIG. 21: FD-895 and PLAD induce apoptosis in CLL cells not ONLY independently of Tp53 but also independently of SF3B1 mutational status: Primary leukemia B cells from CLL patient with SF3B1 wild, SF3B1 mutation, 17p DEL and normal B and T lymphocytes from healthy donor were incubated with FD-895 and PLAD with 100 nM for 48 hours. After incubation, the samples were harvested and % SIA was measured by flow cytometry as described above. FD-895 and PLAD (PLAD data not shown) induced apoptosis in 17p deletion (Tp53) or SF3B1 mutation status while normal B or T cells did not show significant apoptosis. Each dots represents number of CLL patient sample and normal B or T cells. The data shows the results of samples analyzed in duplicates with S.D.

FD-895 and PLAD Induce Apoptosis in CLL Cells not Only Independently of Tp53 but Also Independently of SF3B1 Mutational Status We also tested whether FD-895 and PLAD with 100 nM could induce apoptosis of CLL patients with SF3B1 wild, mutation, 17pDEL or normal B and T cells. We found that CLL patients with SF3B1 wild, mutation or 17pDEL induce significant cells death after 48 hrs with 100 nM of FD-895 (FIG. 2) and PLAD, while normal B or T cells from healthy donors did not induce significant cell death (FIG. 21).

TABLE 2

List of cell lines used in the study for testing of FD-895/Pladienolide-B and Fludarabine (F-Ara-A) with their characteristics

| S. NO. | Name of Cell Line | Type of Cell Line | p53 Status |
|---|---|---|---|
| 1. | RAJI | Burkitt's lymphoma | Wild Type |
| 2. | Jurkat | T-cell Leukemia | Mutant |
| 3. | MEC1 | Chronic Lymphocytic Leukemia | Mutant |

Example 51

Activity of FD-895, PLAD and F-Ara-A in Different Human Leukemia Cell Lines

Figure 22:
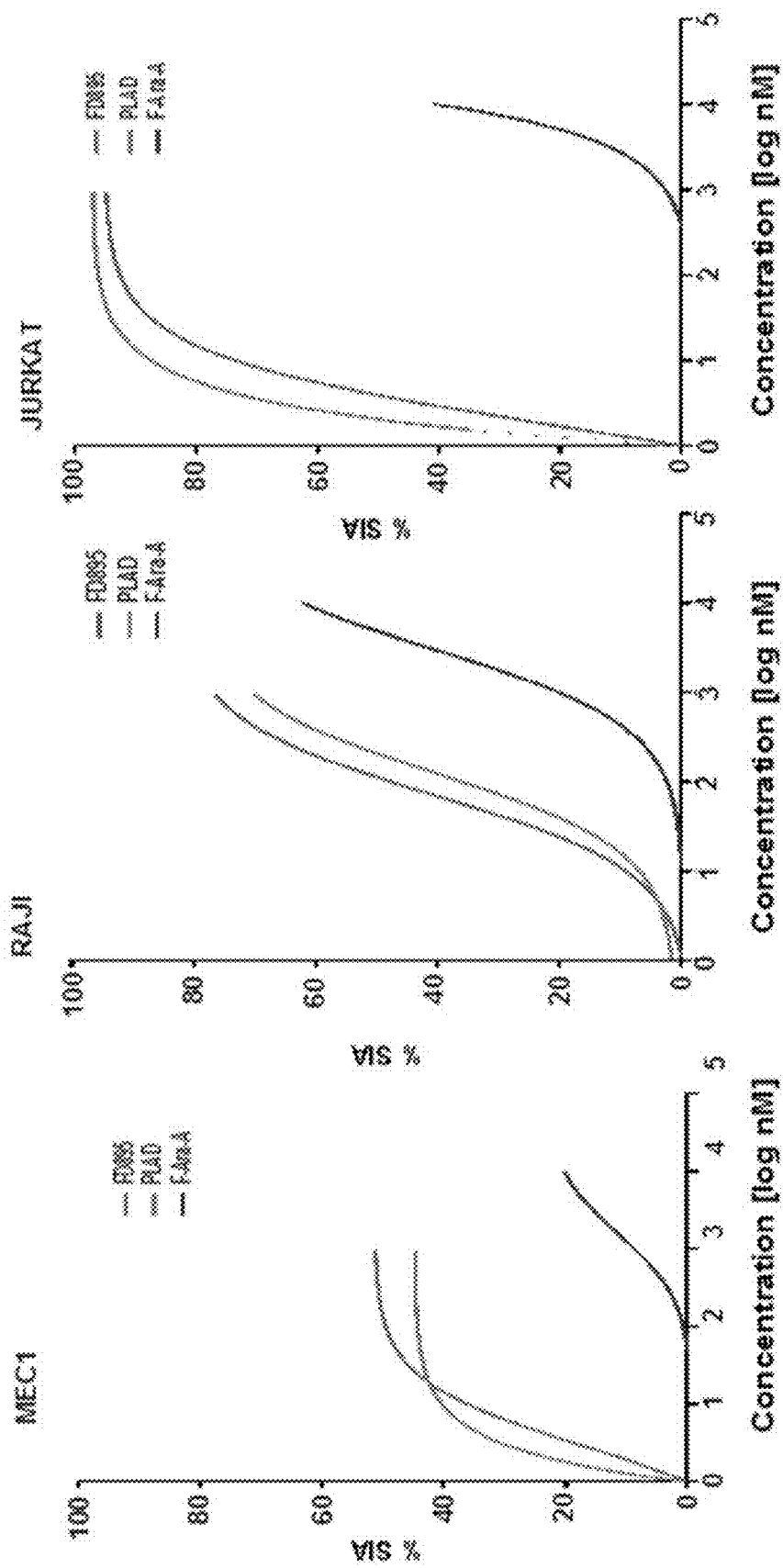
FIG. 22: Activity of FD-895, PLAD and F-Ara-A in different human leukemia cell lines: Different leukemia cell lines including MEC1, RAJI and JURKAT were incubated with FD-895, PLAD and F-Ara-A (0, 10, 100, 1000, 10,000 nM) for 48 hours. The samples were harvested and cell viability was measured by flow cytometry using propidium iodine (PI) exclusion and mitochondrial membrane potential changes using DiOC$_6$. This experiments was performed 2 times independently.

We further examined the activity of FD-895, PLAD and F-Ara-A in different leukemia cell lines like MEC1 (B chronic lymphocytic leukemia cell line), RAJI (B lymphocyte cell line), JURKAT (T lymphocyte cell line) as to know whether these compounds induce apoptosis or not. We incubated cells with FD-895, PLAD and F-Ara-A with 0, 10, 100, 1000 or 10,000 nM for 48 hours and measured the % SIA by using flow cytometry. Both FD-895 and PLAD showed high significant cell death in JURKAT and RAJI cell lines while these compounds did not show significant apoptosis in MEC1 cell line. F-Ara-A treated RAJI cell line showed significant cell death but JURKAT and MEC1 did not show significant % of cell death (FIG. 22)

Example 52

Figure 23:
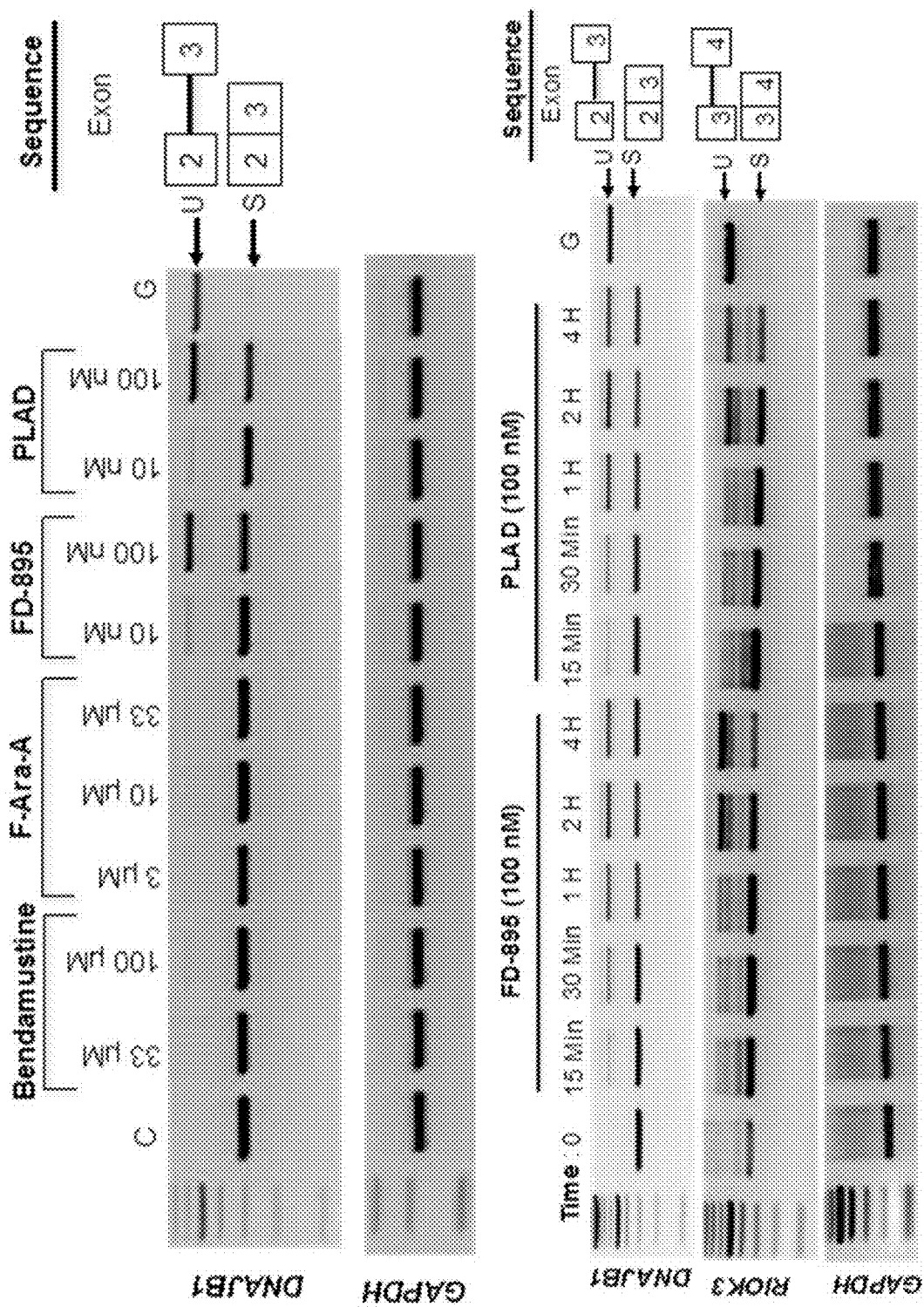
FIG. 23: FD-895 and PLAD induced inhibition of splicing in CLL: RT-PCR for analysis of spliced and unspliced mRNAs. CLL cells treated with FD-895, PLAD (10, 100 nM), chemotherapeutic agent like bendamustine (33, 100 µM) and F-Ara-A (3, 10, 33 µM) for 4 hours. RT-PCR for DNAJB1 was performed with primers spanning two exons; products were analyzed on ethidium bromide-stained agarose gels (2%) to visualize the correct size of the unspliced mRNAs. The upper and lower panel showed RT-PCR product of DNAJB1 and GAPDH respectively. The exon structure of DNAJB1 gene is indicated. G, human genomic DNA was used as a control; U, unspliced mRNA; S, spliced mRNA.

FD-895 and PLAD but not Chemotherapy Agents Induce Intron Retention (Spliceosome Inhibition) in CLL To examine whether FD-895, PLAD and chemotherapy agents induced intron retention in in CLL cells, we treated CLL cells (>90% viable cells) with FD-895, and PLAD (10, 100 nM), bendamustine (33, 100 μM) and F-Ara-A (3, 10, 33 μM) for 4 hours. Total RNA extracted from treated and non-treated CLL cells (control) and cDNA was synthesized. RT-PCR for DNAJB1 and GAPDH (housekeeping gene) was performed. Conventional RT-PCR confirmed both FD-895 and PLAD showed intron retention at low concentration while chemotherapy agents (F-Ara-A and Bendamustine) did not show intron retention/splicing inhibition even at supra-physiological concentration (FIG. 5). Neither FD-895, PLAD nor chemotherapy agents showed splicing inhibition of housekeeping gene, GAPDH (FIG. 23).

Example 53

FD-895 and PLAD Induce Rapid Intron Retention in CLL

Figure 24:
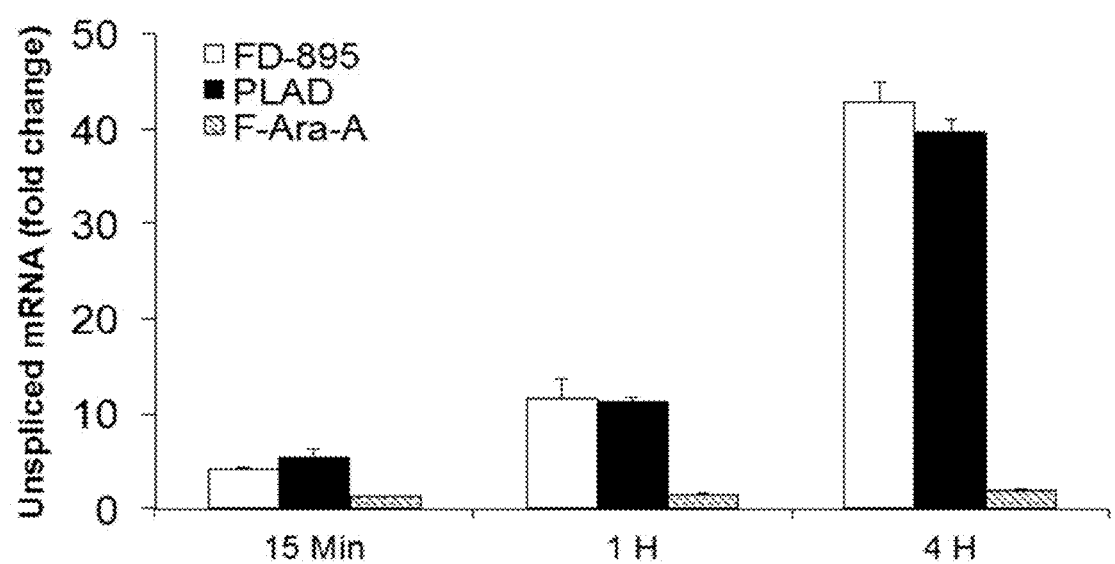
FIG. 24: Time-dependent increase of unspliced mRNA by FD-895 and PLAD in CLL: CLL cells were treated with 100 nM of FD-895 and PLAD and 10 µM of F-Ara-A for 15 min, 1 and 4 hours. Quantitative RT-PCR using primers specific for each intron quantified unspliced mRNA for DNAJB1. GAPDH was used for normalization. This result validated three times independently. Error bars indicate S.D.

To investigate, what will be an early time point for intron retention/splicing inhibition by FD-895 and PLAD, we treated CLL cells (>90% viable cells) with FD-895 and PLAD (100 nM) for 15 min, 30 min 1, 2 and 4 hours and performed RT-PCR for DNAJB1, RIOK3 and GAPDH. We observed that both FD-895 and PLAD induced splicing impairment of DNAJB1 and RIOK3 within 15 minutes of treatment while there was no intron retention/splicing inhibition of housekeeping gene, GAPDH (FIG. 24).

Example 54

Figure 6:
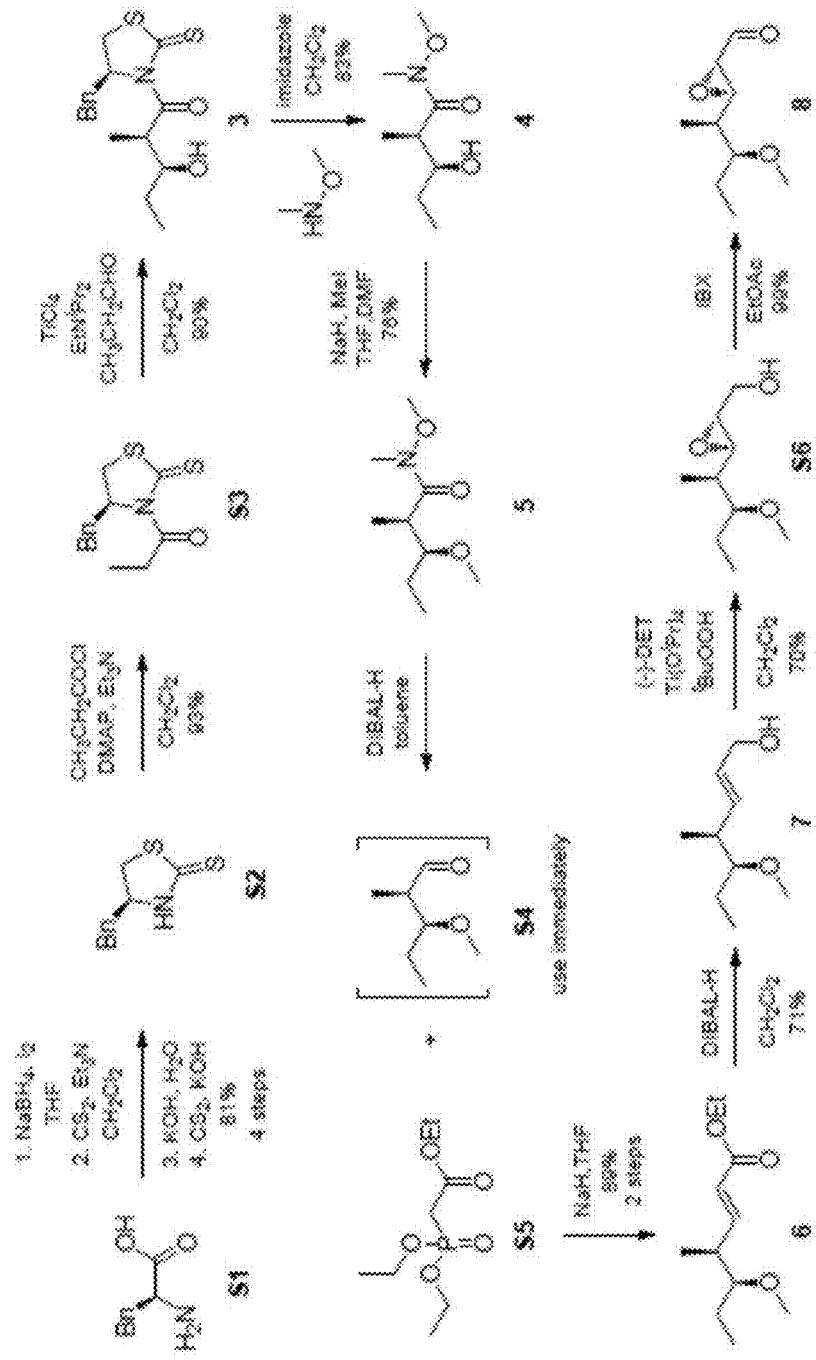
FIG. 6: Synthetic scheme of keystone portion of synthetic derivatives of FD-895.

Time-Dependent Increase in Unspliced mRNA by FD-895 and PLAD but not by F-Ara-A in CLL To quantify unspliced mRNA levels by FD-895, PLAD and F-Ara-A, we treated CLL cells with FD-895, PLAD (100 nM) and F-Ara-A (10 μM) for 15 min, 1 and 4 hours and performed quantitative RT-PCR for DNAJB1. Quantitative RT-PCR analysis showed the time dependent disturbance of splicing with FD-895, PLAD and F-Ara-A (FIG. 6). At different time point of treatment, FD-895 and PLAD showed gradual increase in unspliced mRNA of DNAJB1 while F-Ara-A treated CLL cells did not show increase in unspliced mRNA of DNAJB1 (FIG. 25).

Figure 7:
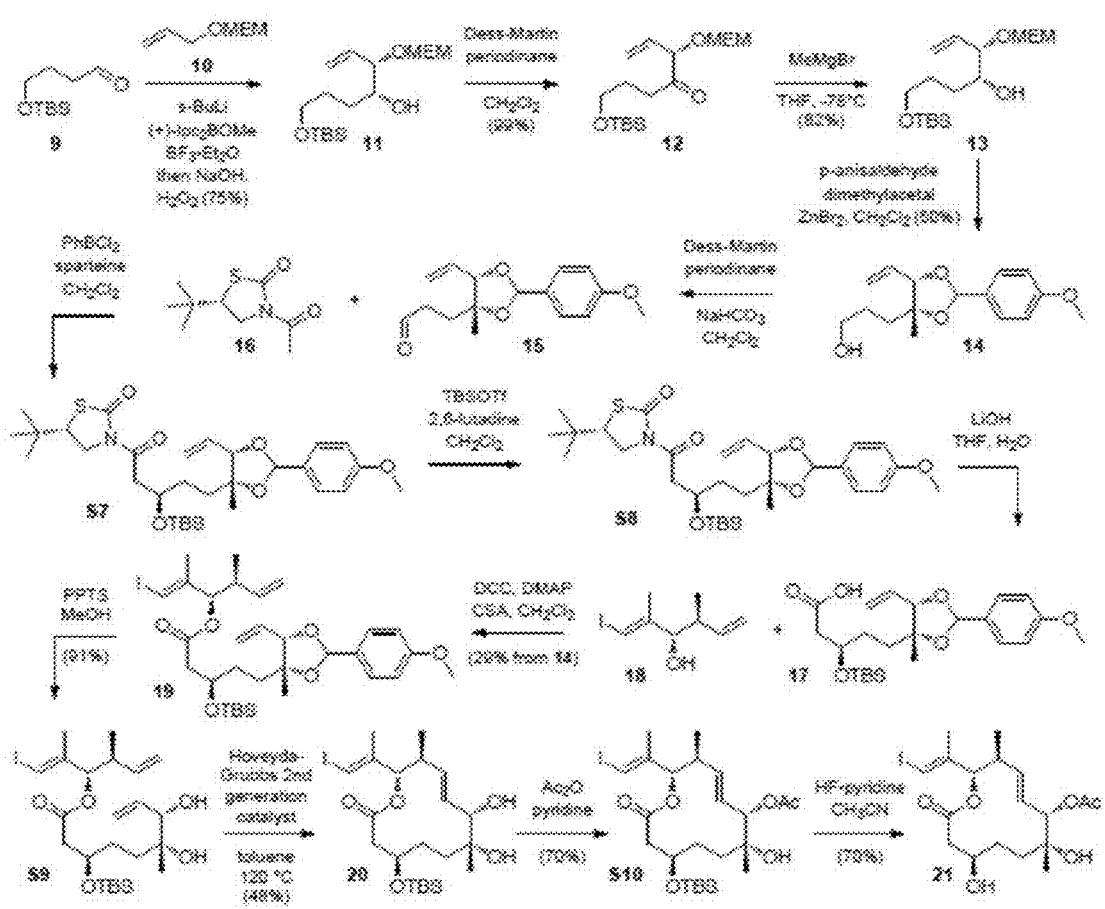
FIG. 7: Synthetic scheme of core portion of synthetic derivatives of FD-895.
Figure 8:
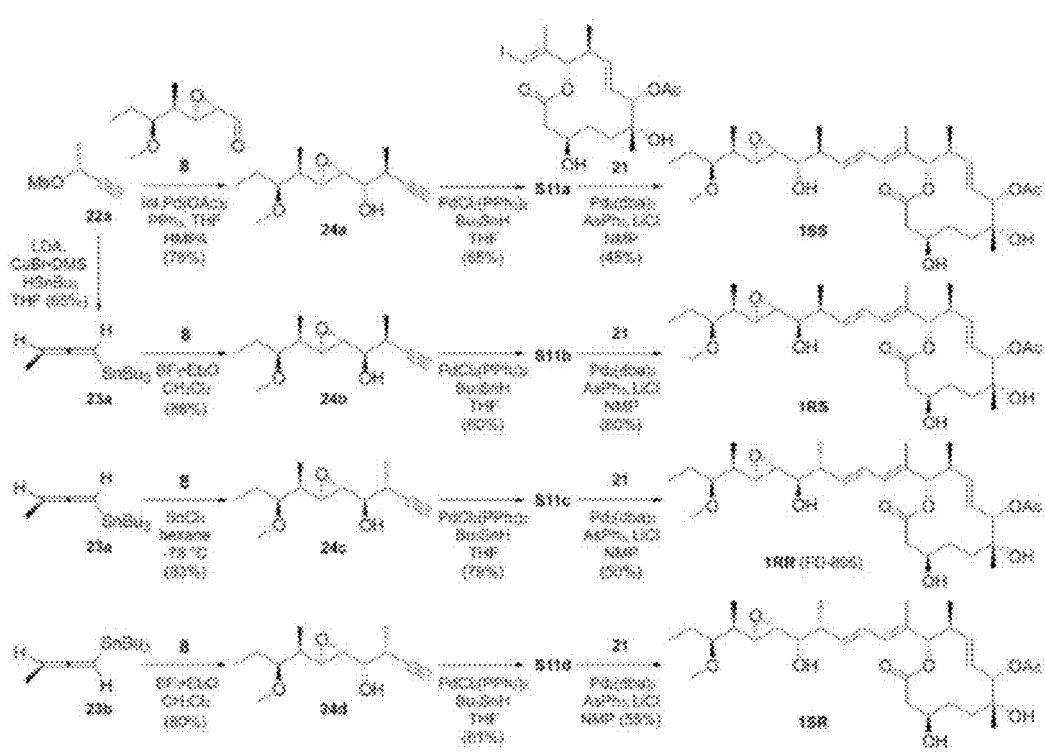
FIG. 8: Synthetic scheme of epoxide derivatives of FD-895.
Figure 9:
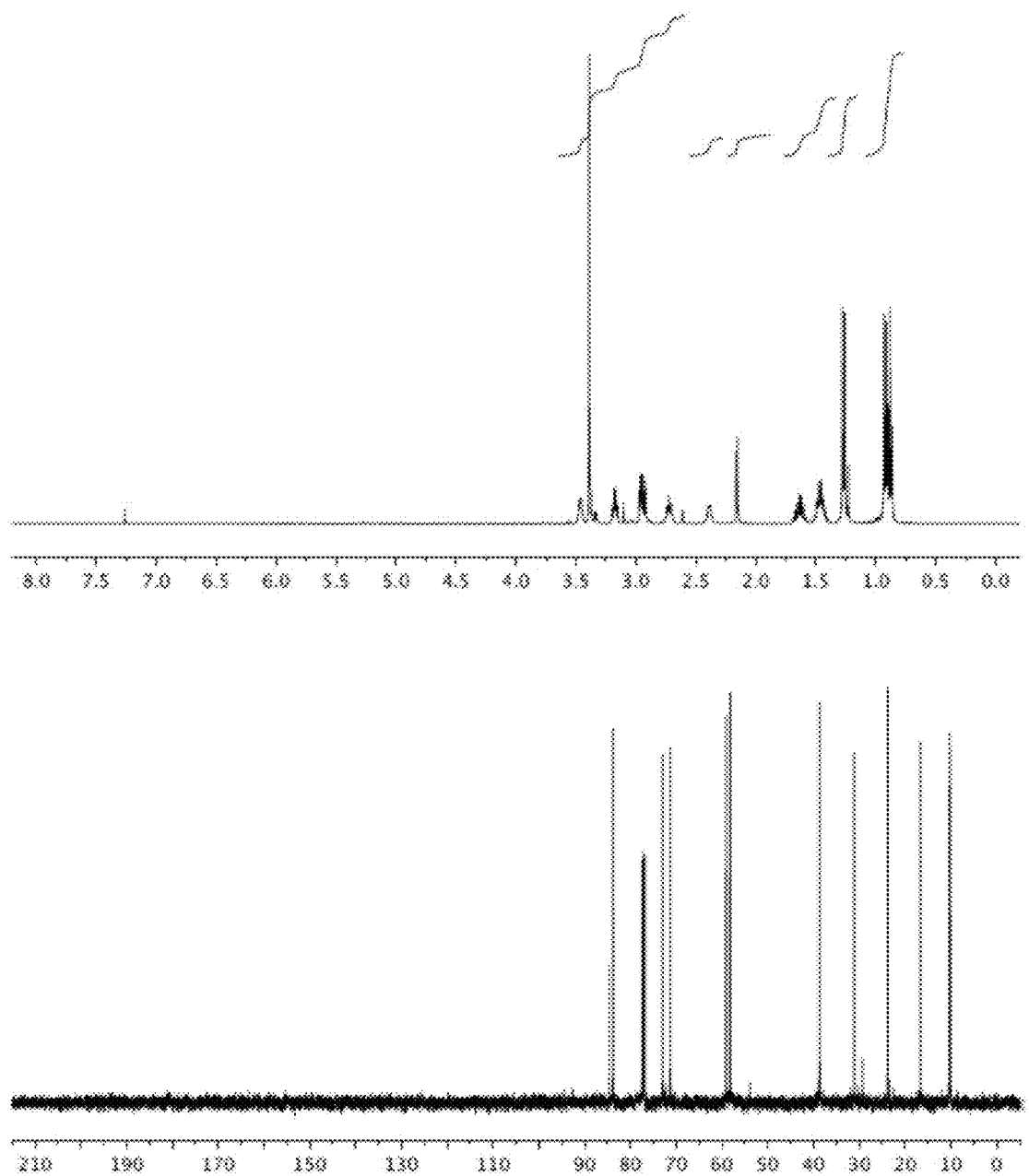
FIG. 9: $^1$H and $^{13}$C NMR spectra of compound (XVIIa).
Figure 10:
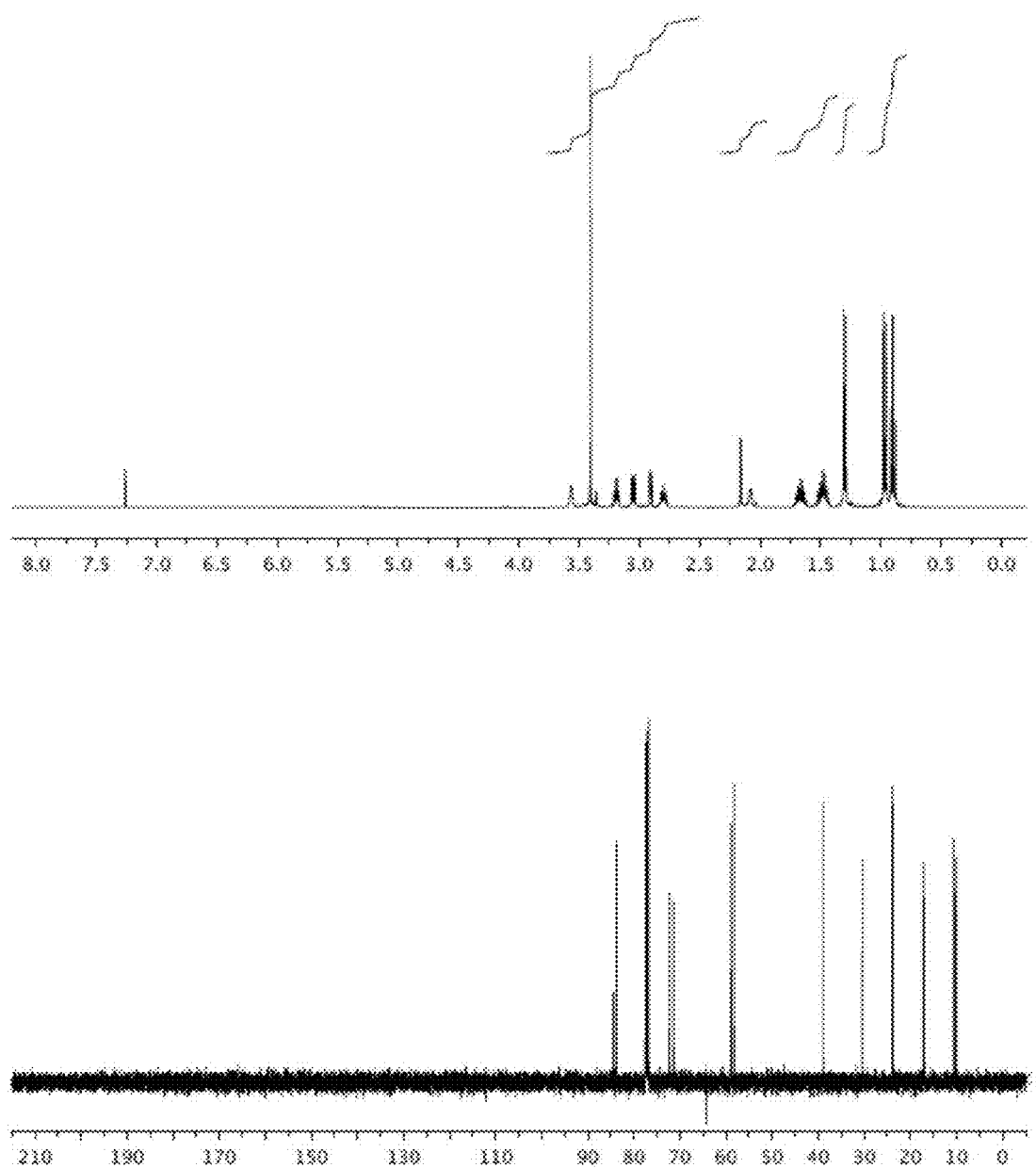
FIG. 10: $^1$H and $^{13}$C NMR spectra of compound (XVIIb).
Figure 11:
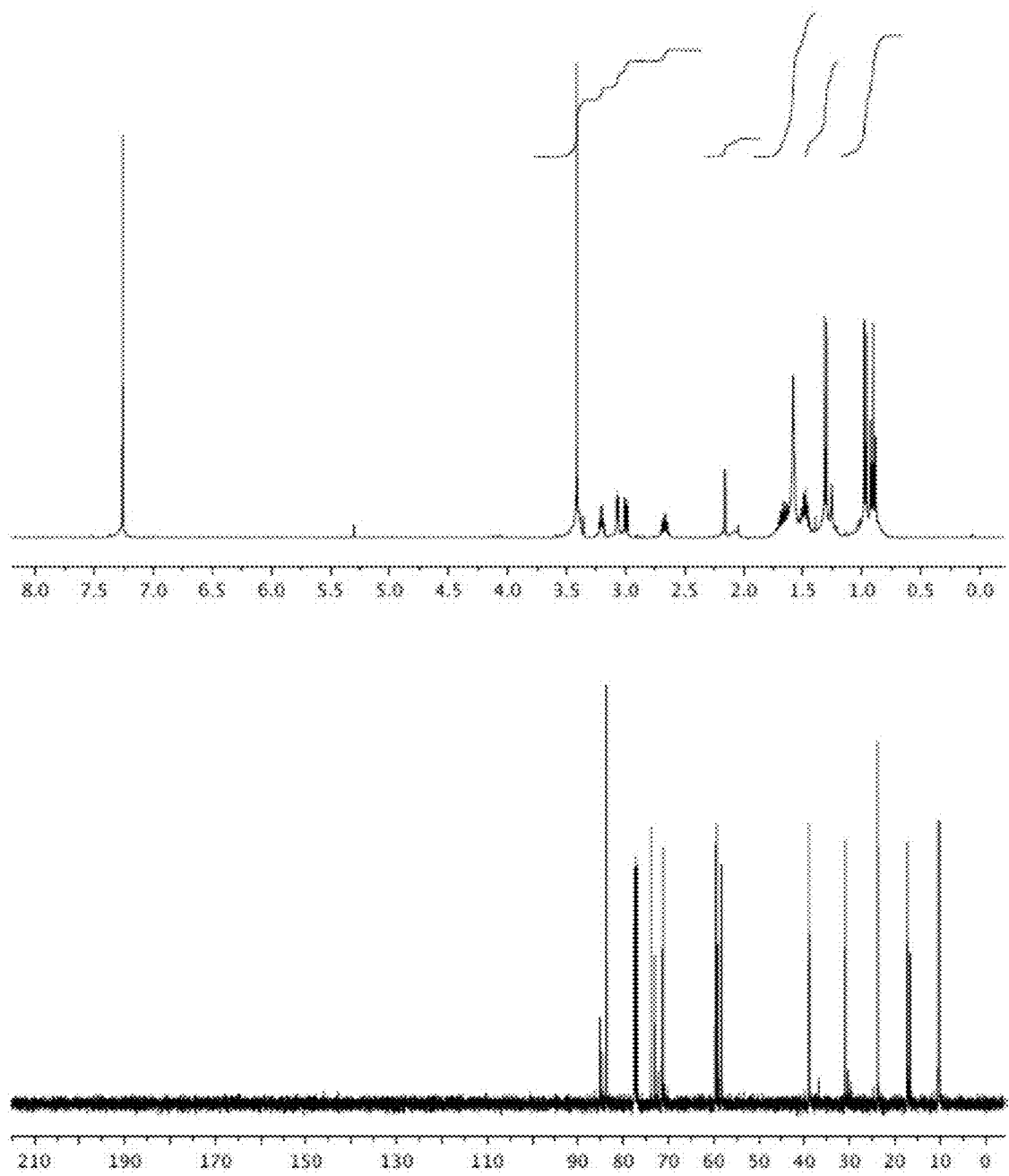
FIG. 11: $^1$H and $^{13}$C NMR spectra of compound (XVIIc).
Figure 12:
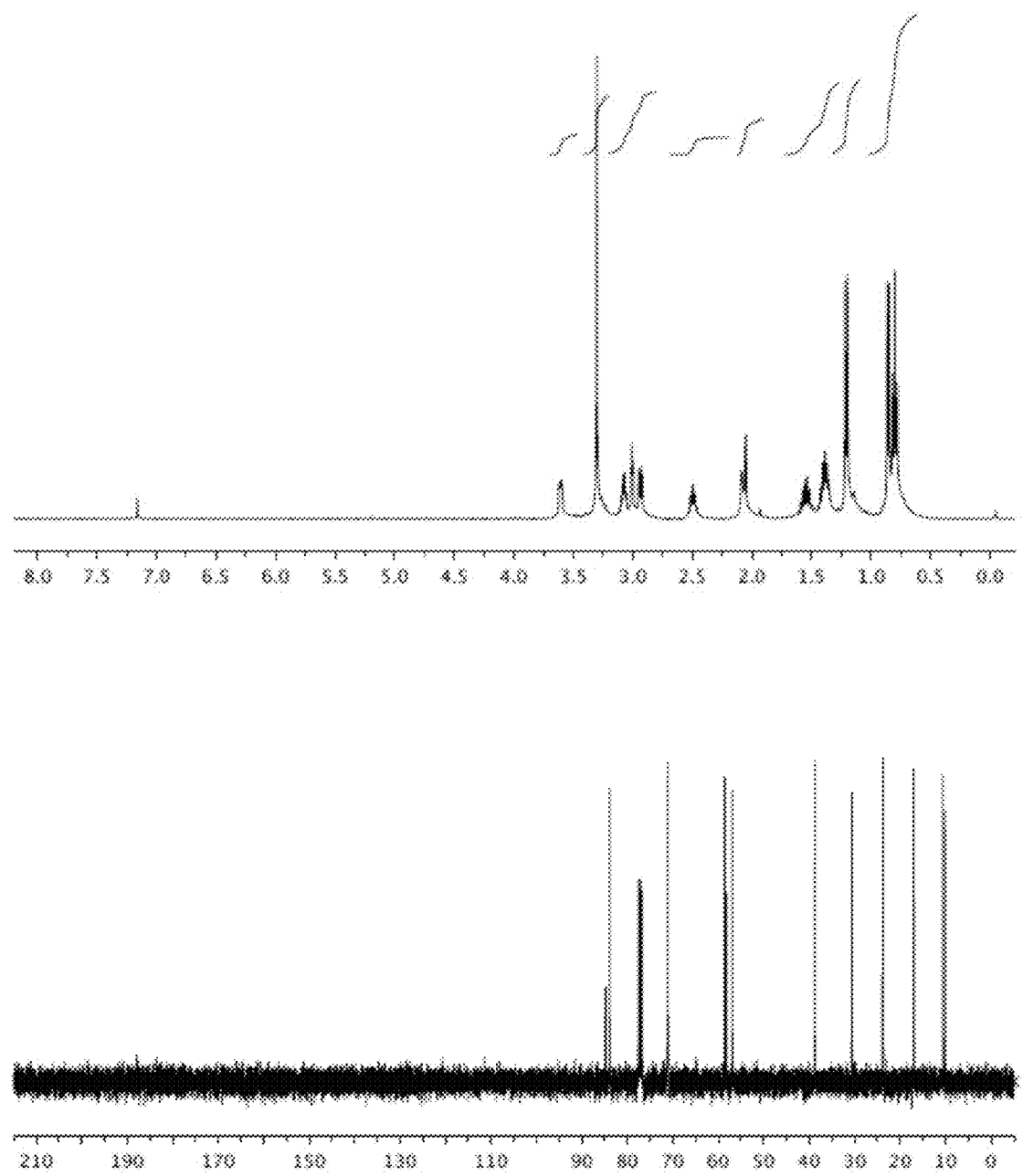
FIG. 12: $^1$H and $^{13}$C NMR spectra of compound (XVIId).
Figure 13:
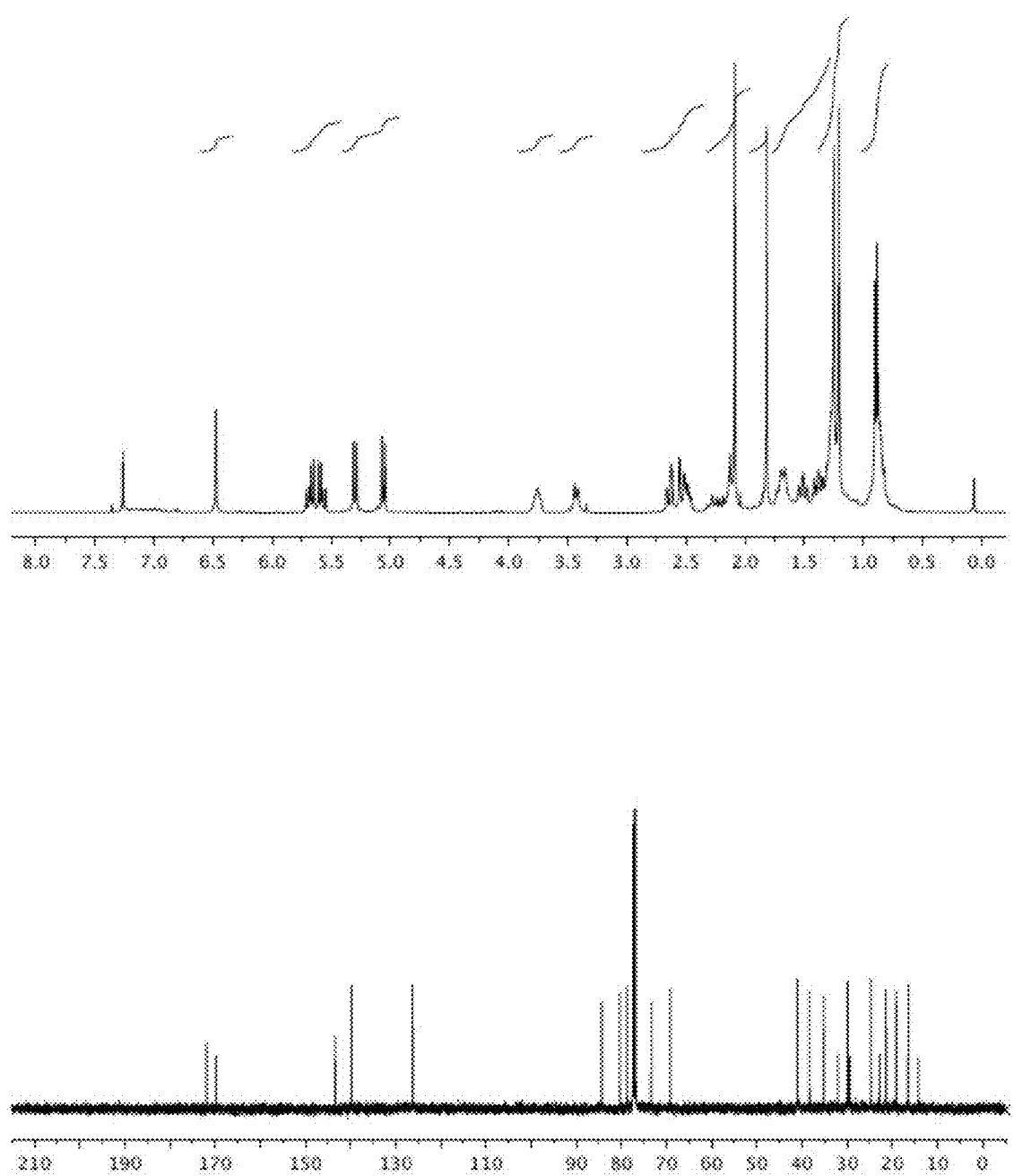
FIG. 13: $^1$H and $^{13}$C NMR spectra of compound (XVI).
Figure 14:
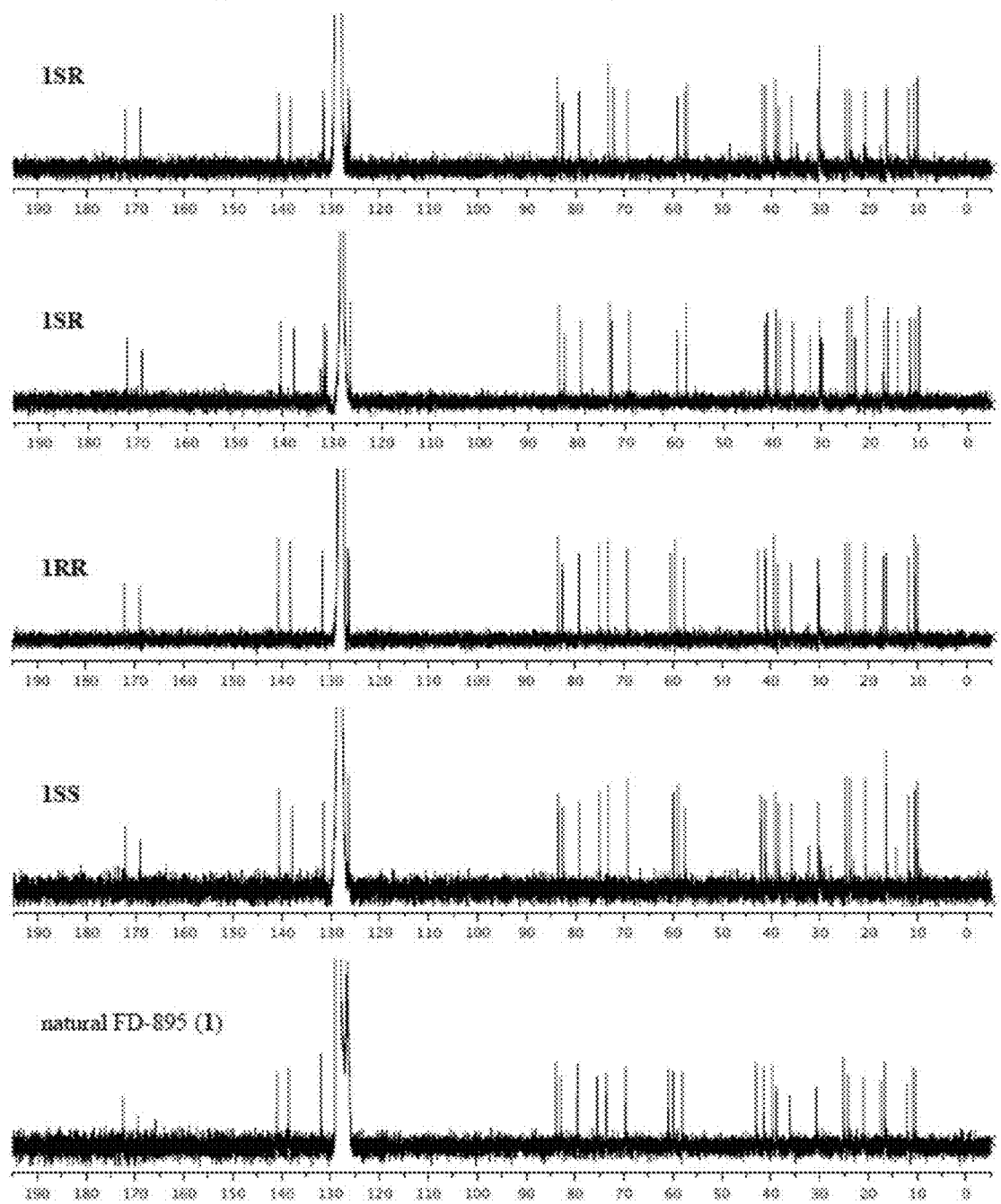
FIG. 14: $^{13}$C NMR spectra of synthetic isomers 1SR, 1RS, 1RR, 1SS and the $^{13}$C NMR spectra of the natural FD-895 (1) compound.
Figure 15:
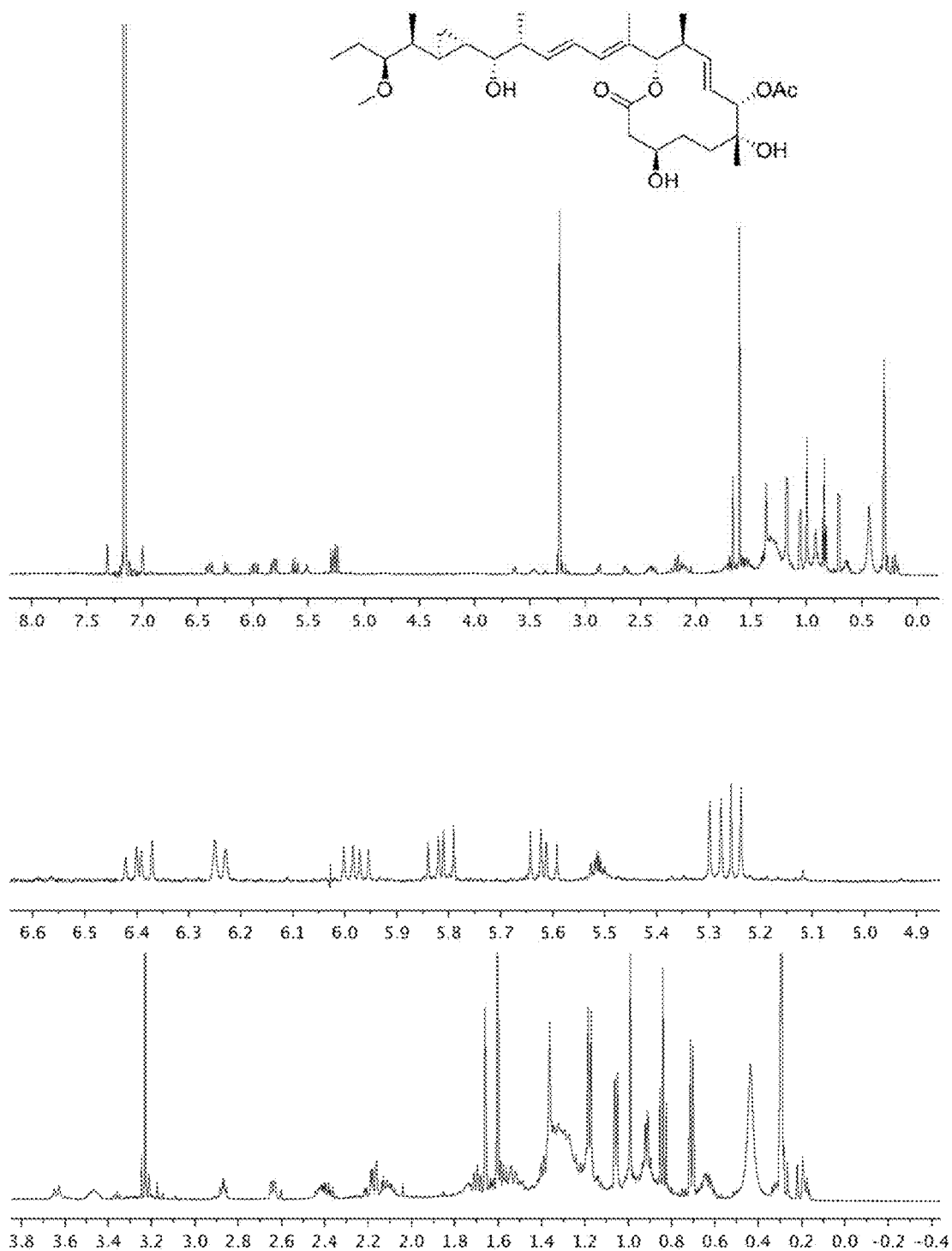
FIG. 15: 1H NMR for the SR cyclopropane derivative.
Figure 16:
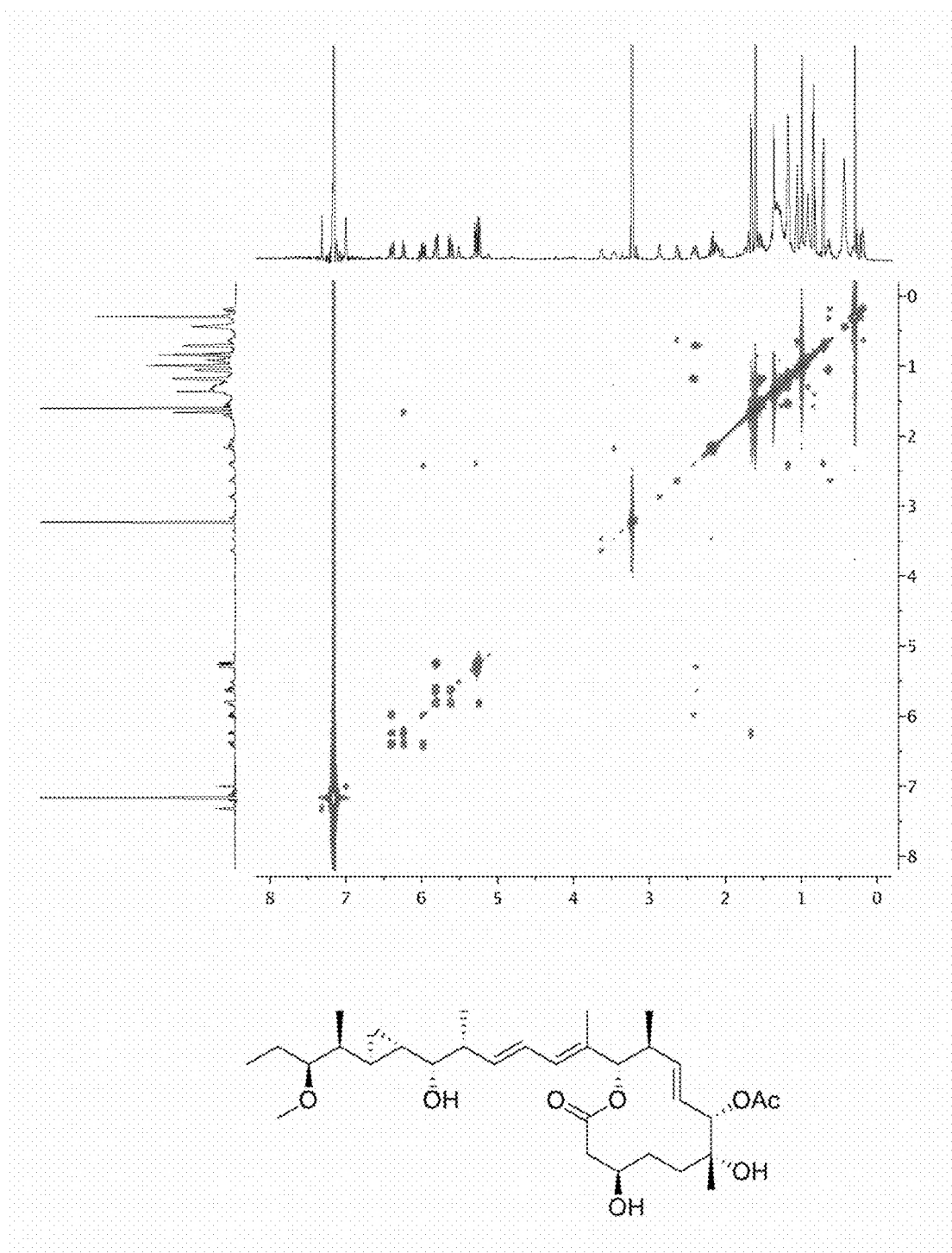
FIG. 16: NMR for the SR cyclopropane derivative.
Figure 17:
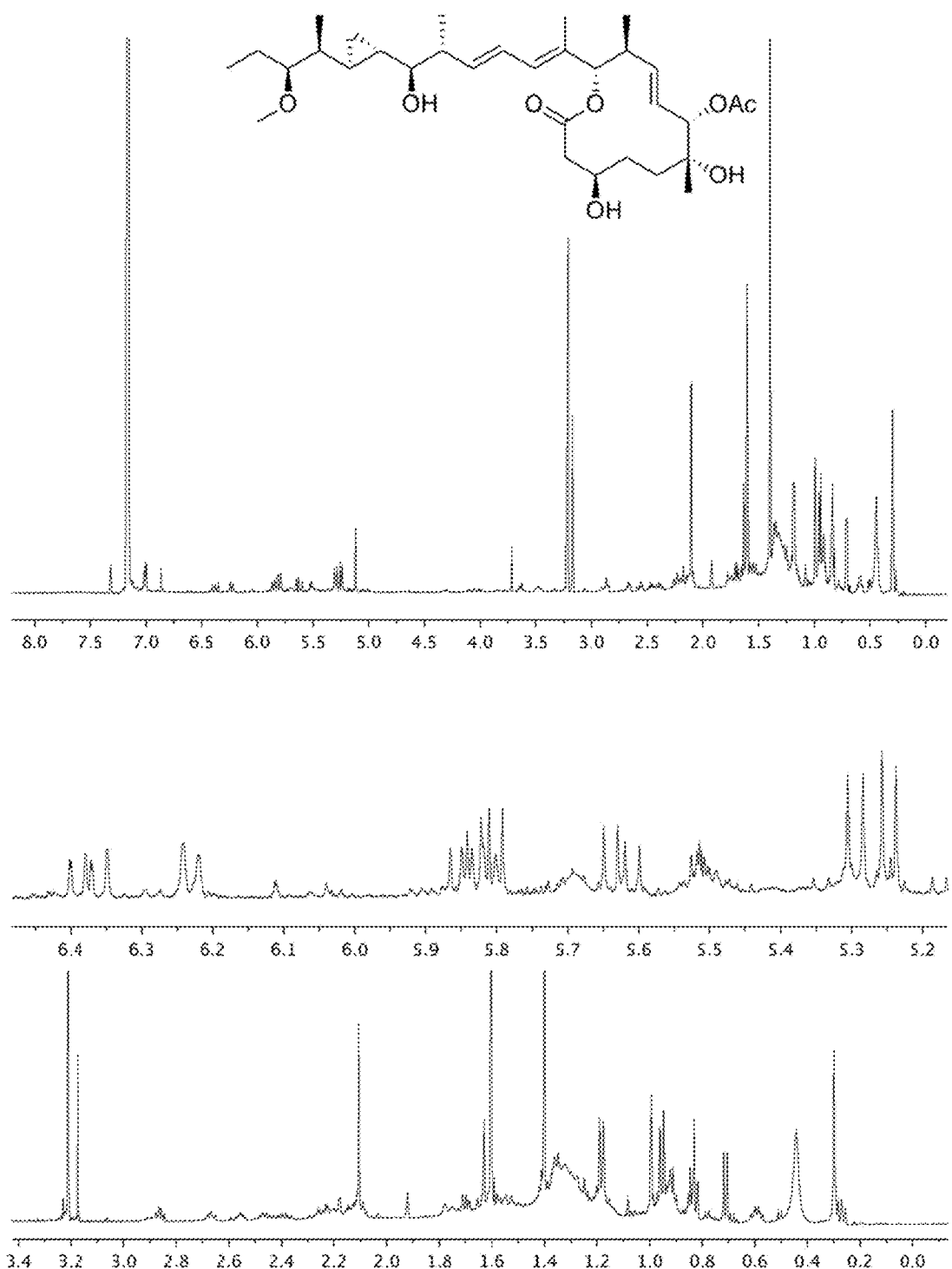
FIG. 17: 1H NMR for the RR cyclopropane derivative.

At 4 hours of treatment, FD-895 and PLAD at 10 nM caused a clear increase in unspliced mRNA of DNAJB1 and RIOK3 in CLL while in normal B cells both compounds did not show significant increase in unspliced mRNA of DNAJB1 and RIOK3 (FIG. 7A, B).

REFERENCES

Gottleib, H. E.; Kotlyar, V. Nudelman, A. *J. Org. Chem.* 1997, 62, 7512-7515.

McKennon, M. J.; Meyers, A. I.; Drauz, K.; Schwarm, M. *J. Org. Chem.* 1993, 58, 3568-3572.

Delaunay, D.; Toupet, L.; Le Corre, M. *J. Org. Chem.* 1995, 60, 6604-6607.

Mans, D. M.; Pearson, W. H. *J. Org. Chem.* 2004, 68, 6419-6426.

Light, J.; Breslow, R. *Tetrahedron Letters* 1990, 31, 2957-2958

Mandel, A. L.; Jones, B. D.; La Clair, J. J.; Burkart, M. D. *Bioorg. Med. Chem. Lett.* 2007 17, 5159-5164.

Marshall, J. A.; Grant, C. M. *J. Org. Chem.* 1999, 64, 8214-8219.

Marshall, J. A.; Yanik M. M. *Org. Lett.* 2000, 2, 2173-2176.

Matutes, E. et al. The immunological profile of B-cell disorders and proposal of a scoring system for the diagnosis of CLL. *Leukemia* 8, 1640-1645 (1994).

Kato, K., Cantwell, M. J., Sharma, S. & Kipps, T. J. Gene transfer of CD40-ligand induces autologous immune recognition of chronic lymphocytic leukemia B cells. *The Journal of clinical investigation* 101, 1133-1141, doi:10.1172/JCI1472 (1998).

Chu, P. et al. Latent sensitivity to Fas-mediated apoptosis after CD40 ligation may explain activity of CD154 gene therapy in chronic lymphocytic leukemia. *Proceedings of the National Academy of Sciences of the United States of America* 99, 3854-3859, doi:10.1073/pnas. 022604399 (2002).

Livak, K. J. & Schmittgen, T. D. Analysis of relative gene expression data using real-time quantitative PCR and the 2(-Delta Delta C(T)) Method. *Methods* 25, 402-408, doi:10.1006/meth. 2001.1262 (2001).

Seki-Asano, M.; Okazaki, T.; Yamagishi, M.; Sakai, N.; Takayama, Y.; Hanada, K.; Morimoto, S.; Takatsuki, A.; Mizoue K. *J. Antibiot (Tokyo).* 1994, 47, 1395-1401.

Mizui, Y.; Sakai, T.; Iwata, M.; Uenaka, T.; Okamoto, K.; Shimizu, H.; Yamori, T.; Yoshimatsu, K.; Asada M. *J. Antibiot (Tokyo).* 2004, 57, 188-196.

Asai, N.; Kotake, Y.; Niijima, J.; Fukuda, Y.; Uehara, T.; Sakai, T. *J. Antibiot (Tokyo).* 2007, 57, 188-196.

Kanada, R. M.; Itoh, D.; Nagai, M.; Niijima, J.; Asai, N.; Mizui, Y.; Abe, S.; Kotake, Y. *Angew. Chem. Int. Ed. Engl.* 2007, 46, 4350-4355.

Kotake, Y.; Sagane, K.; Owa, T.; Mimori-Kiyosue, Y.; Shimizu, H.; Uesugi, M.; Ishihama, Y.; Iwata, M.; Mizui, Y. *Nat. Chem. Biol.* 2007, 3, 570-575.

Kaida, D.; Motoyoshi, H.; Tashiro, E.; Nojima, T.; Hagiwara, M.; Ishigami, K.; Watanabe, H.; Kitahara, T.; Yoshida, T.; Nakajima, H.; Tani, T.; Horinouchi, S.; Yoshida, M. *Nat. Chem. Biol.* 2007, 3, 576-583.

Hasegawa, M.; Miura, T.; Kuzuya, K.; Inoue, A.; Won Ki, S.; Horinouchi, S.; Yoshida, T.; Kunoh, T.; Koseki, K.; Mino, K.; Sasaki, R.; Yoshida, M.; Mizukami T. *ACS Chem. Biol.* 2011, 6, 229-233.

Yokoi, A.; Kotake, Y.; Takahashi, K.; Kadowaki, T.; Matsumoto, Y.; Minoshima, Y.; Sugi, N. H.; Sagane, K.; Hamaguchi, M.; Iwata, M.; Mizui Y. *FEBS J.* 2011, 278, 4870-4880.

Folco, E. G.; Coil, K. E.; Reed, R. Genes Dev. 2011, 25, 440-444.

Ward, A. J.; Cooper T. A. *J. Pathol.* 2010, 220, 152-163.

Fan, L.; Lagisetti, C.; Edwards, C. C.; Webb, T. R.; Potter, P. M. *ACS Chem. Biol.* 2011, 6, 582-589.

Stille, J. K.; Groh, B. L. *J. Am. Chem. Soc.* 1987, 109, 813-817.

Marshall, J. A. *J. Org. Chem.* 2007, 72, 8153-8166.

Marshall, J. A.; Perkins, J. *J. Org. Chem.* 1994, 59, 3509-3511.

Crimmins, M. T.; King, B. W.; Tabet, E. A. *J. Am. Chem. Soc.* 1997, 119, 7883-7884.

Wadsworth, W. S.; Emmons, W. D. *J. Am. Chem. Soc.* 1961, 83, 1733-1738.

Katsuki, T.; Sharpless, K. B. *J. Am. Chem. Soc.* 1980, 102, 5974-5976.

More, J. D.; Finney, N. S. *Org. Lett.* 2002, 4, 3001-3003.

Müller, S.; Mayer, T.; Sasse, F.; Maier, M. E. *Org. Lett.* 2011, 13, 3940-3943.

Skaanderup, P. R.; Jensen, T. *Org. Lett.* 2008, 10, 2821-2124.

Ramachandran, P. V.; Liu, H.; Ram Reddy, M. V.; Brown, H. C. *Org. Lett.* 2003, 5, 3755-3757.

Still, W. C.; McDonald, J. H., *Tetrahedron Lett.* 1980, 21, 1031-1034.

Zhang, Y.; Phillips, A. J.; Sammakia, T. *Org. Lett.* 2003, 6, 23-25.

Ko, K. S.; Alexander, M. D.; Fontaine, S. D.; Biggs-Houck, J. E.; La Clair, J. J.; Burkart, M. D. *Org. Biomol. Chem.* 2010, 8, 5159-5165.

Stewart, I. C.; Ung, T.; Pletnev, A. A.; Berlin, J. M.; Grubbs, R. H.; Schrodi, Y. *Org. Lett.* 2007, 9, 1589-1592.

Ichinose, Y.; Oda, H.; Oshima, K.; Utimoto, K. *Bull. Chem. Soc. Jpn.* 1987, 60, 3468.

Mosmann, T. *J. Immunol. Meth.* 1983, 65, 55-83.

Ko, K. S.; Alexander, M. D.; Fontaine, S. D.; Biggs-Houck, J. E.; La Clair, J. J.; Burkart, M. D. Synthetic studies on the mycolactone core. *Org. Biomol. Chem.* 2010, 8, 5159-5165.

Villa, R., Mandel, A. L., Jones, B. D., La Clair, J. J. & Burkart M. D. Structure of FD-895 unveiled through total synthesis. *Org. Lett.* 2012, 14.

Butler, M. S. Natural products to drugs: natural product-derived compounds in clinical trials. *Nat. Prod. Rep.* 2008, 25, 475-516.

Gundluru, M. K.; Pourpak, A.; Cui, X.; Morris, S. W.; Webb, T. R. Design, synthesis and initial biological evaluation of a novel pladienolide analog scaffold. *Medchemcomm.* 2011, 2, 904-908.

Komatsu, M.; Uchiyama, T.; Omura, S.; Cane, D. E.; Ikeda, H. Genome-minimized

Streptomyces host for the heterologous expression of secondary metabolism. *Proc. Natl. Acad. Sci. U.S.A.* 2010, 107, 2646-51.

Machida, K.; Aritoku, Y.; Tsuchida T. One-pot fermentation of pladienolide D by Streptomyces platensis expressing a heterologous cytochrome P450 gene. *J. Biosci. Bioeng.* 2009, 106, 596-598.

Machida, K.; Arisawa, A.; Takeda, S., Tsuchida, T.; Aritoku, Y.; Yoshida, M.; Ikeda H. Organization of the biosynthetic gene cluster for the polyketide antitumor macrolide, pladienolide, in Streptomyces platensis Mer-11107. *Biosci. Biotechnol. Biochem.* 2008, 72, 2946-2952.

Lagisetti C, Pourpak A, Jiang Q, Cui X, Goronga T, Morris S W, Webb T R. Antitumor compounds based on a natural product consensus pharmacophore. *J. Med. Chem.* 2008, 51, 6220-6224.

Sumantran, V. N. Cellular chemosensitivity assays: an overview. *Methods Mol Biol.* 2011, 731, 219-236.

Mosmann, T. Rapid colorimetric assay for cellular growth and survival: application to proliferation and cytotoxicity assays. *J. Immunol. Meth.* 1983, 65, 55-63.

Embodiments

Embodiment 1

A compound having the formula:

[Chemical structure showing a macrocyclic compound with substituents X², R³, R², R¹⁵, R⁵, R⁴, X¹, OR¹, OH, OH]

wherein, $X^1$ is N, O, or $CH_2$;
$X^2$ is O or $C(R^6)(R^7)$;
$R^6$ and $R^7$ are independently hydrogen, halogen, substituted or unsubstituted alkyl, substituted or unsubstituted aryl, $-OR^{12}$, $-OC(O)R^{12}$, $-OC(O)OR^{12}$, or $-OC(O)NR^{13}R^{14}$;
$R^1$ is hydrogen, $-C(O)R^8$, $-OC(O)R^8$, $-OC(O)OR^8$, or $-NHC(O)NHR^8$;
$R^2$, $R^3$, $R^4$, and $R^5$ are each independently selected from hydrogen, substituted or unsubstituted alkyl, $-OR^9$, $-OC(O)R^9$, $-OC(O)OR^9$, or $-OC(O)NR^{10}R^{11}$, $R^8$, $R^9$, $R^{10}$, $R^{11}$, $R^{12}$, $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
$R^{15}$ is hydrogen, halogen, $CF_3$, $CCl_3$, $CBr_3$, $CI_3$, or substituted or unsubstituted alkyl.

Embodiment 2

The compound of embodiment 1, wherein $X^1$ is O.

Embodiment 3

The compound of embodiments 1-2, wherein $R^2$ is methyl.

Embodiment 4

The compound of embodiments 1-3, wherein $R^4$ is $-OR^9$, wherein $R^9$ is hydrogen or $C_1$-$C_4$ unsubstituted alkyl.

Embodiment 5

The compound of embodiments 1-4, wherein $R^2$ is attached to a chiral carbon having (S) stereochemistry, and $R^4$ is attached to a carbon having (S) or (R) stereochemistry.

Embodiment 6

The compound of embodiments 1-5, wherein $R^2$ is attached to a chiral carbon having (S) stereochemistry, and $R^4$ is attached to a carbon having (S) stereochemistry.

Embodiment 7

The compound of embodiments 1-6, wherein $R^2$ is attached to a carbon having (S) stereochemistry, and $R^4$ is attached to a carbon having (R) stereochemistry.

Embodiment 8

The compound of embodiments 1-4, wherein $R^2$ is attached to a chiral carbon having (R) stereochemistry, and $R^4$ is attached to a carbon having (S) stereochemistry.

Embodiment 9

A compound having the formula:

(II)

[Chemical structure II with OR⁹, R¹⁵, OR¹, OH, OH substituents]

(III)

[Chemical structure III with OR⁹, R¹⁵, OR¹, OH, OH substituents]

(IV)

[Chemical structure IV with OR⁹, R¹⁵, OR¹, OH, OH substituents]

(V)

[Chemical structure V with R⁷, R⁶, OR⁹, R¹⁵, OR¹, OH, OH substituents]

-continued

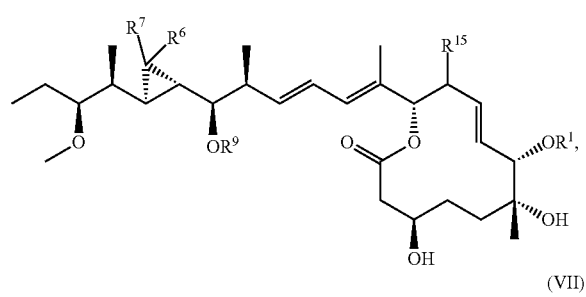
(VI)

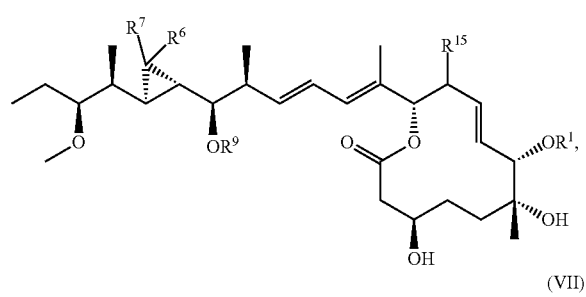
(VII)

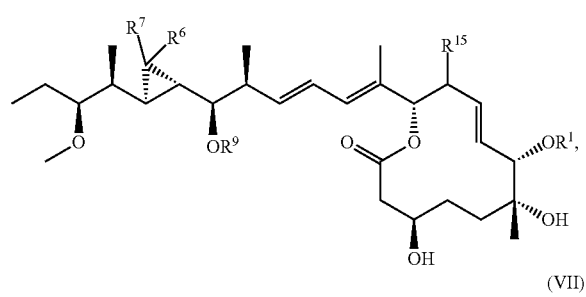
(VIII)

$R^1$, $R^6$, $R^7$, and $R^{15}$ are as defined herein.

Embodiment 10

The compound of embodiments 1-9, wherein $R^1$ is acetyl or hydrogen.

Embodiment 11

The compound of embodiments 1-10, wherein $R^1$ is acetyl

Embodiment 12

The compound of embodiments 1-11, wherein $R^{15}$ is hydrogen or $C_1$-$C_4$ unsubstituted alkyl.

Embodiment 13

The compound of embodiments 1-12, wherein $R^{15}$ is $C_1$-$C_4$ unsubstituted alkyl.

Embodiment 14

The compound of embodiments 1-13, wherein $R^{15}$ is $C_1$-$C_4$ unsubstituted alkyne or $C_1$-$C_4$ alkene.

Embodiment 15

The compound of embodiments 1-14, wherein $R^{15}$ is methyl.

Embodiment 16

The compound of embodiments 1-15, wherein $R^{15}$ is hydrogen.

Embodiment 17

The compound of embodiment 1, wherein $X^2$ is $C(R^6)(R^7)$.

Embodiment 18

The compound of embodiments 1 or 17, wherein $R^6$ and $R^7$ are independently be hydrogen, halogen, or methyl.

Embodiment 19

The compound of embodiments 1 or 17-18, wherein $R^6$ and $R^7$ are hydrogen

Embodiment 20

The compound of embodiments 1 or 17-19, wherein $R^6$ and $R^7$ are fluoride.

Embodiment 21

The compound of embodiments 1 or 17-20, wherein $R^2$ is attached to a chiral carbon having (S) stereochemistry, and $R^4$ is attached to a carbon having (S) or (R) stereochemistry.

Embodiment 22

The compound of embodiments 1 or 17-21, wherein $R^2$ and $R^4$ are attached to a chiral carbon having (S) stereochemistry.

Embodiment 23

The compound of embodiments 1 or 17-22, wherein $R^2$ is attached to a carbon having (S) stereochemistry, and $R^4$ is attached to a carbon having (R) stereochemistry.

Embodiment 24

The compound of embodiments 1 or 17-20, wherein $R^2$ is attached to a chiral carbon having (R) stereochemistry, and $R^4$ is attached to a carbon having (S) or (R) stereochemistry.

Embodiment 25

The compound of embodiments 1 or 17-20, 24, wherein $R^2$ and $R^4$ are attached to a chiral carbon having (R) stereochemistry.

Embodiment 26

The compound of embodiments 1 or 17-20, or 24-25, wherein $R^2$ is attached to a carbon having (R) stereochemistry, and $R^4$ is attached to a carbon having (S) stereochemistry.

Embodiment 27
The compound of embodiments 1-16, having formula:
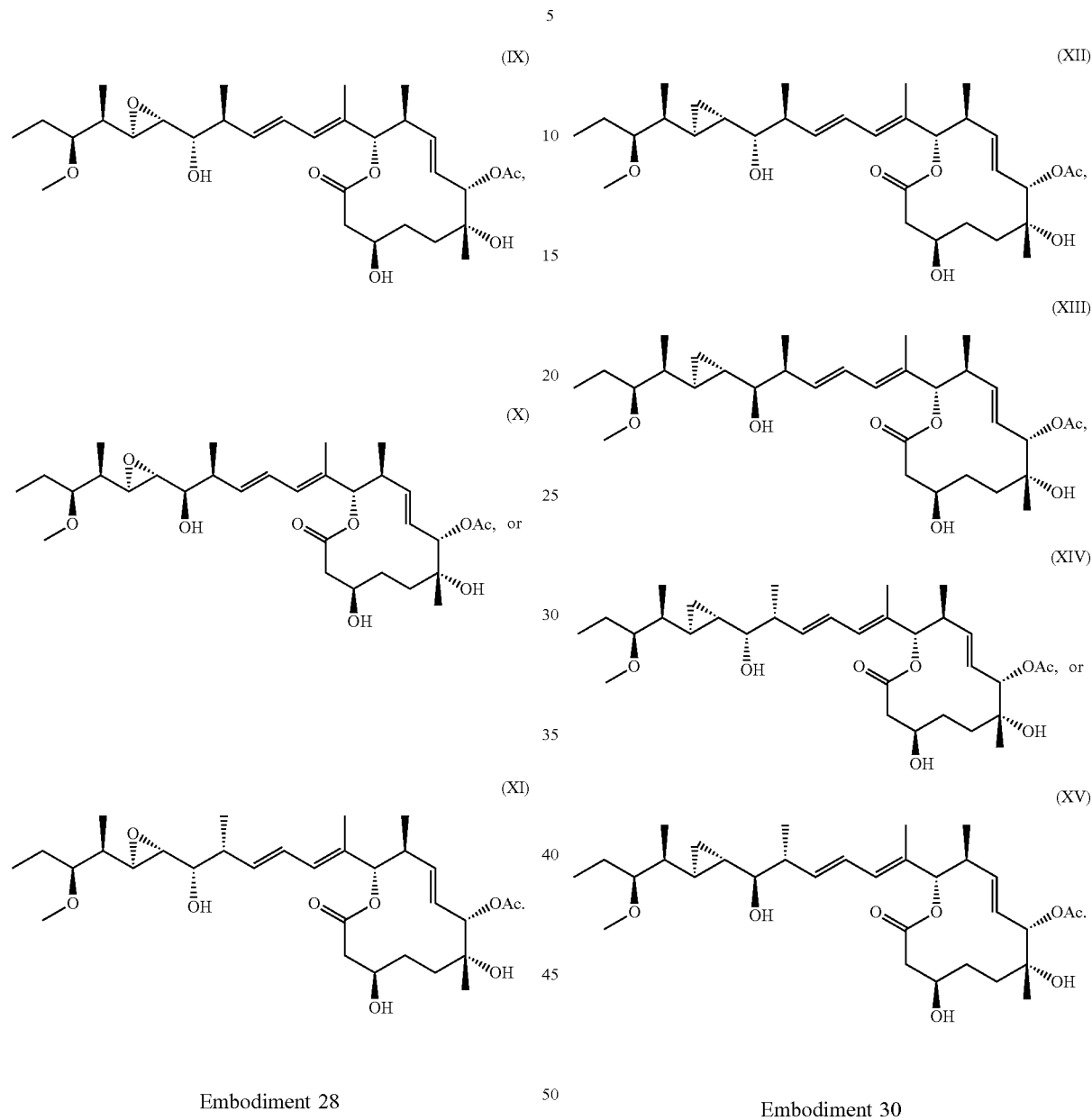
Embodiment 28
The compound of embodiment 27 having formula:
Embodiment 29
The compound of embodiments 1, 17-26 having formula:
Embodiment 30
The compound of embodiments 29 having formula:
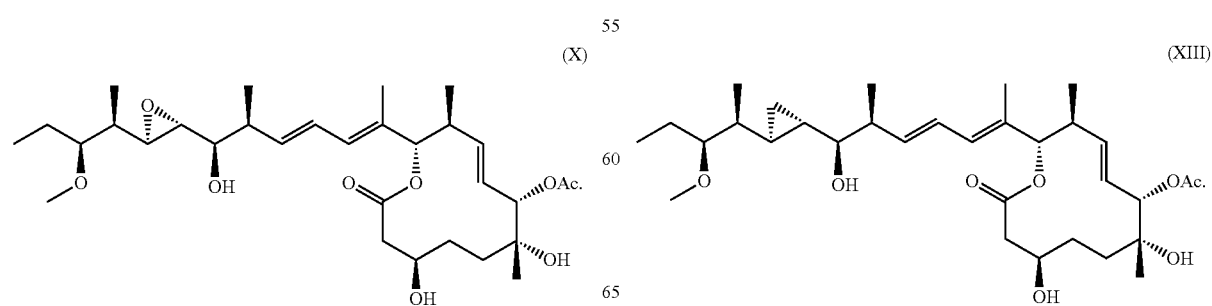

Embodiment 31

A compound having formula:

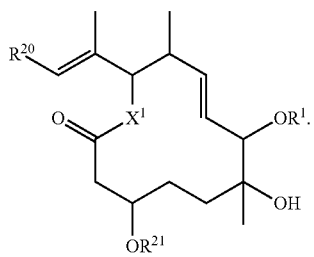

(XVI)

wherein,

X¹ and R¹ are as defined herein;

R²⁰ is halogen, $SO_3CF_3$, or $SO_3(C_6H_6)CH_3$; and

R²¹ is hydrogen, $C(O)R^8$, $OCO(O)R^8$, $OC(O)OR^8$, $NHC(O)NHR^8$.

Embodiment 32

The compound of embodiment 31 having formula:

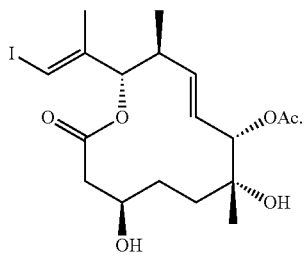

(XVIa)

Embodiment 33

A compound having formula:

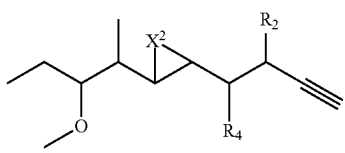

(XVII)

wherein,

X², R², and R⁴ are as defined herein.

Embodiment 34

The compound of embodiment 33, wherein X² is O.

Embodiment 35

The compound of embodiment 33-34, wherein R² is attached to a chiral carbon having (S) stereochemistry, and R⁴ is attached to a carbon having (S) or (R) stereochemistry.

Embodiment 36

The compound of embodiment 33-35, wherein R² is attached to a carbon having (S) stereochemistry, and R⁴ is attached to a carbon having (S) stereochemistry.

Embodiment 37

The compound of embodiment 33-36, wherein R² is attached to a carbon having (S) stereochemistry, and R⁴ is attached to a carbon having (R) stereochemistry

Embodiment 38

The compound of embodiment 33-34, wherein R² is attached to a chiral carbon having (R) stereochemistry, and R⁴ is attached to a carbon having (S) stereochemistry.

Embodiment 39

The compound of embodiment 33-38 having formula:

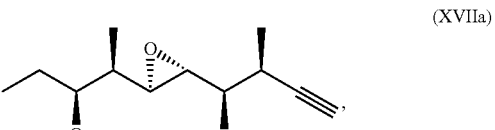

(XVIIa)

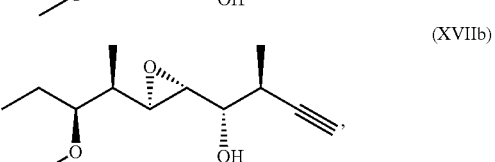

(XVIIb)

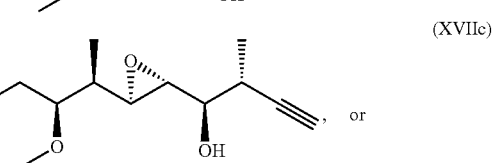

(XVIIc)

or

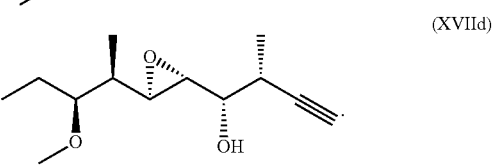

(XVIId)

Embodiment 40

The compound of embodiment 33, wherein X² is $C(R^6)(R^7)$.

Embodiment 41

The compound of embodiment 33 or 40, wherein R⁶ and R⁷ are independently hydrogen, halogen, or methyl.

Embodiment 42

The compound of embodiment 33 or 40-41, wherein R⁶ and R⁷ are hydrogen.

Embodiment 43

The compound of embodiment 33 or 40-41, wherein $R^6$ and $R^7$ are fluoride.

Embodiment 44

The compound of embodiment 33 or 40-43, wherein $R^2$ is attached to a chiral carbon having (S) stereochemistry, and $R^4$ is attached to a carbon having (S) or (R) stereochemistry.

Embodiment 45

The compound of embodiment 33 or 40-44, wherein $R^2$ and $R^4$ are attached to a chiral carbon having (S) stereochemistry.

Embodiment 46

The compound of embodiment 33 or 40-45, wherein $R^2$ is attached to a carbon having (S) stereochemistry, and $R^4$ is attached to a carbon having (R) stereochemistry.

Embodiment 47

The compound of embodiment 33 or 40-43, wherein $R^2$ is attached to a chiral carbon having (R) stereochemistry, and $R^4$ is attached to a carbon having (S) or (R) stereochemistry.

Embodiment 48

The compound of embodiment 33 or 40-43 or 47, wherein $R^2$ and $R^4$ are attached to a chiral carbon having (R) stereochemistry.

Embodiment 49

The compound of embodiment 33 or 40-43, or 47-48, wherein $R^2$ is attached to a carbon having (R) stereochemistry and $R^4$ is attached to a carbon having (S) stereochemistry

Embodiment 50

The compound of embodiment 3-49 having formula:

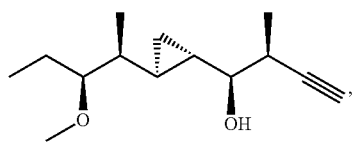

(XVIIe)

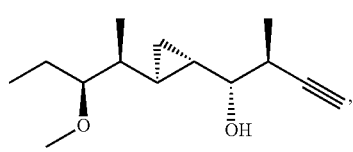

(XVIIf)

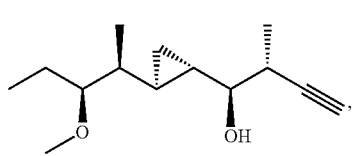

(XVIIg)

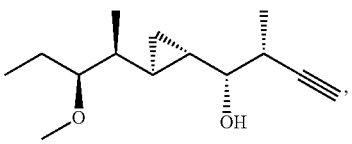

(XVIIh)

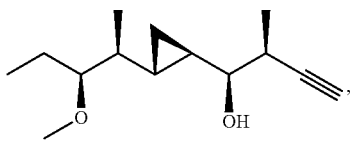

(XVIIi)

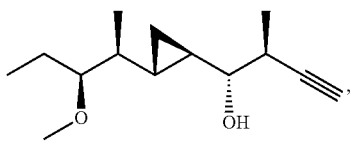

(XVIIj)

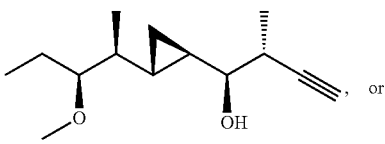

(XVIIk), or

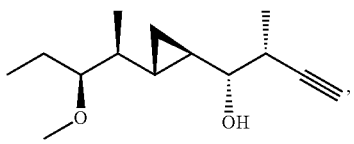

(XVIII)

Embodiment 51

A pharmaceutical composition comprising a compound having formula (I), (II), (III), (IV), (V), (VI), (VII), or (VIII), and a pharmaceutically acceptable excipient.

Embodiment 52

The pharmaceutical composition of embodiment 51, wherein the compound has formula (IX), (X), (XI), (XII), (XIII), (XIV), or (XV).

Embodiment 53

The pharmaceutical composition of embodiments 51-52, wherein the composition includes at least two of compounds having formula (I), (II), (III), (IV), (V), (VI), (VII), or (VIII).

Embodiment 54

The pharmaceutical composition of embodiments 51-53, wherein the composition is administered using a therapeutically effective amount.

Embodiment 55

The pharmaceutical composition of embodiments 51-54, wherein the composition includes one amount of a compound having formula (I), (II), (III), (IV), (V), (VI), (VII), or (VIII) and a second amount of a second compound having formula (I), (II), (III), (IV), (V), (VI), (VII), or (VIII).

Embodiment 56

The pharmaceutical composition of embodiments 51-55, wherein the composition includes at least one compound having formula (IX), (X), (XI), (XII), (XIII), (XIV), or (XV).

Embodiment 57

The pharmaceutical composition of embodiments 51-56, wherein the composition includes one amount of a compound having formula (IX), (X), (XI), (XII), (XIII), (XIV), or (XV) and a second amount of a second compound having formula (IX), (X), (XI), (XII), (XIII), (XIV), or (XV).

Embodiment 58

A method of treating cancer comprising administering to a subject in need thereof, a therapeutically effective amount of a compound having formula (I), (II), (III), (IV), (V), (VI), (VII), or (VIII).

Embodiment 59

The method of embodiment 58, wherein the compound may be co-administered with a pharmaceutically acceptable excipient.

Embodiment 60

The method of embodiments 58-59, wherein the cancer is leukemia, lymphoma, metastatic cancer or bone cancer.

Embodiment 61

The method of embodiments 58-60, wherein the cancer is leukemia or lymphoma.

Embodiment 62

The method of embodiments 58-61, wherein the cancer is chronic lymphocytic cancer (CLL).

Embodiment 63

A method of detecting spliceosome inhibition using a test compound comprising contacting a cell with the test compound, extracting an mRNA from the cell thereby producing an extracted mRNA, reverse transcribing the mRNA using intron-specific primers thereby forming an intron cDNA, amplifying the intron cDNA thereby forming a plurality of amplified intron cDNA's, and detecting the presence of the amplified intron cDNAs to detect spliceosome inhibition with the test compound.

Embodiment 64

The method of embodiment 63, wherein the extracting step includes lysing the cell.

Embodiment 65

The method of embodiments 63-64, wherein the intron-specific primers are primers for DNAJBG1, or RIOK3.

Embodiment 66

The method of embodiments 63-65, further including a control primer.

Embodiment 67

The method of embodiments 63-66, wherein the control primer is a complement of a sequence not affected by the spliceosome.

Embodiment 68

The method of embodiments 63-67, wherein the test compound is a compound having formula (I), (II), (III), (IV), (V), (VI), (VII), or (VIII).

Embodiment 69

The method of embodiments 63-68, wherein the test compound is a compound having formula (XI), (X), (XI), (XII), (XIII), (XIV), or (XV).

Embodiment 70

The method of embodiments 63-69, wherein the amplification further includes forming a plurality of amplified complementary intron cDNAs.

Embodiment 71

The method of embodiments 63-70, wherein the detection step detects the presence of the amplified complementary intron cDNAs.

Embodiment 72

The method of embodiments 63-71, wherein the detection step detects the presence of the amplified intron cDNAs and the amplified complementary intron cDNAs.

Embodiment 73

The method of embodiments 63-72, wherein the detection step detects the presence of the amplified intron cDNAs or the amplified complementary intron cDNAs.

Embodiment 74

The method of embodiments 63-73, wherein the detection step is performed following purification of the amplified intron cDNAs or purification of the amplified complementary cDNAs.

Embodiment 75

The method of embodiments 63-74, wherein the detection step is performed without purification prior to the detection.

Embodiment 76

The method of embodiments 63-75, wherein the detecting further includes determining an amount of the plurality of amplified intron cDNAs, based on the amount, determining a level of the mRNA within the sample, and comparing the level to a standard control level, wherein, an elevated level of the mRNA relative to the control level indicates the test compound interferes with splicing and targets the spliceosome.

Embodiment 77

The method of embodiments 63-76, wherein the detection of an amount of cDNAs may be performed using amplified complementary intron cDNAs.

Embodiment 78

The method of embodiments 63-77, wherein the detection of an amount of cDNAs may be performed using amplified intron cDNAs and amplified complementary intron cDNAs.

Embodiment 79

The method of embodiments 63-78, wherein the cell is derived from a cancer patient.

Embodiment 80

The method of embodiments 63-79, wherein the cell is obtained through biopsy.

Embodiment 81

The method of embodiments 63-80, wherein the cell is from a cancer patient having leukemia, lymphoma, metastatic cancer, or bone cancer.

Embodiment 82

The method of embodiments 63-81, wherein the cell is from a cancer patient having chronic lyphocytic leukemia (CLL).

Embodiment 83

The method of embodiments 63-82, wherein the cell is a cancer cell line.

Embodiment 84

The method of embodiments 63-83, wherein the cancer cell line is RAJI, Jurkat, or MEC1.

---

What is claimed is:

1. A compound having the formula:

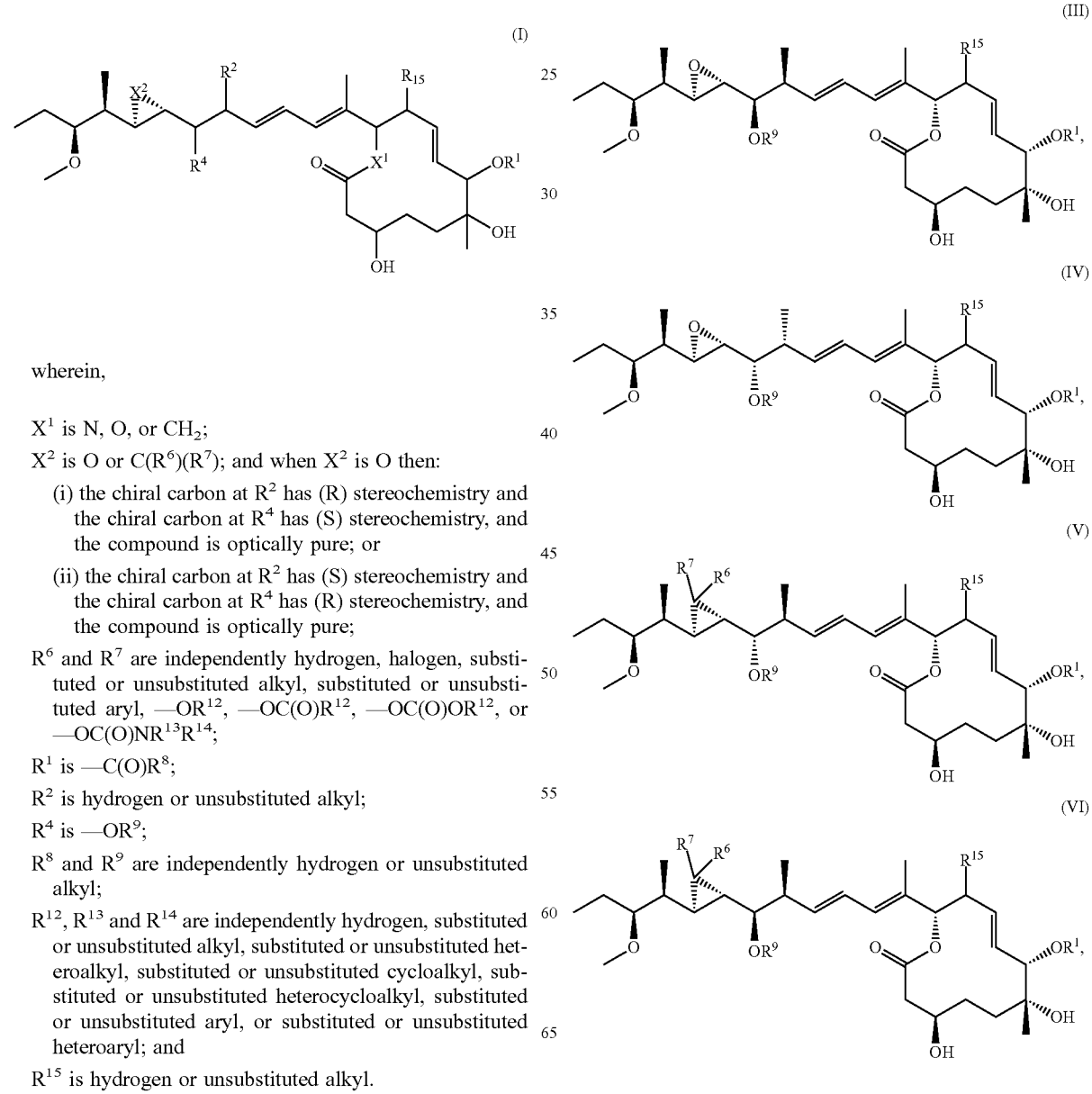

wherein, $X^1$ is N, O, or $CH_2$;

$X^2$ is O or $C(R^6)(R^7)$; and when $X^2$ is O then:

(i) the chiral carbon at $R^2$ has (R) stereochemistry and the chiral carbon at $R^4$ has (S) stereochemistry, and the compound is optically pure; or (ii) the chiral carbon at $R^2$ has (S) stereochemistry and the chiral carbon at $R^4$ has (R) stereochemistry, and the compound is optically pure;

$R^6$ and $R^7$ are independently hydrogen, halogen, substituted or unsubstituted alkyl, substituted or unsubstituted aryl, —$OR^{12}$, —$OC(O)R^{12}$, —$OC(O)OR^{12}$, or —$OC(O)NR^{13}R^{14}$;

$R^1$ is —$C(O)R^8$;

$R^2$ is hydrogen or unsubstituted alkyl;

$R^4$ is —$OR^9$;

$R^8$ and $R^9$ are independently hydrogen or unsubstituted alkyl;

$R^{12}$, $R^{13}$ and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{15}$ is hydrogen or unsubstituted alkyl.

2. The compound of claim 1, having the formula:

(VII)

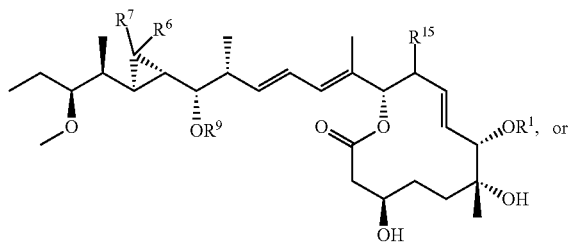

(VIII)

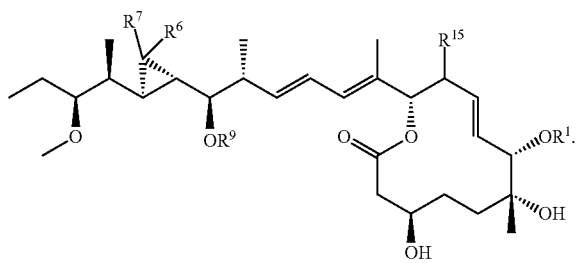

3. The compound of claim 1, wherein R$^{15}$ is hydrogen or C$_1$-C$_4$ unsubstituted alkyl.
4. The compound of claim 3 wherein R$^{15}$ is methyl.
5. The compound of claim 2 wherein R$^9$ is hydrogen.
6. The compound of claim 4, wherein X$^2$ is O.
7. The compound of claim 1, wherein X$^2$ is C(R$^6$)(R$^7$).
8. The compound of claim 7, wherein R$^6$ and R$^7$ are independently hydrogen, halogen, or methyl.
9. The compound of claim 8, wherein R$^6$ and R$^7$ are hydrogen or —F.
10. The compound of claim 1 having the formula:

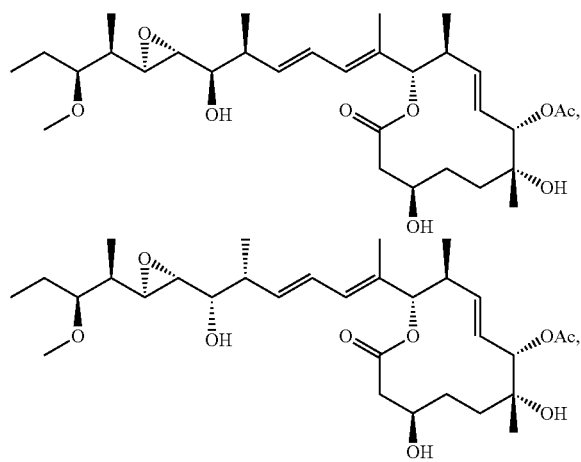

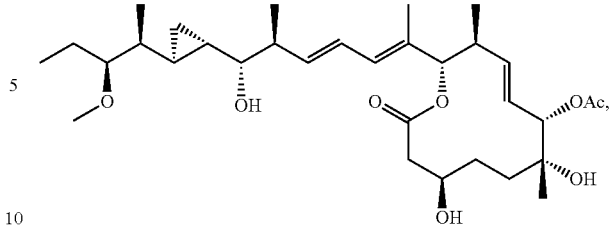

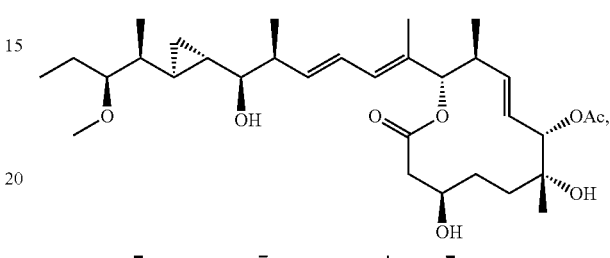

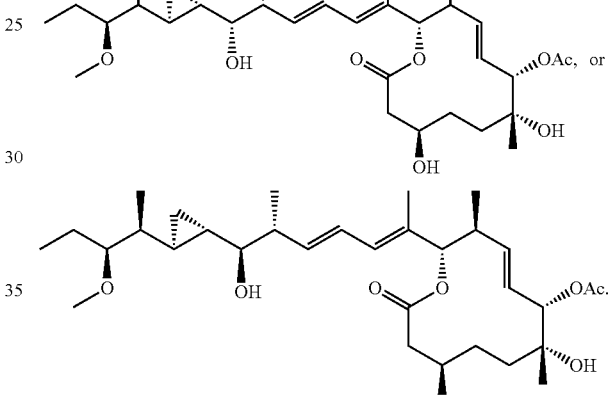

11. A pharmaceutical composition comprising the compound of claim 1 and a pharmaceutical excipient.

12. A method of abating cancer, the method comprising administering to a subject in need thereof a therapeutically effective amount the compound of claim 1.

13. The method of claim 12, wherein the cancer is leukemia, lymphoma, metastatic cancer, or bone cancer.

14. The compound of claim 1, wherein when X$^2$ is oxygen then the chiral carbon at R$^2$ has (R) stereochemistry and the chiral carbon at R$^4$ has (S) stereochemistry, and the compound is optically pure.

* * * * *

```
SEQUENCE LISTING

<160> NUMBER OF SEQ ID NOS: 12

<210> SEQ ID NO 1
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 1
gaaccaaaat cacttcccca aggaagg                                         27

<210> SEQ ID NO 2
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 2
ggcctgatgg gtcttatcta tgg                                             23

<210> SEQ ID NO 3
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 3
aatgaggtcc ccacgtttct cgggtgt                                         27

<210> SEQ ID NO 4
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 4
ttagatggaa gctggctcaa gag                                             23
```

-continued

```
<210> SEQ ID NO 5
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 5
gctgaaggac catttattac tggag                                          25

<210> SEQ ID NO 6
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 6
tcaatggaga tagcaaaggt attataac                                       28

<210> SEQ ID NO 7
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 7
ttcttgctgt gttctttctc ccaca                                          25

<210> SEQ ID NO 8
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 8
agatttacta ggagcacatt atgagtg                                        27

<210> SEQ ID NO 9
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 9
tggtcaccag ggctgctt                                                  18

<210> SEQ ID NO 10
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 10
tggtcaccag ggctgctt                                                  18

<210> SEQ ID NO 11
<211> LENGTH: 20
<212> TYPE: DNA
<213> ORGANISM: Artificial Sequence
<220> FEATURE:
```

```
<223> OTHER INFORMATION: Synthetic polynucleotide

<400> SEQUENCE: 11
agcttcccgt tctcagcctt                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 12
agcttcccgt tctcagcctt                                                    20
```